United States Patent [19]
Belagaje et al.

[11] Patent Number: 5,304,473
[45] Date of Patent: Apr. 19, 1994

[54] A-C-B PROINSULIN, METHOD OF MANUFACTURING AND USING SAME, AND INTERMEDIATES IN INSULIN PRODUCTION

[75] Inventors: Rama M. Belagaje, Indianapolis; Richard D. DiMarchi, Carmel; William F. Heath, Jr., Indianapolis; Harlan B. Long, Carmel, all of Ind.

[73] Assignee: Eli Lilly and Company, Indianapolis, Ind.

[21] Appl. No.: 715,183

[22] Filed: Jun. 11, 1991

[51] Int. Cl.$^5$ .................. C12P 19/34; C12N 1/20; A61K 37/02; C07K 5/00
[52] U.S. Cl. ................. 435/69.7; 435/252.33; 530/303; 530/350; 536/23.51; 514/3
[58] Field of Search ........... 435/91, 69.7, 252.33; 514/3; 530/350, 303; 536/27, 23.51

[56] References Cited

U.S. PATENT DOCUMENTS 4,703,039 10/1987 Hawigek et al. .................. 514/21

FOREIGN PATENT DOCUMENTS 0375437 12/1989 European Pat. Off. ....... C07K 7/40
0383472 8/1990 European Pat. Off. ....... C07K 7/40
9011299 10/1990 World Int. Prop. O. ..... C07K 7/40

OTHER PUBLICATIONS

Peavy et al. J.B.C. 260:13989–13994 1990.
Bayne et al., Gene 66:235–244 1988.
Lin et al. (1975) Biochemistry USA 14:1559–1563.
Burgess et al. (1990) J. Cell. Biol. 111:2129–2138.
Lazar et al. (1988) Mol. and Cell. Biol. 8:1247–1252.

*Primary Examiner*—David L. Lacey
*Assistant Examiner*—Donald E. Adams
*Attorney, Agent, or Firm*—Richard B. Murphy; Leroy Whitaker

[57] ABSTRACT

The instant invention provides novel molecules derived from the components of proinsulin using recombinant DNA technology. The invention provides molecules of the formula A—C—B wherein A is the A-chain of an insulin species, B is the B-chain of an insulin species and C is a connecting peptide. These molecules possess insulin-like activity and are useful for the treatment of diabetes mellitus, particularly non-insulin dependent diabetes mellitus. These molecules are also useful for the production of insulin and constitute a novel pathway for the recombinant production of insulin species. The invention provides a method of making insulin proceeding through the compounds of the invention as intermediates. The instant invention further provides recombinant DNA compounds which encode the compounds of the invention.

41 Claims, 30 Drawing Sheets oligo 1

AGCTTCATATGGGCATTGTGGAACAATGCTGTACCAGCATCTGCTCCCTG

AGTATACCCGTAACACCTTGTTACGACATGGTCGTAGACGAGGGAC oligo 5 oligo 1 continued       oligo 2

TACCAGCTGGAGAACTACTGCAACCGCCGTGAGGCAGAGGACCTGCAGGTG

ATGGTCGACCTCTTGATGACGTTGGCGGCACTCCGTCTCCTGGACGTCCAC oligo 5 continued       oligo 6 oligo 2 continued       oligo 3

GGTCAGGTGGAGCTGGGCGGTGGCCCGGGTGCAGGCAGCCTGCAGCCGCTG

CCAGTCCACCTCGACCCGCCACCGGGCCCACGTCCGTCGGACGTCGGCGAC oligo 6 continued       oligo 7 oligo 3 continued

GCCCTGGAGGGTTCCCTGCAGAAGCGTTTTTTGAACCAACACCTGTGCGGC

CGGGACCTCCCAAGGGACGTCTTCGCAAAAAACTTGGTTGTGGACACGCCG oligo 7 continued oligo 4

TCCCACCTGGTGGAAGCTCTGTACCTGGTGTGCGGTGAACGTGGCTTCTTC

AGGGTGGACCACCTTCGAGACATGGACCACACGCCACTTGCACCGAAGAAG oligo 8 oligo 4 continued

TACACCCCGAAGACCTAGGATCCG 3'

ATGTGGGGCTTCTGGATCCTAGGCTTAA 5' oligo 8 continued

FIGURE 17

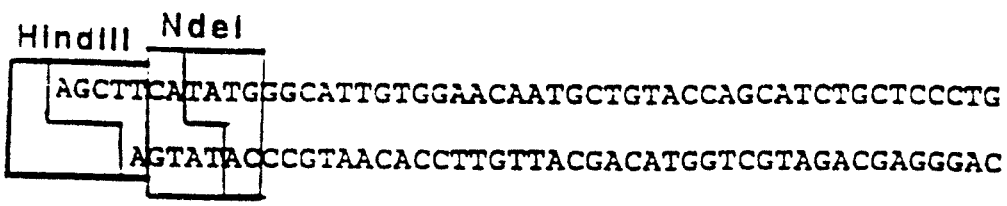

```
TACCAGCTGGAGAACTACTGCAACCGCCGTGAGGCAGAGGACCTGCAGGTG
ATGGTCGACCTCTTGATGACGTTGGCGGCACTCCGTCTCCTGGACGTCCAC

GGTCAGGTGGAGCTGGGCGGTGGCCCGGGTGCAGGCAGCCTGCAGCCGCTG
CCAGTCCACCTCGACCCGCCACCGGGCCCACGTCCGTCGGACGTCGGCGAC

GCCCTGGAGGGTTCCCTGCAGAAGCGTTTTTTGAACCAACACCTGTGCGGC
CGGGACCTCCCAAGGGACGTCTTCGCAAAAAACTTGGTTGTGGACACGCCG

TCCCACCTGGTGGAAGCTCTGTACCTGGTGTGCGGTGAACGTGGCTTCTTC
AGGGTGGACCACCTTCGAGACATGGACCACACGCCACTTGCACCGAAGAAG
```

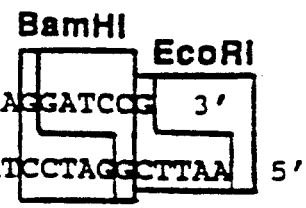

A-C-B PROINSULIN, METHOD OF MANUFACTURING AND USING SAME, AND INTERMEDIATES IN INSULIN PRODUCTION

BACKGROUND OF THE INVENTION

The extensive study of diabetes has resulted in insulin being arguably the best understood of all protein molecules. Consequently, insulin has become the preferred substrate to probe the effects of alterations in primary structure on higher orders of protein structure and function. Recombinant DNA technology facilitates the generation of novel insulin analogs for SAR and therapeutic applications. The catalogued effects of these alterations hopefully will unlock the rules governing the relationship between primary and higher orders of protein conformation. However, such modifications in primary structure have been relatively minor in relation to the native sequence. However, such limited diversions from the native sequence provide little insight as to what lies along more divergent pathways.

The pursuit of biochemistry is to design artificial molecules to perform designated functions rather than to rely on the chance discovery of a naturally occurring compound possessing the desired properties. Notwithstanding significant advances, the art is essentially barren of examples of synthetic analogs which differ markedly in primary structure from their naturally occurring counterparts. The instant invention uses the well characterized insulin molecule to embark on the development of a synthetic analog of proinsulin which is markedly different in structure and physical properties from the naturally occurring proinsulin molecule and known proinsulin analogs.

Insulin is a protein consisting of two subunit polypeptides commonly referred to as the A-chain and the B-chain covalently cross linked via disulfide bonds. Human insulin, one representative example of the insulin structure, may be diagrammed as shown in FIG. 29A. The biochemical pathway for the production of insulin is well known in the art and may be found in general references on the subject. (See e.g., Stryer, L., *Biochemistry*, 2nd. Ed., 1981, W. H. Freeman & Co., San Francisco, pp. 847–848). The naturally occurring in vivo biochemical route to insulin leads through the preproinsulin and proinsulin intermediates.

Insulin is recombinantly produced via the expression of proinsulin followed by enzymatic processing. Proinsulin, the immediate precursor of insulin, is a single chain protein. The two chain insulin molecule is produced by the excision of an internal region, commonly referred to as the C-region or C-peptide, of proinsulin. Subsequent to the formation of the intrachain and interchain disulfide cross-linkages, the internal polypeptide sequence (C-peptide) is deleted by the action of the trypsin and carboxypeptidase B enzymes resulting in the functional insulin molecule.

The proinsulin gene is translated in the order corresponding to the B-chain/C-peptide/A-chain amino acid sequence. Since recombinant insulin production begins with proinsulin rather than the preproinsulin molecule, the recombinant proinsulin molecule characteristically possesses a methionine residue at its amino-terminus. Consequently, this met derived from the N-terminus of proinsulin is carried through and remains at the amino terminus of the insulin B-chain. This methionine residue is not intrinsically removed by the bacterial host cell. It is therefore necessary to chemically or enzymatically remove this N-terminal methionine in vitro to achieve the native proinsulin or insulin molecule.

The action of methionyl amino peptidase (MAP), a protein indigenous to *E. coli*, will remove an N-terminal deformylated methionine provided the second residue is not arginine, aspartate, glutamine, glutamate, isoleucine, leucine, lysine or methionine. Examination of the primary structure of the insulin molecule, human insulin being a representative example shown in FIG. 29, demonstrates that the N-terminal residue of the B-chain, corresponding to the N-terminal residue of natural proinsulin, is phenylalanine. This transcriptional and translational order prevents the removal of the N-terminal methionine of the recombinantly *E. coli* produced proinsulin molecule by MAP. However, the N-terminal amino acid of the A-chain is glycine whose presence does not inhibit the action of MAP. Thus, if one could reverse the sequence of translation from B-chain/C-peptide/A-chain to A-chain/C-peptide/B-chain, the intrinsic action of MAP would eliminate the N-terminal methionine. This would consequently obviate the need for post-translational removal of the N-terminal Met thereby incurring a substantial commercial and technical advantage.

SUMMARY OF THE INVENTION

The instant invention provides a method for the production of a functional insulin molecule or insulin analog which comprises novel starting materials and intermediates. This new pathway proceeds through an insulin precursor created by inversion of the coding sequence of proinsulin from B-chain/C-peptide/A-chain to A-chain/C-peptide/B-chain. The novel insulin precursor created eliminates the need for post-translational chemical or enzymatic removal of the N-terminal methionine of the recombinant insulin molecule. The invention further provides novel intermediate insulin precursors which constitute essential elements in a human engineered biosynthetic pathway to generate insulin. These novel insulin precursors possess: (a) greater insulin-like activity than the naturally occurring proinsulin, (b) a longer half-life in vivo with respect to insulin characteristic of natural proinsulin, and (c) demonstrate an enhanced ability to bind the IGF-I receptor when compared to natural proinsulin. Further teachings of this invention disclose the limitations discerned from study and design of this new molecule, particularly with respect to the C-peptide, which will be instructive in the design of analogous proinsulin and insulin molecules.

BRIEF DESCRIPTION OF THE DRAWINGS

The restriction site and function maps presented in the accompanying drawings are approximate representations of the recombinant DNA vectors discussed herein. The restriction site information is not exhaustive; therefore there may be more restriction sites of a given type on the vector than are illustrated in the drawings.

FIG. 17—Shows the specific DNA sequences involved in the construction of one analog of the human ACB-PI gene employed in the design of the ACB-PI gene.

FIG. 18—Illustrates one embodiment of the placement of restriction endonuclease cleavage points designed into one analog of the human ACB-PI coding sequence which facilitate integration into the particular cloning vectors exemplified herein.

DETAILED DESCRIPTION OF THE INVENTION

DEFINITIONS

Figure 1:
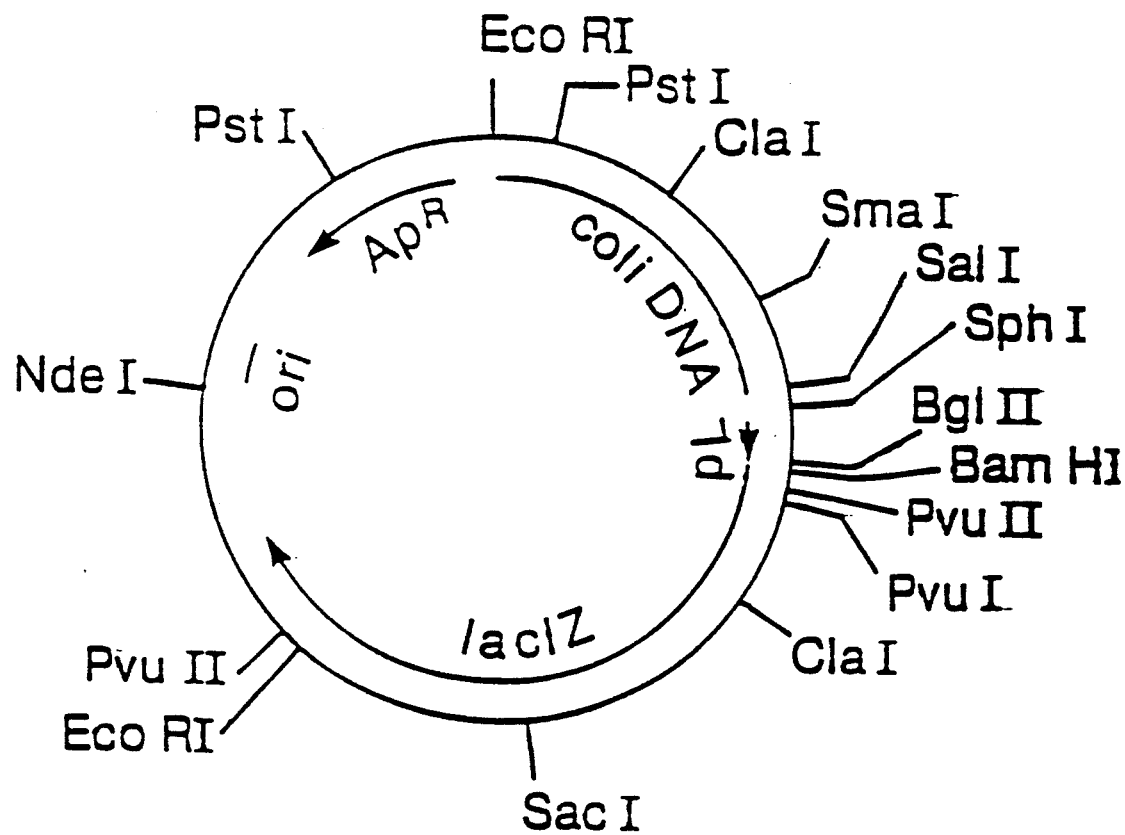
FIG. 1—A restriction site and function map of plasmid pKC283.

For purposes of the present invention as disclosed and claimed herein, the following terms are defined below:

ACB-hPI—an abbreviation for human ACB-proinsulin

ACB-PI—an abbreviation of ACB-proinsulin.

ACB-proinsulin—is a polypeptide molecule which contains (a) the amino acid sequence corresponding to the insulin A-chain or a functional analog thereof linked sequentially to, (b) a connecting peptide which links the carboxyl terminal amino acid of the insulin A-chain to the amino terminal amino acid of the insulin B-chain, said connecting peptide comprising at least 8 amino acids, linked sequentially to (c) the amino acid sequence corresponding to the insulin B-chain or a functional analog thereof.

A-chain—the A-chain of insulin or a functional analog thereof which forms one of the two subunits of an insulin molecule.

Ala—the amino acid alanine.

Analog—a compound which is structurally similar to another. When used in reference to polypeptides it refers to primary, secondary, or tertiary structure.

Arg—the amino acid arginine.

Asn—the amino acid asparagine.

Asp—the amino acid aspartic acid.

B-chain—the B-chain of insulin or a functional analog thereof corresponding to the larger subunit of the two chain insulin protein.

Base pair (bp)—refers to DNA or RNA. The abbreviations A, C, G, and T correspond to the 5'-monophosphate forms of the nucleotides (deoxy)adenine, (deoxy)cytidine, (deoxy)guanine, and (deoxy)thymidine respectively when they occur in DNA molecules. The abbreviations U, C, G, and T correspond to the 5'-monophosphate forms of the nucleosides uracil, cytidine, guanine, and thymine respectively when they occur in RNA molecules. In double stranded DNA, base pair may refer to a partnership of A with T or C with G. In a DNA/RNA heteroduplex, base pair may refer to a partnership of T with U or C with G.

BCA Proinsulin—naturally occurring proinsulin or functional analogs thereof. It is a term used to distinguish the ACB-proinsulin molecule described herein wherein the translation order of the insulin subunits has been reversed.

C-peptide—a polypeptide sequence of at least 8 amino acids where this polypeptide is placed between the insulin A-chain amino acid sequence (or the amino acid sequence of an insulin A-chain functional analog) and the insulin B-chain amino acid sequence (or the amino acid sequence of an insulin B-chain analog) allowing sufficient conformational permutations to allow the proper formation the intrachain and inter-chain disulfide bridges of the insulin precursor molecule.

Cys—the amino acid cysteine or one-half of a cystine residue covalently linked via a disulfide bridge to another one-half cystine residue.

DNA—deoxyribonucleic acid.

EDTA—an abbreviation for ethylenediamine tetraacetic acid.

ED50—an abbreviation for half-maximal value.

FAB-MS—an abbreviation for fast atom bombardment mass spectrometry.

Functional analog—refers to a molecule or compound having similar functional properties but a modified structure relative to the naturally occurring form of that molecule or compound.

Gln—the amino acid glutamine.

Glu—the amino acid glutamic acid.

Gly—the amino acid glycine.

His—the amino acid histidine.

hPI—an abbreviation for human proinsulin.

Insulin—a protein hormone or functional analog thereof that lowers the level of blood sugar and stimulates the utilization of glucose and blocks glycogenolysis. Insulin is found universally throughout the mammalian kingdom where of the pancreas.

Insulin precursor—a single stranded polypeptide which when an internal amino acid sequence is excised results in a two-chain insulin molecule or insulin analog.

Ile—the amino acid isoleucine.

Leu—the amino acid leucine.

Lys—the amino acid lysine.

Met—the amino acid methionine or its deformylated analog.

Met-ACB-PI—an abbreviation for methionyl ACB proinsulin.

Met-ACB-hPI—an abbreviation for methionyl ACB human proinsulin.

Met-ACB-Proinsulin—an ACE-proinsulin molecule with a methionine residue covalently linked to the amino terminus of the ACB-proinsulin molecule.

mRNA—messenger RNA.

MWCO—an abbreviation for molecular weight cutoff.

NIDDM—an abbreviation for non-insulin dependent diabetes mellitus.

Nle—norleucine.

Nva—norvaline.

Orn—ornithine.

Phe—the amino acid phenylalanine.

Plasmid—a extrachromosomal self-replicating genetic element.

PMSF—an abbreviation for phenylmethylsulfonyl fluoride.

Pro—the amino acid proline.

Reading frame—the nucleotide sequence from which translation occurs "read" in triplets by the translational apparatus of tRNA and ribosomes and associated factors each triplet corresponding to a particular amino acid. Because each triplet is distinct and of the same length the coding sequence must be a multiple of three, a base pair insertion or deletion (termed a frameshift mutation) may result in two different proteins being coded for by the same sequence. To insure against this, the triplet codons corresponding to the desired polypeptide must be aligned in multiples of three from the initiation codon, i.e., the correct "reading frame" being maintained.

Recombinant DNA Cloning Vector—any autonomously replicating agent, including, but not limited to, plasmids and phages, comprising a DNA molecule to which one or more additional DNA segments can be or have been added.

Recombinant DNA Expression vector—any recombinant DNA cloning vector into which a promoter has been incorporated.

Replicon—a DNA sequence that controls and allows for autonomous replication of a plasmid or other vector.

RNA—ribonucleic acid.

RP-HPLC—an abbreviation for reverse-phase high performance liquid chromatography.

Ser—the amino acid serine.

Thr—the amino acid threonine.

Transcription—the process whereby information contained in a nucleotide sequence of DNA is transferred to a complementary RNA sequence.

Translation—the process whereby the genetic information of messenger RNA is used to specify and direct the synthesis of a polypeptide chain.

Tris—an abbreviation for tris(hydroxymethyl) aminomethane.

Trp—the amino acid tryptophan.

Tyr—the amino acid tyrosine.

Val—the amino acid valine.

Vector—a replicon used for the transformation of cells in gene manipulation bearing polynucleotide sequences corresponding to appropriate protein molecules which when combined with appropriate control sequences confer specific properties on the host cell to be transformed. Plasmids, viruses and bacteriophage are suitable vectors, since they are replicons in their own right. Artificial vectors are constructed by cutting and joining DNA molecules from different sources using restriction enzymes and ligases. Vectors include Recombinant DNA Cloning vectors and Recombinant DNA expression vectors.

X-gal—an abbreviation for 5-bromo-4-chloro-3 indolyl beta-D-galactoside.

DETAILED DESCRIPTION OF THE INVENTION The instant invention provides polypeptide compounds of the formula:

$$Met_x-A-C-B$$

wherein:
Met = the amino acid methionine,
x = 0 or 1,
A = the A chain of insulin or a functional derivative thereof,
B = the B chain of insulin or a functional derivative thereof,
C = the C peptide of insulin or a peptide of the formula:

$$X_1-X_2-P-X_3-X_4,$$

wherein:
$X_1$, $X_2$, $X_3$, and $X_4$ are basic amino acids,
$X_1$, $X_2$, $X_3$, and $X_4$ are the same or different, and,
P is a peptide of from 4 to about 35 amino acids which does not contain a cysteine residue.

Compounds of the formula 1 are useful in two seperate roles:

1) as precursors to the recombinant production of insulin, and (2) independent therapeutic compounds.

The utility of these compounds as precursors to insulin is described later.

Compounds of the formula 1 constitute novel "Proinsulin" proteins or insulin precursors, hereinafter termed "ACB-proinsulins", which possesses independently beneficial properties apart from being intermediates on a novel route to insulin as described below. In the preferred practice of the invention as exemplified herein said compound of the formula 1 comprises the amino acid sequence: (Seq. ID No.1)

```
Gly Ile Val Glu Gln Cys Cys Thr Ser
Ile Cys Ser Leu Tyr Gln Leu Glu Asn
Tyr Cys Asn Arg Arg Glu Ala Glu Asp
Leu Gln Val Gly Gln Val Glu Leu Gly
Gly Gly Pro Gly Ala Gly Ser Leu Gln
Pro Leu Ala Leu Glu Gly Ser Leu Gln
Lys Arg Phe Val Asn Gln His Leu Cys
Gly Ser His Leu Val Glu Ala Leu Tyr
Leu Val Cys Gly Glu Arg Gly Phe Phe
Tyr Thr Pro Lys Thr
```

Figure 15A:
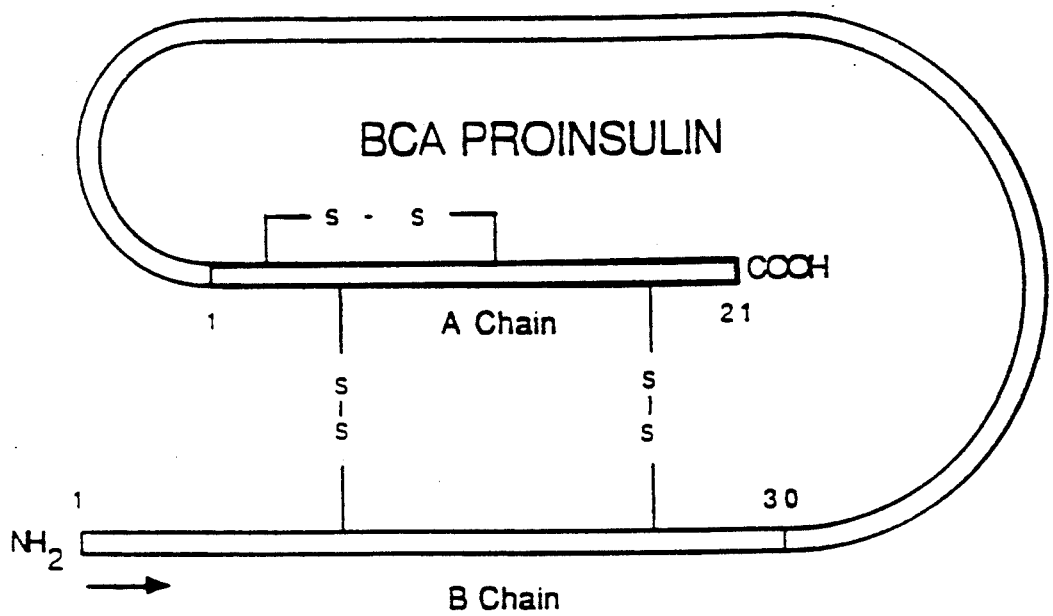
FIG. 15A—Is a schematic representation of the naturally occuring BCA proinsulin molecule.
Figure 15B:
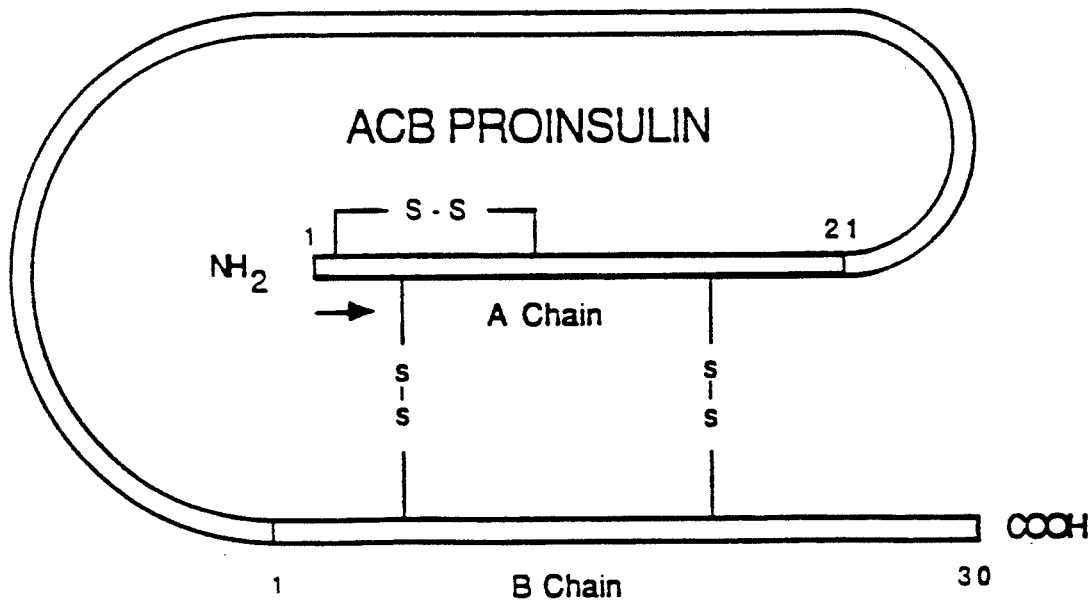
FIG. 15B—Is a schematic representation of the ACB proinsulin molecule.
Figure 16:
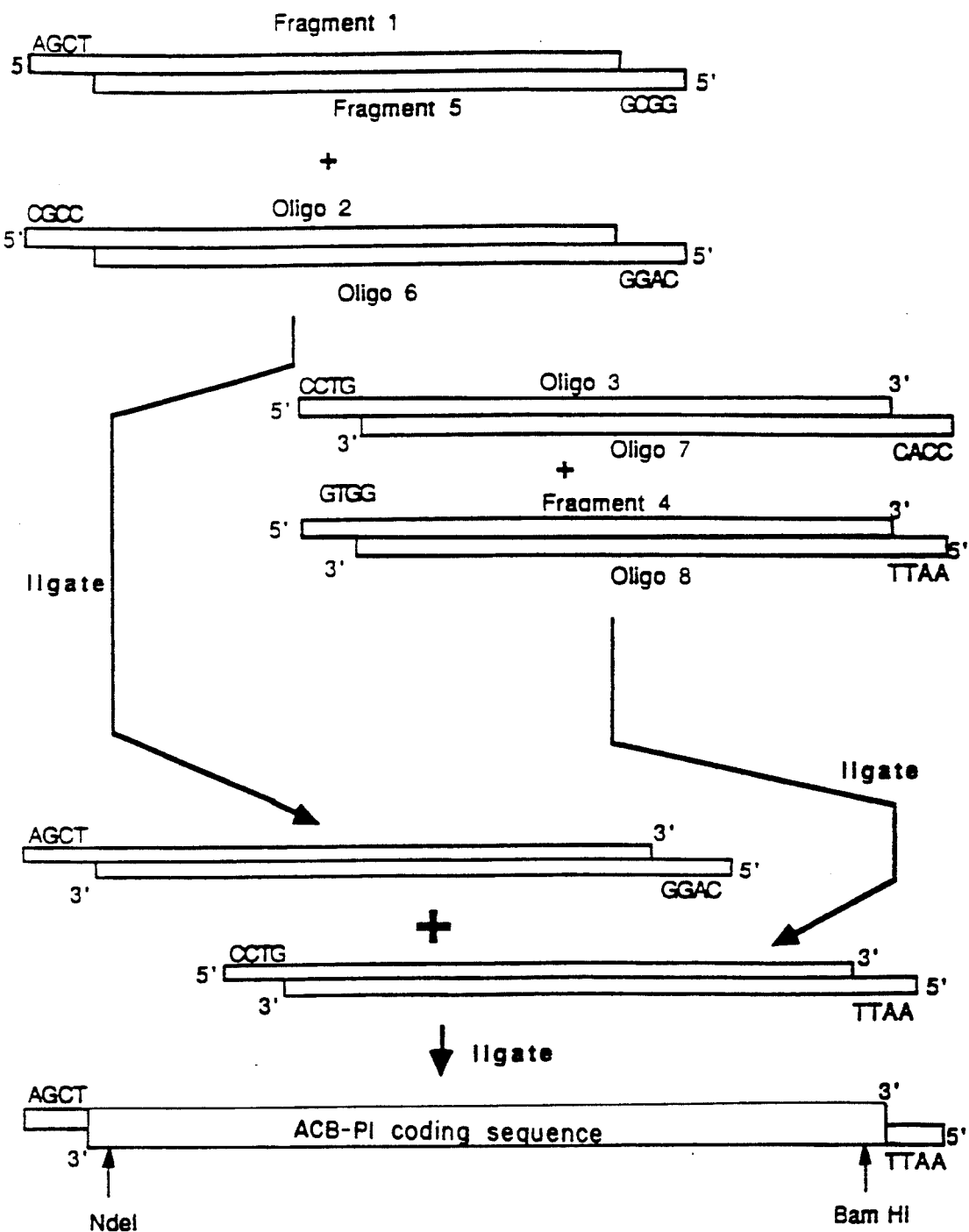
FIG. 16—A schematic representation of the method of construction of the ACB-PI coding sequence derived from a composite of compatible shorter synthetic DNA sequences.
Figure 19:
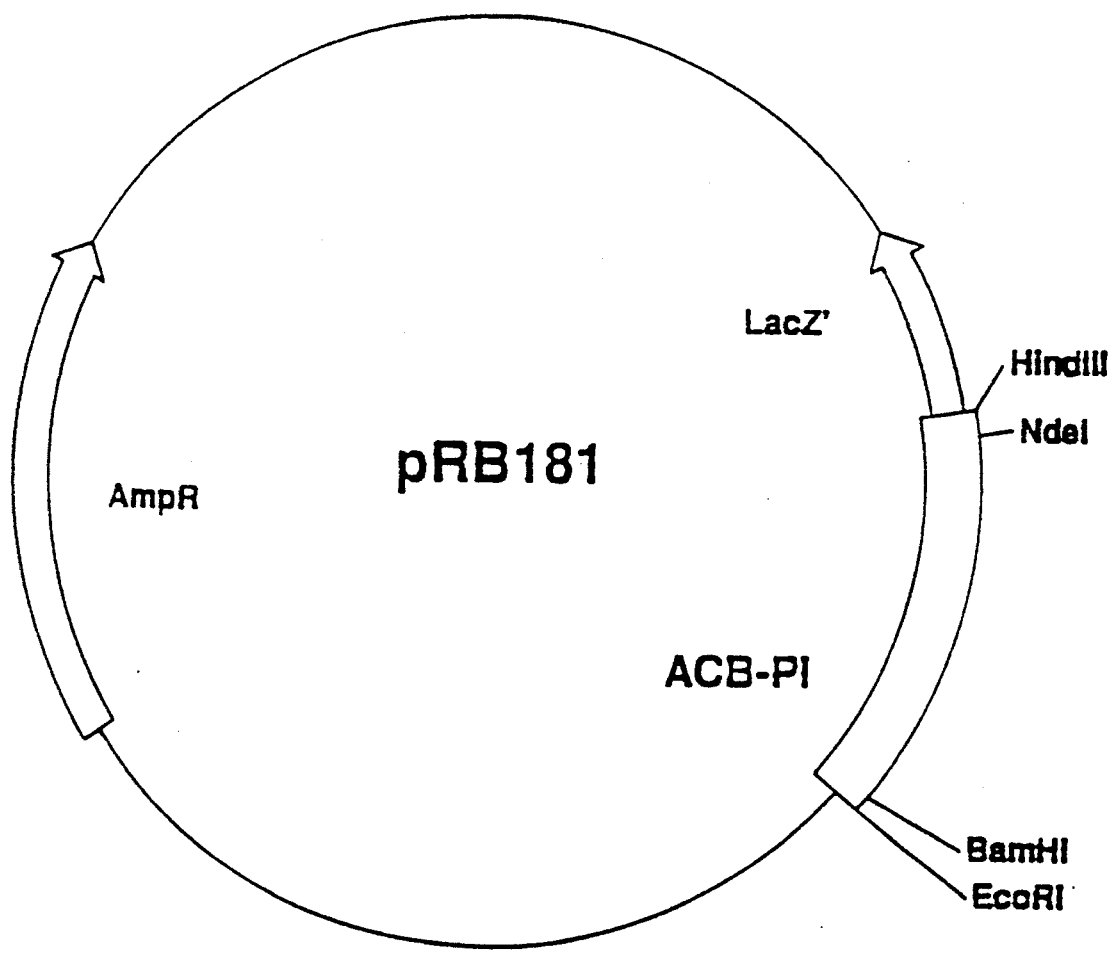
FIG. 19—A restriction site and function map of plasmid pRB181.

Examination of FIGS. 15A and B and 29A and B graphically illustrate the overall structural change between natural "BCA" proinsulin and the new, inverted, "ACB"-proinsulin. The structural changes between natural proinsulin (referred to herein and in FIG. 15A as BCA-proinsulin to differentiate it from the new inverted ACB-proinsulin as shown in FIG. 15B) and ACB-proinsulin are enormous.

It is well known in the art that certain alterations in the structure of a protein are sufficient to inhibit or entirely prevent proper formation of secondary and tertiary structure thereby resulting in a non-functional protein. This is particularly true in molecules which depend on the proper formation of disulfide cross-linkages for activity such as proinsulin and insulin. It is entirely unexpected and surprising that the gross conformational difference between ACB-proinsulin and BCA-proinsulin results in a molecule which (a) possesses significant insulin-like activity greater than native proinsulin and (b) when the C-peptide is excised, forms a functional insulin molecule with all disulfide cross-linkages properly created and without an N-terminal methionine residue on the A-chain.

It has been demonstrated that a form of proinsulin clipped at the Arg65-Gly66 bond possesses greater insulin like activity than the natural form of proinsulin, presumably as a result of freeing the amino terminal residue of the A-Chain yet retaining the size and overall structure of preinsulin. Peavy, D. E., at al., (1985) *J. Biol. Chem.*, Vol. 260, 13989–13394. The ACB-proinsulin molecule possesses a free amino terminus of the A-Chain but demonstrates enhanced activity where the C-peptide being anchored at both ends provides a more stable conformation.

The primary structure of insulin and proinsulin have been widely modified. These modifications have provided insulin and proinsulin molecules possessing a wide variety of desirable characteristics useful for treating various forms of diabetes, to facilitate commercial (especially recombinant) production, and/or to provide more desirable pharmaceutical formulations. A representative, but not exhaustive, list of such modifications is provided in Table I below. The instant invention provides ACB-proinsulin molecules incorporating primary structural changes a representative list of which appears in Table I. The method of the instant invention further provides a method to prepare insulin analogs which incorporate primary structural changes, a representative list of which appears in Table I.

TABLE 1

Insulin Analogs and Proinsulin Analogs

A. Single Amino Acid Changes

| | | | | |
|---|---|---|---|---|
| Gly $A_{21}$ | Glu $A_{21}$ | hSer $A_{21}$ | Thr $B_{10}$ | Asp $B_{25}$ |
| Ser $A_{21}$ | Leu $A_{21}$ | Gly $A_{22}$ | Asp $B_{10}$ | His $B_{25}$ |
| Ala $A_{21}$ | Met $A_{21}$ | Ala $A_{22}$ | Arg $B_{10}$ | Glu $B_{26}$ |
| His $A_{21}$ | Tyr $A_{21}$ | Asp $B_9$ | Ile $B_{12}$ | Glu $B_{27}$ |
| Asp $A_{21}$ | Val $A_{21}$ | Asn $B_9$ | His $B_{16}$ | Asp $B_{28}$ |
| Thr $A_{21}$ | Ile $A_{21}$ | His $B_9$ | Gln $B_{17}$ | Ala $B_{30}$ |
| Gln $A_{21}$ | Trp $A_{21}$ | Glu $B_{10}$ | Gln $B_{20}$ | des-$B_{30}$ |
| $Thr_{30}$—$NH_2$ | $Ala_{30}$—$NH_2$ | | | |

B. Two Amino Acid Changes

| | |
|---|---|
| Gly $A_{21}$ and Asp $B_{10}$ | His $A_{21}$ and Lys $B_{27}$ |
| Ser $A_{21}$ and Asp $B_{10}$ | Asp $A_{21}$ and Lys $B_{27}$ |
| Thr $A_{21}$ and Asp $B_{10}$ | Gly $A_{21}$ and Arg $B_{27}$ |
| Ala $A_{21}$ and Asp $B_{10}$ | Ser $A_{21}$ and Arg $B_{27}$ |
| His $A_{21}$ and Asp $B_{10}$ | Thr $A_{21}$ and Arg $B_{27}$ |
| Asp $A_{21}$ and Asp $B_{10}$ | Ala $A_{21}$ and Arg $B_{27}$ |
| Gly $A_{21}$ and Thr $B_{10}$ | Glu $B_{27}$ and Glu $B_{16}$ |
| Ser $A_{21}$ and Thr $B_{10}$ | Asp $B_5$ and Asn $B10$ |
| Thr $A_{21}$ and Thr $B_{10}$ | Glu $B_{12}$ and Gln $B_{13}$ |
| Ala $A_{21}$ and Thr $B_{10}$ | Ser $B_{14}$ and Asp $B_{17}$ |
| His $A_{21}$ and Thr $B_{10}$ | Lys $B_{28}$ and Pro $B_{29}$ |
| Asp $A_{21}$ and Thr $B_{10}$ | His $A_{21}$ and Arg $B_{27}$ |
| Gly $A_{21}$ and Arg $B_{10}$ | Asp $A_{21}$ and Arg $B_{27}$ |
| Ser $A_{21}$ and Arg $B_{10}$ | Glu $B_{12}$ and des $B_{30}$ |
| Thr $A_{21}$ and Arg $B_{10}$ | Asp $B_{10}$ and Ser $B_2$ |
| Ala $A_{21}$ and Arg $B_{10}$ | Asp $B_{10}$ and Asp $B_{28}$ |
| His $A_{21}$ and Arg $B_{10}$ | Glu $B_{10}$ and Glu $A_{13}$ |
| Asp $A_{21}$ and Arg $B_{10}$ | Glu $B_{27}$ and Ser $A_{13}$ |
| Asp $B_{10}$ and des-$B_{30}$ | Glu $B_{27}$ and Asp $A_{21}$ |
| Thr $B_{10}$ and des-$B_{30}$ | Glu $B_{27}$ and Glu $B_1$ |
| Arg $B_{10}$ and des-$B_{30}$ | Glu $B_{27}$ and Asp $B_9$ |
| Gly $A_{21}$ and Lys $B_{27}$ | Gly $A_{21}$ and Ala $B_{30}$ |
| Ser $A_{21}$ and Lys $B_{27}$ | Ser $A_{21}$ and Ala $B_{30}$ |
| Thr $A_{21}$ and Lys $B_{27}$ | Thr $A_{21}$ and Ala $B_{30}$ |
| Ala $A_{21}$ and Lys $B_{27}$ | Ala $A_{21}$ and Ala $B_{30}$ |
| des $B_{29}$ and des $B_{30}$ | hSer $A_{21}$ and Ala $B_{30}$ |

C. Three Amino Acid Changes

$A_{21}$ Gly + Lys $B_{27}$ + Gln $A_{17}$
$A_{21}$ Ser + Lys $B_{27}$ + Gln $A_{17}$
$A_{21}$ Thr + Lys $B_{27}$ + Gln $A_{17}$
$A_{21}$ Ala + Lys $B_{27}$ + Gln $A_{17}$
$A_{21}$ His + Lys $B_{27}$ + Gln $A_{17}$
$A_{21}$ Asp + Lys $B_{27}$ + Gln $A_{17}$
Gly $A_{21}$ + Lys $B_{27}$ + Gln $B_{13}$
Ser $A_{21}$ + Lys $B_{27}$ + Gln $B_{13}$
Thr $A_{21}$ + Lys $B_{27}$ + Gln $B_{13}$
Ala $A_{21}$ + Lys $B_{27}$ + Gln $B_{13}$
His $A_{21}$ + Lys $B_{27}$ + Gln $B_{13}$
Asp $A_{21}$ + Lys $B_{27}$ + Gln $B_{13}$
Gly $A_{21}$ + Arg $B_{27}$ + Gln $B_{17}$
Ser $A_{21}$ + Arg $B_{27}$ + Gln $B_{17}$
Thr $A_{21}$ + Arg $B_{27}$ + Gln $B_{17}$
Ala $A_{21}$ + Arg $B_{27}$ + Gln $B_{17}$
His $A_{21}$ + Arg $B_{27}$ + Gln $B_{17}$
Asp $A_{21}$ + Arg $B_{27}$ + Gln $B_{17}$
Gly $A_{21}$ + Arg $B_{27}$ + Gln $B_{13}$
Ser $A_{21}$ + Arg $B_{27}$ + Gln $B_{13}$
Thr $A_{21}$ + Arg $B_{27}$ + Gln $B_{13}$
Ala $A_{21}$ + Arg $B_{27}$ + Gln $B_{13}$
His $A_{21}$ + Arg $B_{27}$ + Gln $B_{13}$
Asp $A_{21}$ + Arg $B_{27}$ + Gln $B_{13}$
Asp $B_{10}$ + His $A_8$ + His $B_{25}$
Glu $B_{10}$ + Glu $A_3$ + Glu $B_{22}$
Glu $B_{27}$ + Ser $B_5$ + Asp $B_5$
Glu $B_{27}$ + His $A_8$ + Asp $B_9$
Glu $B_{27}$ + Asp $A_{21}$ + Asp $B_9$
des $B_{28}$ + des $B_{29}$ + des $B_{30}$
Gly $A_{21}$ + Asp $B_{10}$ + Ala $B_{30}$
Ser $A_{21}$ + Asp $B_{10}$ + Ala $B_{30}$
Thr $A_{21}$ + Asp $B_{10}$ + Ala $B_{30}$
Ala $A_{21}$ + Asp $B_{10}$ + Ala $B_{30}$
His $A_{21}$ + Asp $B_{10}$ + Ala $B_{30}$
Asp $A_{21}$ + Asp $B_{10}$ + Ala $B_{30}$
Gly $A_{21}$ + Thr $B_{10}$ + Ala $B_{30}$
Ser $A_{21}$ + Thr $B_{10}$ + Ala $B_{30}$
Thr $A_{21}$ + Thr $B_{10}$ + Ala $B_{30}$
Ala $A_{21}$ + Thr $B_{10}$ + Ala $B_{30}$

TABLE 1-continued

Insulin Analogs and Proinsulin Analogs

His $A_{21}$ + Thr $B_{10}$ + Ala $B_{30}$
Asp $A_{21}$ + Thr $B_{10}$ + Ala $B_{30}$
Gly $A_{21}$ + Arg $B_{10}$ + Ala $B_{30}$
Ser $A_{21}$ + Arg $B_{10}$ + Ala $B_{30}$
Thr $A_{21}$ + Arg $B_{10}$ + Ala $B_{30}$
Ala $A_{21}$ + Arg $B_{10}$ + Ala $B_{30}$
His $A_{21}$ + Arg $B_{10}$ + Ala $B_{30}$
Asp $A_{21}$ + Arg $B_{10}$ + Ala $B_{30}$
Gly $A_{21}$ + Asp $B_{10}$ + des $B_{30}$
Ser $A_{21}$ + Asp $B_{10}$ + des $B_{30}$
Thr $A_{21}$ + Asp $B_{10}$ + des $B_{30}$
Ala $A_{21}$ + Asp $B_{10}$ + des $B_{30}$
His $A_{21}$ + Asp $B_{10}$ + des $B_{30}$
Asp $A_{21}$ + Asp $B_{10}$ + des $B_{30}$
Gly $A_{21}$ + Thr $B_{10}$ + des $B_{30}$
Ser $A_{21}$ + Thr $B_{10}$ + des $B_{30}$
Thr $A_{21}$ + Thr $B_{10}$ + des $B_{30}$
Ala $A_{21}$ + Thr $B_{10}$ + des $B_{30}$
His $A_{21}$ + Thr $B_{10}$ + des $B_{30}$
Asp $A_{21}$ + Thr $B_{10}$ + des $B_{30}$
Gly $A_{21}$ + Arg $B_{10}$ + des $B_{30}$
Ser $A_{21}$ + Arg $B_{10}$ + des $B_{30}$
Thr $A_{21}$ + Arg $B_{10}$ + des $B_{30}$
Ala $A_{21}$ + Arg $B_{10}$ + des $B_{30}$
His $A_{21}$ + Arg $B_{10}$ + des $B_{30}$
Asp $A_{21}$ + Arg $B_{10}$ + des $B_{30}$
Thr $B_{10}$ + Glu $B_{28}$ + Pro $B_{29}$
Arg $B_{10}$ + Glu $B_{28}$ + Pro $B_{29}$
Asp $B_{10}$ + Lys $B_{28}$ + Pro $B_{29}$
Thr $B_{10}$ + Lys $B_{28}$ + Pro $B_{29}$
Arg $B_{10}$ + Lys $B_{28}$ + Pro $B_{29}$
Gly $A_{21}$ + Glu $B_{28}$ + Pro $B_{29}$
Ser $A_{21}$ + Glu $B_{28}$ + Pro $B_{29}$
Thr $A_{21}$ + Glu $B_{28}$ + Pro $B_{29}$
Ala $A_{21}$ + Lys $B_{28}$ + Pro $B_{29}$
His $A_{21}$ + Lys $B_{28}$ + Pro $B_{29}$
Asp $A_{21}$ + Lys $B_{28}$ + Pro $B_{29}$
Glu $B_{28}$ + Pro $B_{29}$ + Ala $B_{30}$
Glu $B_{28}$ + Pro $B_{29}$ + des $B_{30}$
Lys $B_{28}$ + Pro $B_{29}$ + Ala $B_{30}$
Lys $B_{28}$ + Pro $B_{29}$ + des $B_{30}$
Arg $B_{27}$ + Gly $A_{21}$ + Thr$B_{30}$—NH$_2$ D. Four Amino Acid Changes Gly $A_{21}$ + Lys $B_{27}$ + Gln $A_{17}$ + Gln $B_{13}$
Ser $A_{21}$ + Lys $B_{27}$ + Gln $A_{17}$ + Gln $B_{13}$
Thr $A_{21}$ + Lys $B_{27}$ + Gln $A_{17}$ + Gln $B_{13}$
Ala $A_{21}$ + Lys $B_{27}$ + Gln $A_{17}$ + Gln $B_{13}$
Asp $A_{21}$ + Lys $B_{27}$ + Gln $A_{17}$ + Gln $B_{13}$
His $A_{21}$ + Lys $B_{27}$ + Gln $A_{17}$ + Gln $B_{13}$
Gly $A_{21}$ + Arg $B_{27}$ + Gln $A_{17}$ + Gln $B_{13}$
Ser $A_{21}$ + Arg $B_{27}$ + Gln $A_{17}$ + Gln $B_{13}$
Thr $A_{21}$ + Arg $B_{27}$ + Gln $A_{17}$ + Gln $B_{13}$
Ala $A_{21}$ + Arg $B_{27}$ + Gln $A_{17}$ + Gln $B_{13}$
Asp $A_{21}$ + Arg $B_{27}$ + Gln $A_{17}$ + Gln $B_{13}$
His $A_{21}$ + Arg $B_{27}$ + Gln $A_{17}$ + Gln $B_{13}$
Glu $B_{10}$ + His $A_8$ + His $B_4$ + His $B_{27}$
des $B_{27}$ + des $B_{28}$ + des $B_{29}$ + des $B_{30}$
Gly $A_{21}$ + Asp $B_{10}$ + Glu $B_{28}$ + Pro $B_{29}$
Ser $A_{21}$ + Asp $B_{10}$ + Glu $B_{28}$ + Pro $B_{29}$
Thr $A_{21}$ + Asp $B_{10}$ + Glu $B_{28}$ + Pro $B_{29}$
Ala $A_{21}$ + Asp $B_{10}$ + Glu $B_{28}$ + Pro $B_{29}$
His $A_{21}$ + Asp $B_{10}$ + Glu $B_{28}$ + Pro $B_{29}$
Asp $A_{21}$ + Asp $B_{10}$ + Glu $B_{28}$ + Pro $B_{29}$
Gly $A_{21}$ + Thr $B_{10}$ + Glu $B_{28}$ + Pro $B_{29}$
Ser $A_{21}$ + Thr $B_{10}$ + Glu $B_{28}$ + Pro $B_{29}$
Thr $A_{21}$ + Thr $B_{10}$ + Glu $B_{28}$ + Pro $B_{29}$
Ala $A_{21}$ + Thr $B_{10}$ + Glu $B_{28}$ + Pro $B_{29}$
His $A_{21}$ + Thr $B_{10}$ + Glu $B_{28}$ + Pro $B_{29}$
Asp $A_{21}$ + Thr $B_{10}$ + Glu $B_{28}$ + Pro $B_{29}$
Gly $A_{21}$ + Arg $B_{10}$ + Glu $B_{28}$ + Pro $B_{29}$
Ser $A_{21}$ + Arg $B_{10}$ + Glu $B_{28}$ + Pro $B_{29}$
Thr $A_{21}$ + Arg $B_{10}$ + Glu $B_{28}$ + Pro $B_{29}$
Ala $A_{21}$ + Arg $B_{10}$ + Glu $B_{28}$ + Pro $B_{29}$
His $A_{21}$ + Arg $B_{10}$ + Glu $B_{28}$ + Pro $B_{29}$
Asp $A_{21}$ + Arg $B_{10}$ + Glu $B_{28}$ + Pro $B_{29}$
Gly $A_{21}$ + Asp $B_{10}$ + Lys $B_{28}$ + Pro $B_{29}$
Ser $A_{21}$ + Asp $B_{10}$ + Lys $B_{28}$ + Pro $B_{29}$
Thr $A_{21}$ + Asp $B_{10}$ + Lys $B_{28}$ + Pro $B_{29}$
Ala $A_{21}$ + Asp $B_{10}$ + Lys $B_{28}$ + Pro $B_{29}$
His $A_{21}$ + Asp $B_{10}$ + Lys $B_{28}$ + Pro $B_{29}$
Asp $A_{21}$ + Asp $B_{10}$ + Lys $B_{28}$ + Pro $B_{29}$
Gly $A_{21}$ + Thr $B_{10}$ + Lys $B_{28}$ + Pro $B_{29}$
Ser $A_{21}$ + Thr $B_{10}$ + Lys $B_{28}$ + Pro $B_{29}$
Thr $A_{21}$ + Thr $B_{10}$ + Lys $B_{28}$ + Pro $B_{29}$
Ala $A_{21}$ + Thr $B_{10}$ + Lys $B_{28}$ + Pro $B_{29}$
His $A_{21}$ + Thr $B_{10}$ + Lys $B_{28}$ + Pro $B_{29}$
Asp $A_{21}$ + Thr $B_{10}$ + Lys $B_{28}$ + Pro $B_{29}$
Gly $A_{21}$ + Arg $B_{10}$ + Lys $B_{28}$ + Pro $B_{29}$
Ser $A_{21}$ + Arg $B_{10}$ + Lys $B_{28}$ + Pro $B_{29}$
Thr $A_{21}$ + Arg $B_{10}$ + Lys $B_{28}$ + Pro $B_{29}$
Ala $A_{21}$ + Arg $B_{10}$ + Lys $B_{28}$ + Pro $B_{29}$
His $A_{21}$ + Arg $B_{10}$ + Lys $B_{28}$ + Pro $B_{29}$
Asp $A_{21}$ + Arg $B_{10}$ + Lys $B_{28}$ + Pro $B_{29}$
Gly $A_{21}$ + Glu $B_{28}$ + Pro $B_{29}$ + Ala $B_{30}$
Ser $A_{21}$ + Glu $B_{28}$ + Pro $B_{29}$ + Ala $B_{30}$
Thr $A_{21}$ + Glu $B_{28}$ + Pro $B_{29}$ + Ala $B_{30}$
Ala $A_{21}$ + Glu $B_{28}$ + Pro $B_{29}$ + Ala $B_{30}$
His $A_{21}$ + Glu $B_{28}$ + Pro $B_{29}$ + Ala $B_{30}$
Asp $A_{21}$ + Glu $B_{28}$ + Pro·$B_{29}$ + Ala $B_{30}$
Gly $A_{21}$ + Lys $B_{28}$ + Pro $B_{29}$ + Ala $B_{30}$
Ser $A_{21}$ + Lys $B_{28}$ + Pro $B_{29}$ + Ala $B_{30}$
Thr $A_{21}$ + Lys $B_{28}$ + Pro $B_{29}$ + Ala $B_{30}$
Ala $A_{21}$ + Lys $B_{28}$ + Pro $B_{29}$ + Ala $B_{30}$
His $A_{21}$ + Lys $B_{28}$ + Pro $B_{29}$ + Ala $B_{30}$
Asp $A_{21}$ + Lys $B_{28}$ + Pro $B_{29}$ + Ala $B_{30}$
Gly $A_{21}$ + Glu $B_{28}$ + Pro $B_{29}$ + des $B_{30}$
Ser $A_{21}$ + Glu $B_{28}$ + Pro $B_{29}$ + des $B_{30}$
Thr $A_{21}$ + Glu $B_{28}$ + Pro $B_{29}$ + des $B_{30}$
Ala $A_{21}$ + Glu $B_{28}$ + Pro $B_{29}$ + des $B_{30}$
His $A_{21}$ + Glu $B_{28}$ + Pro $B_{29}$ + des $B_{30}$
Asp $A_{21}$ + Glu $B_{28}$ + Pro $B_{29}$ + des $B_{30}$
Gly $A_{21}$ + Lys $B_{28}$ + Pro $B_{29}$ + des $B_{30}$
Ser $A_{21}$ + Lys $B_{28}$ + Pro $B_{29}$ + des $B_{30}$
Thr $A_{21}$ + Lys $B_{28}$ + Pro $B_{29}$ + des $B_{30}$
Ala $A_{21}$ + Lys $B_{28}$ + Pro $B_{29}$ + des $B_{30}$
His $A_{21}$ + Lys $B_{28}$ + Pro $B_{29}$ + des $B_{30}$
Asp $A_{21}$ + Lys $B_{28}$ + Pro $B_{29}$ + des $B_{30}$
Asp $B_{10}$ + Glu $B_{28}$ + Pro $B_{29}$ + Ala $B_{30}$
Thr $B_{10}$ + Glu $B_{28}$ + Pro $B_{29}$ + Ala $B_{30}$
Arg $B_{10}$ + Glu $B_{28}$ + Pro $B_{29}$ + Ala $B_{30}$
Asp $B_{10}$ + Lys $B_{28}$ + Pro $B_{29}$ + Ala $B_{30}$
Thr $B_{10}$ + Lys $B_{28}$ + Pro $B_{29}$ + Ala $B_{30}$
Arg $B_{10}$ + Lys $B_{28}$ + Pro $B_{29}$ + Ala $B_{30}$
Asp $B_{10}$ + Glu $B_{28}$ + Pro $B_{29}$ + des $B_{30}$
Thr $B_{10}$ + Glu $B_{28}$ + Pro $B_{29}$ + des $B_{30}$
Arg $B_{10}$ + Glu $B_{28}$ + Pro $B_{29}$ + des $B_{30}$
Asp $B_{10}$ + Lys $B_{29}$ + Pro $B_{29}$ + des $B_{30}$
Thr $B_{10}$ + Lys $B_{29}$ + Pro $B_{29}$ + des $B_{30}$
Arg $B_{10}$ + Lys $B_{29}$ + Pro $B_{29}$ + des $B_{30}$
des $B_{27}$ + des $B_{28}$ + des $B_{29}$ + des $B_{30}$ E. Five amino acid changes:

des $B_{26}$ + des $B_{27}$ + des $B_{28}$ + des $B_{29}$ + des $B_{30}$

Although it is preferred to employ the naturally occurring C-peptide sequence as indicated above, variations in the length and amino acid sequence of this peptide are permissible and will nevertheless result in a functional ACB-PI molecule. Molecular modeling studies indicate that the C-peptide region of the above ACB-PIs may be as short as eight amino acids. These studies further indicate that the C-peptide can be longer than its natural length (35 amino acids in human proinsulin) and still permit proper formation of secondary, tertiary and quaternary structure of the mature insulin molecule. The only requirements are (1) that they be of sufficient length to permit proper disulfide bond formation in the ACB-proinsulin molecule, and (2) that they be cleavable from the ACB-PI molecule with accompanying insulin formation.

Other embodiments of this invention include rabbit, monkey, horse, rat I, rat II, porcine, bovine-lamb, dog, guinea pig, chinchilla, or duck ACB-proinsulin molecules. It is preferred that the amino acid sequence of the ACB-proinsulin molecule of these alternate species be the naturally occurring amino acid sequence of the A-chain followed by the naturally occurring sequence of the C-peptide followed by the naturally occurring sequence of the B-chain. Other embodiments of this invention may be directed to functional analogs of the proinsulin molecule derived from the aforementioned species.

ACB-proinsulin constructs containing the C-peptides of the formulae:

$X_1-X_2-(4-8 \text{ amino acids})-X_3-X_4$ $X_1-X_2-(9-13 \text{ amino acids})-X_3-X_4$ $X_1-X_2-(14-19 \text{ amino acids})-X_3-X_4$ $X_1-X_2-(20-24 \text{ amino acids})-X_3-X_4$ $X_1-X_2-(25-31 \text{ amino acids})-X_3-X_4$ wherein $X_1, X_2, X_3$ and $X_4$ are a basic amino acids, $X_1$, $X_2$, $X_3$ and $X_4$ are the same or different, and where the intervening amino acid sequence does not contain a cysteine residue, may also be used in the practice of the instant invention. In the preferred practice of the invention $X_1, X_2, X_3$ and $X_4$ are selected from the group comprising Arg, Lys and Orn.

Intervening peptides of a length greater than 35 amino acids are also useful in the practice of the instant invention. However, as the length of the C-peptide increases there is a concomitant increase in the conformational freedom of the ACB- proinsulin molecule possessing such an elongated C-peptide. This increased conformational freedom generally results in molecules of decreased folding efficiency. Therefore, in the preferred practice of the invention, the C-peptide is less than about 35 amino acids in length.

In addition to the novel aspects of protein structure demonstrated by these intermediates, these new compounds have also proven to be of therapeutic importance. Although the majority of the biological activity of proinsulin rests in the A and B chains, the potential effect of the C-peptide linkage reversal on the biological activity of proinsulin was unknown. By leaving the amino terminal group of glycine A-1 free, the inventors have generated an insulin analog which possesses greater insulin-like activity that natural BCA-proinsulin, yet retains the longer in vivo half-life characteristic of natural proinsulin. ACB-proinsulin also possesses the ability to stimulate DNA synthesis in smooth muscle cells by its ability to bind the IGF-I receptor.

Figure 23:
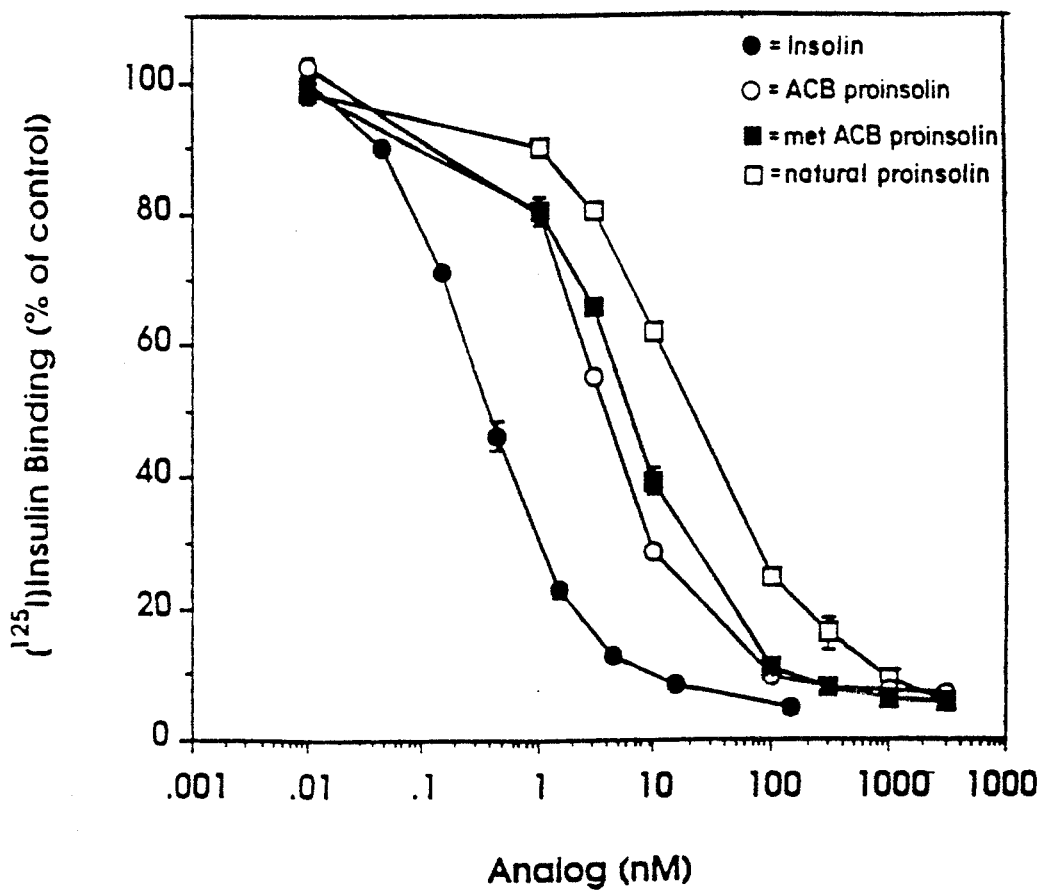
FIG. 23—Human placental insulin receptor binding assay results. The graph represents the competition of human insulin, human proinsulin, ACB-proinsulin, Met-ACB-proinsulin with $^{125}I$ insulin for binding to the insulin receptor.
Figure 24:
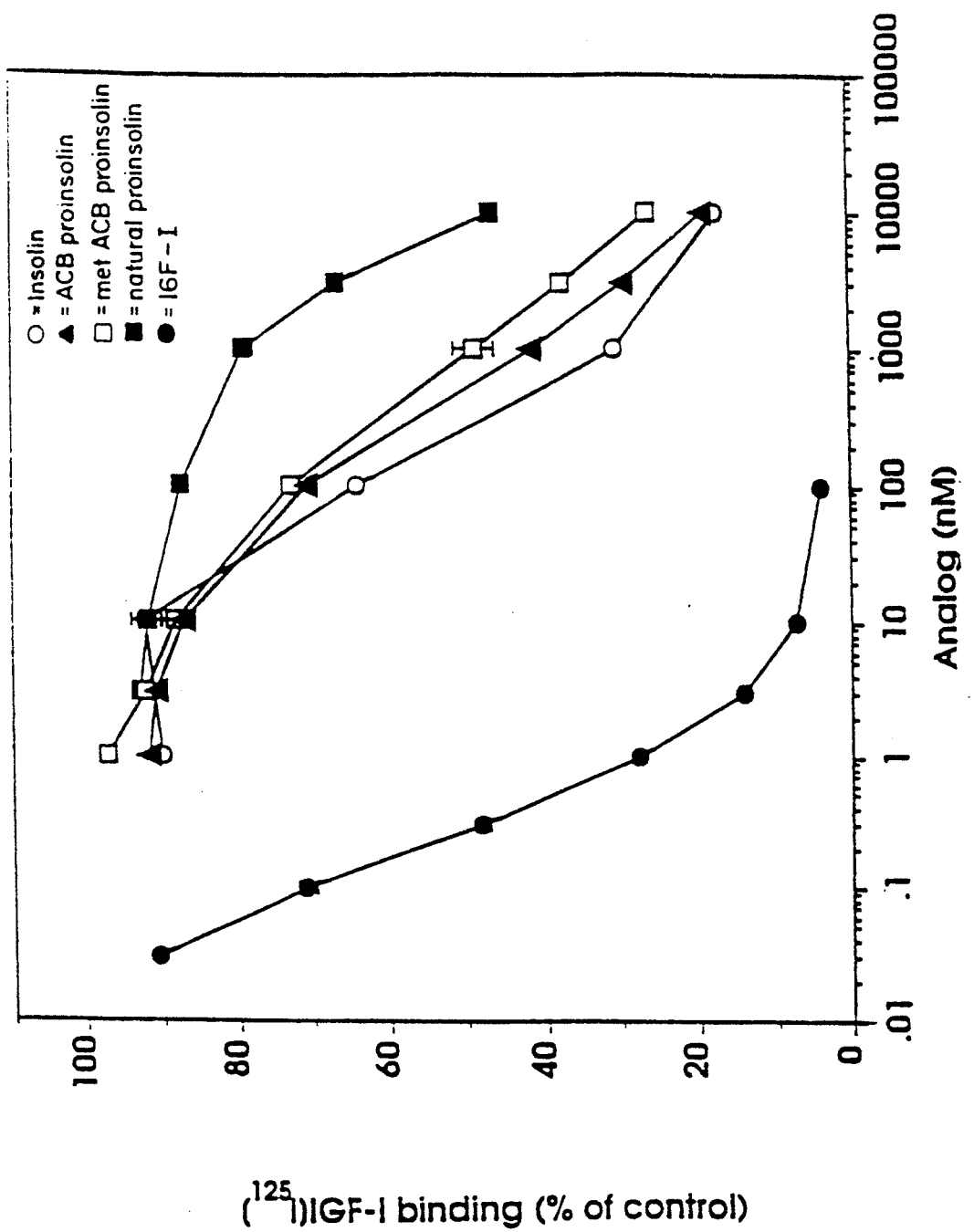
FIG. 24—Human placental IGF-I receptor binding. The graph represents the competition of human IGF-I, Met-ACB-proinsulin, ACB-proinsulin, human insulin and human proinsulin with $^{125}I$ IGF-I for binding to the IGF-I receptor.

The biological activities of the two inverted proinsulins were characterized in a number of in vitro and in vivo tests. In all cases, the inverted proinsulins demonstrated intermediate activity glucose uptake between that of insulin and proinsulin. When tested for their ability to compete with $^{125}$I insulin for binding to placental membrane insulin receptors, Met-ACB-proinsulin and ACB-proinsulin gave $ED_{50}$ values of 5.5 and 3.1 nM respectively as compared to insulin (0.45 nM) and proinsulin (20.4 nM) as shown in FIG. 23 and in Table II.

TABLE II

| | In Vitro Biological Activities of Inverted Proinsulin Analogs $ED_{50}$ (nM) | | |
|---|---|---|---|
| Analog | Insulin Receptor | IGF-I Receptor | Glucose Transport |
| Insulin | 0.45 | 328 | 0.043 |
| IGF-I | ND | 0.45 | ND |
| Proinsulin | 20.4 | 10000 | ND |
| ACB-Proinsulin | 3.1 | 520 | 0.83 |
| Met-ACB-Proinsulin | 5.5 | 940 | 2.5 |

ND = not determined

The ability of the ACB-proinsulins to stimulate glucose uptake by adipocytes was also measured and gave similar values for the potency of these two proteins versus insulin as shown in Table II. In contrast to their behavior at the insulin receptor, both molecules were far more similar to insulin than to proinsulin in the ability to stimulate DNA synthesis in human smooth muscle cells.

The inverted proinsulins were considerably more active in vivo than in vitro and showed the same prolonged duration of action as seen in Table III.

Experiments, the results of which are provided herein, demonstrate that human ACB-proinsulin was approximately 10% as potent as insulin in binding to the insulin receptor but had 65% of the potency of insulin in binding to the IGF-I receptor. Furthermore, the human ACB proinsulin molecule possesses approximately 30% of the insulin activity of native human insulin in vivo. The compounds compared in this study were insulin, proinsulin, ACE-proinsulin and Met-ACB-proinsulin. The inverted proinsulins, ACB-proinsulin and Met-ACB-proinsulin, demonstrated considerable increases in activity towards the insulin and IGF-I receptors in comparison to native proinsulin. The addition of a methionine to the glycine A-1 residue had a significant effect on the in vitro activity of Met-ACB-PI but only a minimal impact on its in activity.

The data presented in Table III were obtained in tests carried out in fasted, male, lean Sprague-Dawley rats (Charles River Laboratories).

TABLE III

| | In Vivo Hypoglycemic Effect of Insulin Analogs | | | | | |
|---|---|---|---|---|---|---|
| | Max. hypoglycemic effect (percent)[1] | | $ED_{50}$ (nM)[2] 1 hr. 2 hr. | | Relative biological action to insulin | |
| Substance | 1 hour | 2 hours | 1 hour | 2 hours | 1 hour | 2 hours |
| H-insulin | 59.0 ± 4.3 | 45.7 ± 6.7 | 1.0 ± 0.01 | 1.6 ± 0.09 | 100.0 | 100.0 |
| hPI | 55.1 ± 2.6 | 61.0 ± 4.0 | 91. ± 1.7 | 8.2 ± 0.8 | 14.3 ± 2.8 | 19.5 ± 1.8 |
| MetACBHPI | 54.4 ± 8.4 | 64.8 ± 3.8 | 8.4 ± 0.4 | 5.1 ± 0.0 | 15.4 ± 0.7 | 31.3 ± 0.0 |
| ACB-hPI | 60.5 ± 9.5 | 65.9 ± 9.5 | 3.3 ± 1.0 | 3.4 ± 0.8 | 39.6 ± 3.6 | 47.1 ± 10.6 |

[1]The maximum hypoglycemic effect is expressed as the percent change from zero time corrected for the control group in the same assay
[2]The $ED_{50}$ values represent the concentration of the protein that gave half the maximal hypoglycemic activity 1 or 2 hours after subcutaneous administration.
The values in this table are the mean ± S.E.M. for three seperate determinations with human insulins and two separate determinations for each of the proinsulins Human insulin produces a maximal hypoglycemic response 1 hour after subcutaneous administration and blood glucose levels returned to baseline by 3 to 4 hours. Human proinsulin and ACB-proinsulins produced maximal hypoglycemic effects 2 hours after s.c. administration and continued to provide a greater biological response over the remaining 3–4 hour period, the magnitude depending on the administered dose. In addition, the inverted proinsulins were found to be roughly 2-fold more potent than proinsulin in vivo with the ACB-proinsulin being more active than the Met-ACE-proinsulin compound as seen in Table III.

The instant invention provides a method for treating diabetes mellitus. The instant invention provides a method for non-insulin dependent diabetes mellitus. The method comprises administering to the organism an amount of ACB-proinsulin in a dose between about 10 and 1000 µg/kg. A preferred dose is from about 10 to 100 µg/kg of active compound. A typical daily dose for an adult human is from about 0.5 to 100 mg.

In practicing this method, compounds of the formula 1 can be administered in a single daily dose or in multiple doses per day. The treatment regime may require administration over extended periods of time. The amount per administered dose or the total amount administered will depend on such factors as the nature and severity of the disease, the age and general health of the patient and the tolerance of the patient to the compound.

A convenient method of practicing the treatment method is to administer the compounds of the formula 1 via intravenous infusion. In this procedure a sterile formulation of a suitable soluble salt of the compound is incorporated in a physiological fluid, such as 5% dextrose solution, and the resulting solution is infused slowly IV. Alternatively, the piggy-back method of IV infusion can also be used.

Compounds of the formula 1, i.e. ACB-proinsulins, are useful as a long-acting basal insulin replacements. The ACB-proinsulin and its analogs are of considerable therapeutic importance, particularly to the non-insulin dependent diabetes mellitus (NIDDM) patient in the regulation of glucose metabolism.

The instant invention further provides pharmaceutical formulations comprising compounds of the formula 1. The compounds, preferably in the form of a pharmaceutically acceptable salt, can be formulated for oral or parenteral administration for the therapeutic or prophylactic treatment of diabetes mellitus and/or non-insulin dependent diabetes mellitus (NIDDM).

For example, compounds of the formula 1 can be admixed with conventional pharmaceutical carriers and excipients and used in the form of tablets, capsules, elixirs, suspensions, syrups, wafers and the like. The compositions comprising ACB-proinsulin compounds will contain from about 0.1 to 90% by weight of the active compound, and more generally from about 10 to 30%. The compositions may contain common carriers and excipients such as corn starch or gelatin, lactose, sucrose, microcrystalline cellulose, kaolin, mannitol, dicalcium phosphate, sodium chloride, and alginic acid.

Disintegrators commonly used in the formulations of this invention include croscarmellose, microcrystalline cellulose, corn starch, sodium starch, glycolate and alginic acid.

Tablet binders that can be included are acacia, methyl cellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring, or the like can also be used.

It may be desirable to add a coloring agent to make the dosage form more attractive in appearance or to help identify the product.

For intravenous (IV) use, a water soluble form of compounds of the formula I can be dissolved in one of the commonly used intravenous fluids and administered by infusion. Such fluids, for example, physiological saline, Ringer's solution or 5% dextrose solution can be used.

For intramuscular preparations, a sterile formulation of a suitable soluble salt form of the compounds of the formula 1, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of ACB-proinsulin, for example, the hydrochloride salt, formulated in a diluent such as distilled or deionized water, is particularly useful.

Alternatively, the unit dosage form of the compound can be solution of the compound, preferably in its salt form, in a suitable diluent in sterile hermetically sealed ampoules. The concentration of the compound in the unit dosage may vary, e.g. from about 1% to about 50% depending on the particular form of the compound and its solubility and the dose desired by the physician.

The instant invention further provides a method for the recombinant production ACB-PI proteins or Met-ACB-PI proteins, said method comprising the steps of:
1. creating a synthetic gene, said gene comprising a DNA sequence encoding an ACB-PI peptide compound of the formula 1,
2. incorporating said gene into a suitable vector containing a promoter-operator region functional in a host cell,
3. orienting said gene in said vector so as to achieve transcription and translation of said synthetic gene and further that said gene is under the transcriptional control of said promoter-operator region,
4. transforming said host cell with said vector,
5. culturing said transformed host cell under conditions appropriate so as to induce transcription and translation of said gene, and
6. recovering and purifying said peptide compound.

Synthetic genes, the in vitro or in vivo transcription and translation of which will result in the production of the compounds of formula 1 may be constructed by techniques well known in the art. Owing to the natural degeneracy of the genetic code, the skilled artisan will recognize that a sizable yet definite number of DNA sequences may be constructed which encode the compounds of formula 1.

In the preferred practice of the invention as exemplified herein, the recombinant production a compound of the formula 1 was achieved using the synthetic gene comprising the DNA sequence:(Seq. ID No.2)

This DNA sequence encodes the compound of the formula 1 comprising the amino acid sequence: (Seq. ID No.1)

| Gly | Ile | Val | Glu | Gln | Cys | Cys | Thr | Ser |
|-----|-----|-----|-----|-----|-----|-----|-----|-----|
| Ile | Cys | Ser | Leu | Tyr | Gln | Leu | Glu | Asn |
| Tyr | Cys | Asn | Arg | Arg | Glu | Ala | Glu | Asp |
| Leu | Gln | Val | Gly | Gln | Val | Glu | Leu | Gly |
| Gly | Gly | Pro | Gly | Ala | Gly | Ser | Leu | Gln |
| Pro | Leu | Ala | Leu | Glu | Gly | Ser | Leu | Gln |
| Lys | Arg | Phe | Val | Asn | Gln | His | Leu | Cys |
| Gly | Ser | His | Leu | Val | Glu | Ala | Leu | Tyr |
| Leu | Val | Cys | Gly | Glu | Arg | Gly | Phe | Phe |
| Tyr | Thr | Pro | Lys | Thr | | | | |

The gene encoding the ACB-proinsulin molecule may be created by synthetic methodology. Such methodology of synthetic gene construction is well known in the art. Brown, E. L., Belagaje, R., Ryan, M. J., and Khorana, H. G. (1979) in *Methods in Enzymology,* Academic Press, N.Y., Vol. 68, pgs. 109-151, the entire teaching of which is hereby incorporated by reference. The DNA segments corresponding to the proinsulin gene of interest are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404). The synthetic ACB-PI gene may be designed to possess restriction endonuclease cleavage sites at either end of the transcript to facilitate isolation from and integration into expression and amplification plasmids. The choice of restriction sites are chosen so as to properly orient the ACB-PI coding sequence with control sequences to achieve proper in-frame reading and expression of the ACB-PI molecule. A variety of other such cleavage sites may be incorporated depending on the particular plasmid constructs employed and may be generated by techniques well known in the art. A schematic representation of this process is shown in FIG. 16.

The specific composite sequences illustrating the construction of the 278 base pair human ACB-PI molecule are Shown in FIG. 17. The preferred embodiment of the invention using the ACB-PI coding sequence is shown in FIG. 18 illustrating the positions of the engineered restriction endonuclease cleavage sites for EcoRI, HindIII, NdeI, and BamHI. The sequence shown in FIG. 18 corresponds to the preferred ACB-proinsulin coding sequences of human ACB-PI exemplified herein.

As exemplified herein, the ACB-HPI gene was created in two halves as shown in FIG. 16. One half of the gene was formed by mixing and ligating oligonucleotides 1, 2, 5, and 6. Whereas, the other half of the gene was formed by mixing and ligating oligonucleotides 3, 4, 7 and 8 as shown in FIG. 16. Both halves of the gene fragments were purified by 15% polyacrylamide gel electrophoresis. The DNA was recovered electrophoretically from the gel by slicing out the region of the gel corresponding to the ACB-PI gene halves and subjecting the slice to electrophoresis. The electrophoretically isolated DNA fragments were then desalted on a Sephadex G-50 column or its equivalent. The ACB-PI gene halves are then joined together to form the ACB-PI gene which was then integrated into an appropriate vector for amplification of the DNA.

Synthetic genes encoding the compounds of the formula 1 may be incorporated into vectors useful for cloning purposes. A variety of plasmids are available for this purpose and the techniques of integration and amplification and selection are well known in the art. Sambrook, J., Fritsch, E. F., Maniatis, T., *Molecular Cloning: A Laboratory Manual,* 2nd Ed., Vol.1, Cold Spring Harbor Press, (1989). The DNA sequence may also be amplified using the polymerase chain reaction as described in *Current Protocols in Molecule Biology* (1988 and, supplements) Wiley-Interscience, N.Y.

In the preferred embodiment of the invention, the pUC18 plasmid (commercially available from Boehringer-Mannheim Biochemicals, P. O. Box 50414, Indianapolis, Ind. 46250) is used for the DNA amplification phase. The choice of the pUC18 plasmid was interrelated to the presence of the BamHI and HindIII restriction endonuclease cleavage points in the multiple cloning site of pUC18. The choice of the amplification plasmid will determine the restriction endonuclease cleavage points which are engineered into the most distal positions of the ACB-PI coding sequence. The choice of the plasmid and the design of the synthetic ACB-PI gene go hand-in-hand because the amplification plasmid will determine the restriction sequences to be engineered into the ACB-PI sequence and correspondingly the sequences of the oligonucleotides used to construct the synthetic ACB-PI gene.

In one embodiment of the invention, approximately 5 μg of the pUC18 plasmid are suspended in 10 ml of the buffer appropriate to one of the particular restriction enzyme sites designed into the ACB-PI synthetic gene. In the preferred embodiment exemplified herein this restriction enzyme was HindIII. The pUC18 plasmid was accordingly suspended in 10 ml of HindIII buffer (1 M NaCl, 50 mM MgCl2, 100 mM tris-HCl, pH=8.0, 10 mM 2-mercaptoethanol). To this solution is added the equivalent of 20 units of the appropriate restriction enzyme. In the preferred embodiment of this invention this corresponds to 2 μl of HindII as obtained from Boehringer Mannheim Biochemicals, Indianapolis, Ind. 46250. The solution was diluted with 85ml of water, gently mixed and allowed to incubate at 37° C. for two hours. The reaction was quenched and the DNA precipitated using three volumes of ethanol, 0.3M in NaOAc. The pellet was centrifuged and dried.

The pellet is then resuspended in 10 μl of the restriction enzyme buffer appropriate to the other distal chosen restriction enzyme site of the ACB-PI gene. In the preferred embodiment of the invention as exemplified herein BamHI was this other restriction enzyme site. Accordingly, the pellet was resuspended in 10 μl of BamHI buffer (1M NaCl, 50 mM MgCl2, 100 mM tris-HC1, pH=8.0, 10 mM 2-mercaptoethanol). To this solution was added the equivalent of 20 units of the appropriate restriction endonuclease, preferably BamHI. BamHI HindIII, and a wide variety of other restriction endonucleases which may be used in this protocol are commercially available from supply houses such as Boehringer-Mannheim Biochemicals, P. O. Box 50414, Indianapolis, Ind. 46250. Next, 88 μl of water was added and the solution is gently mixed and incubated at 37° C. for two hours. The reaction was again quenched and the DNA precipitated with three volumes of ethanol, 0.3M in NaOAc. The DNA from the above digestion was electrophoresed on a 1% low melting agarose gel. The larger restriction fragment corresponding to the linearized vector DNA was sliced from the gel. The vector DNA was recovered by passing the gel slice through and Elutip-d ® column (commercially available from Schlicher & Schuell, Keene, N.H., U.S.A.) in substantial accordance with the manufacturer's instructions. The DNA was then precipitated as above and dried. The DNA was stored in 30 μl of 10 mm tris-HCl, pH=8.0.

Approximately 5 μl of the vector DNA was mixed with 10 picomoles of the synthetic DNA fragments, corresponding to the two halves of the ACB-PI synthetic gene, in 50 μl of ligation buffer (50 mM tris-HCl, pH 7.6, 100 mM MgCl2, 10 mM DTT (dithiothreitol), 800 mM ATP, and 3.5 units of T4 DNA ligase (commercially available from BoehringerMannheim Biochemicals, Indianapolis, Ind. 46250). The reaction was then incubated at 4° C. overnight and then transformed into frozen competent E. coli DH5α cells (commercially available from Bethesda Research Laboratories, Inc., P. O. Box 6009, Gaithersburg, Md. 20877) by techniques well known in the art and deliniated in standard laboratory manuals such as Sambrook, J., at al., supra. The transformants of the preferred embodiment of the invention were grown at 37° C. overnight x-gal TY agar plates containing 100 μg/ml ampicillin. The choice of antibiotic and media is dependent on the amplification vector and cell line employed.

Clones containing the correct insert were chosen by blue/white colony selection. The loss of functionality of the lacZ gene is attributed to the transformants, as the insertion point of the cloning region of pUC18 is within the lacZ coding sequence. The selection of the clones containing the proper sequence was confirmed by ds-DNA sequencing using a Sequenase ® kit (commercially available from United States Biochemical Corp., P. O. Box 22400, Cleveland, Ohio 44122) according to the protocol supplied by the manufacturer. The resulting plasmid of the preferred embodiment of the invention containing the human ACB-PI sequence was designated pRB181.

The strain developed carrying the amplification plasmid was then grown overnight at 37° C. in TY media containing 100 mg/ml of ampicillin and the plasmid containing the synthetic ACB-HPI coding sequence was isolated according to the teachings of Maniatis, T. Fritsch, E. F., and Sambrook, J., *Molecular Cloning: A Laboratory Manual*, Cold Spring Harbor Laboratory, New York (1982), pgs.89–94. Generally, approximately 20 μg of the plasmid DNA isolated as above is suspended in 20 μl of the buffer appropriate to one of the "inner" engineered-in restriction sites. The choice of these "inner" restriction sites is a function of the choice of the expression vector to be employed in relation to the control regions of the expression vector. In the preferred embodiment of the invention exemplified herein the restriction enzyme of choice was NdeI. To the above solution add approximately 40 units of the restriction enzyme, 175 μl of water and gently mix and incubate at 37° C. for one hour. Then add approximately 40 units of the other "inner" restriction endonuclease (in the preferred embodiment exemplified herein, BamHI) and incubate at 37° C. for another two hours. The reaction was then quenched and the DNA precipitated by three volumes of ethanol, 0.3m in NaOAc. The solution was then electrophoresed on a 1.2% low melting agarose gel. The fragment corresponding to the approximately 265 bp ACB-hPI coding sequence is then sliced from the gel. The ACB-hPI DNA was recovered by passing through an Elutip-d ® column as described in Example 2. After precipitation and drying in vacuo, the DNA was stored in 25 μl of 10 mM tris-HCl, pH 8.0.

The expression plasmid to be used, which may be selected from a number of alternatives, possesses an appropriate control region and appropriate restriction sites facilitating integration of the ACE-PI coding sequence operably with respect to the control regions. A variety of expression vectors useful for transforming procaryotic and transfecting eucaryotic cells are well known in the art. Examples of said expression vectors include pTrc 99A, pKK223-3, pKK223-2, pDR540 tac promoter vector, pDR trp promoter vector, pcz20, pLEBBGH2, and pL110C. In the most preferred practice of the invention as exemplified herein when the host cell is an E. coli K12 cell, the expression vector was pCZR126S. This plasmid may be prepared according to the teaching of Example 3 herein.

So as to achieve efficient transcription of the synthetic gene, said gene must be operably associated with a promoter operator region. A variety of promoter-operator regions functional in E. coli host cells are well known in the art. In the preferred practice of the invention as exemplified herein, said promoter-operator region is the lambda pL promoter operator region.

In the preferred practice of the the promoter-operator region of the synthetic gene encoding the compound of formula 1 placed in the same sequential orientation with respect to the ATG start codon of the synthetic gene as the promoter-operation occupies with respect to the ATG-start codon of the gene from which it was derived. Synthetic or modified promoter operator regions have been created and are well known in the art. When employing such synthetic or modified promoter-operator regions they should be oriented with respect to the ATG-start codon of the ACB-PI gene as directed by their creators.

In the preferred embodiment of the invention as provided herein, approximately 15 μg of the expression plasmid of choice (pCZR126S) is suspended in 20 μl of the buffer corresponding to the first of the two "inner" restriction sites of the ACB-PI coding sequence (in the manner exemplified herein the NdeI restriction site). To this add approximately 40 units of the restriction enzyme (for example NdeI), 175 μl of water, and incubate for two hours at 37° C. After the incubation, the DNA is precipitated in three volumes of ethanol, 0.3M in NaOAc as above, dried and resuspended in 20 μl of the restriction enzyme buffer corresponding to the second of the "inner" restriction site (in the manner exemplified herein, the BamHI restriction site). To this was added approximately 25 units of the second restriction enzyme (for example BamHI) and ~178 μl of water, gently mix, and incubate for a further two hours at 37° C. The reaction was again quenched and the DNA precipitated with three volumes of ethanol 0.3M in NaOAc. The pCZR126S vector DNA isolated in this manner was then electrophoresed on a 1% low melting agarose gel. The larger fragment corresponding to the vector DNA is then sliced from the gel and the vector DNA isolated by passing through an Elutip-d ® column. After precipitation and drying, the vector DNA is stored in 35 μl of 10 mM tris-HCl, pH 8.0.

Approximately 2.5 ml of the above vector DNA solution was then mixed with approximately 12 μl of the solution of the purified ACB-PI fragment prepared above. To this solution is added 4 μl of 10 0mM ATP, 0.5 μl of 1M dithiothreitol, 5 ml of 10X ligase buffer (500 mM tris-HCl, pH 7.6, 100 mM MgCl2), 26 μl of water and 0.5 μl (3.5 units) of T4 DNA ligase (commercially available from Pharmacia, Inc., 800 Centennial Avenue, Piscataway, N.J. 08854). The reaction is then incubated at 4° C. for 16 hours.

As exemplified herein, the ligation mixture was diluted with 50 μl of 10 mM tris-HCl (pH 7.6) and 3 μl of CaCl$_2$ and subsequently used to directly tranform competent *E. coli* K12 RV308 cells as provided in Example 3A herein. In the preferred embodiment of the invention *E. coli* K12 RV308 cells were employed as host cells but numerous other cell lines are available such as, but not limited to, *E. coli* K12 L201, L687, L693, L507, L640, L641, L695, L814 (*E. coli* B). The transformed host cells are then plated on appropriate media under the selective pressure of the antibiotic corresponding to the resistance gene present on the expression plasmid. The cultures are then incubated for a time and temperature appropriate to the host cell line employed.

The techniques of transforming cells with the aforementioned vectors are well known in the art and may be found in such general references as Maniatis, et al. (1988) *Molecular Cloning: A Laboratory Manual*, Cold Spring Harbor Press, Cold Spring Harbor Laboratory, Cold Spring Harbor, New York or *Current Protocols in Molecular Biology* (1989) and supplements. The methodology for transforming the *E. coli* cell lines employed in the most preferred practice of the invention may be obtained by reference to the Examples section herein. The precise conditions under which the transformed *E. coli* cells are cultured is dependent on the nature of the *E. coli* host cell line and the expression or cloning vectors employed. For example, vectors which incorporate thermoinducible promoter-operator regions, such as the cI857 thermoinducible lambda-phage promoter-operator region, require a temperature shift in the culture conditions so as to induce protein synthesis.

Proteins which are expressed in high-level bacterial expression systems characteristically aggregate in granules or inclusion bodies which contain high levels of the overexpressed protein. Kreuger, et al. (1990) in *Protein Folding*, Gierasch and King, eds., pgs 136–142, American Association for the Advancement of Science Publication No. 89-18S, Washington, D.C. Such protein aggregates must be solubilized to provide further purification and isolation of the desired protein product. Id. A variety of techniques using strongly denaturing solutions such as guanidinium-HCl and/or weakly denaturing solutions such as dithiothreitol (DTT) are used to solubilize the proteins. Gradual removal of the denaturing agents (often by dialysis) in a refolding solution allows the denatured protein to assume its native conformation. The particular conditions for denaturation and refolding are determined by the particular protein expression system and/or protein in question.

Examination of the ACB-proinsulin containing bacteria following fermentation indicated the presence of granule bodies. Following granule isolation, solubilization and sulfitolysis, the recombinant proteins were separated on an anion exchange column. Mono Q chromatography of the sulfitolyzed proteins followed by desalting by reverse phase HPLC yielded two ACB-proinsulin pools. Pool A (32 mg) gave a mass peak of 9878 by FAB-MS and amino terminal sequencing gave the sequence Gly-Ile-Val. Pool B (115 mg) gave a mass peak of 10009 by FAB-MS and showed an amino terminal sequence of Met-Gly-Ile. Coupled with amino acid analysis data, Pool A was deemed to represent the authentic ACB-proinsulin S-sulfonate while Pool B consisted of the ACB-proinsulin S-sulfonate molecule plus the initiator methionine residue corresponding to the initiation codon. RP-HPLC, amino acid analysis and N-terminal sequencing indicated that both protein pools were contaminated with the majority component of the other pool in addition to several other peaks.

Figure 21:
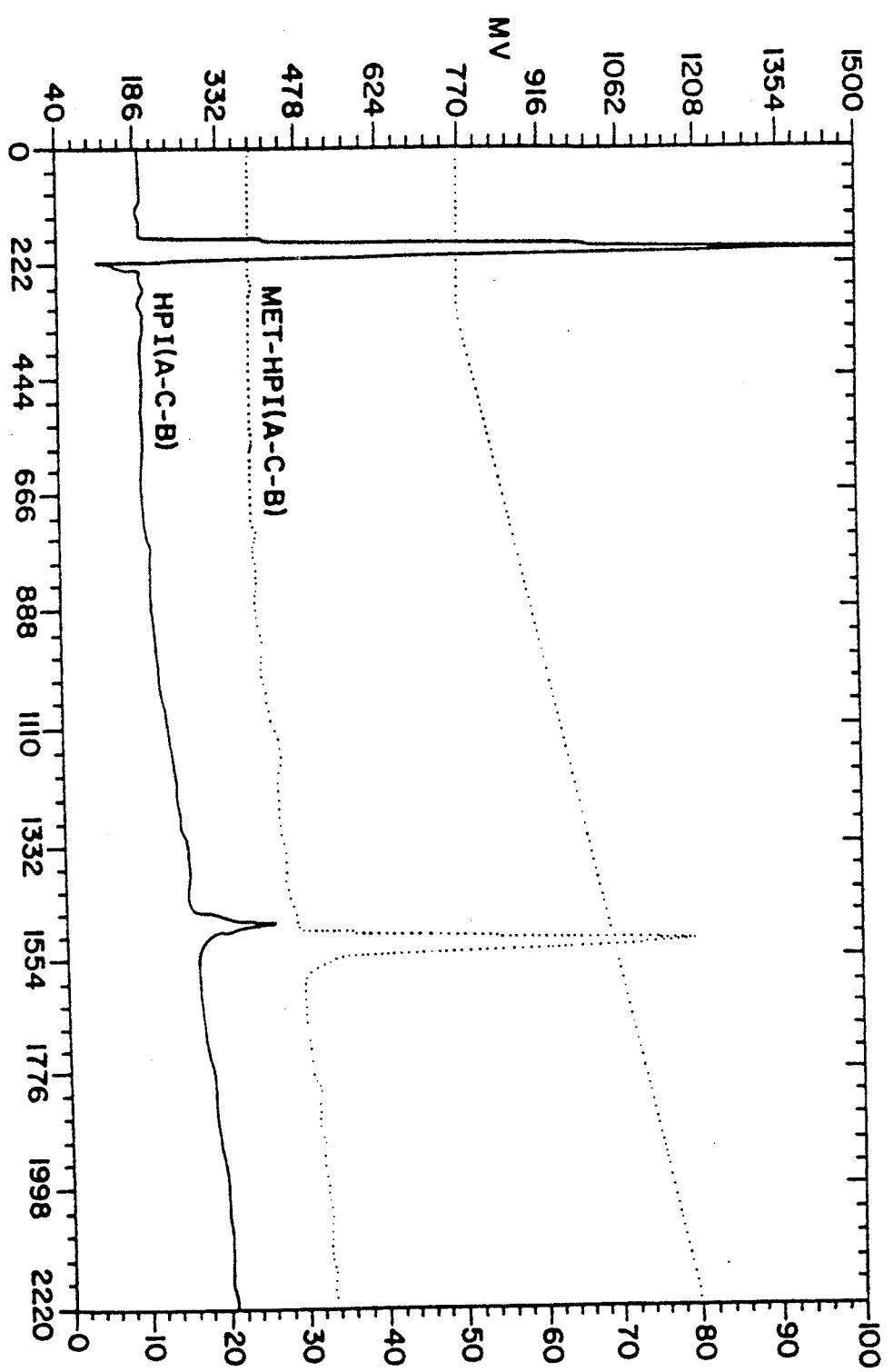
FIG. 21—Reverse-phase HPLC analysis of Met-ACB proinsulin and ACB-proinsulin. Chromatographic conditions are provided in the Examples.

The S-sulfonates of both ACB-proinsulin molecules were converted to the disulfide paired, folded ACB proinsulin molecules using a combination of high pH and added thiol in substantial accordance with the teaching of Frank, B. H., (1981) in *Peptides. Synthesis, Structure and Function. Proceedings of the Seventh American Peptide Symposium* (Rich, D. H. and Gross, E. Eds.) pgs. 729–738, Pierce Chemical Co., Rockford, Ill., the entire teaching of which is hereby incorporated by reference. Both molecules were folded in good yield (more than 75%) and were purified by reverse phase HPLC to give 33 mg of MetO-Glyl-ACB-proinsulin (2-86) (met-ACB-proinsulin) and 4 mg of Glyl-ACB-proinsulin (2-86) (ACE-proinsulin). The low yield of each analog was due to the need for conservative cuts in the pooling of the collected fractions from the purifications to minimize cross-contamination between the two inverted proinsulin forms. The proteins were characterized for purity and identity by RP-HPLC (FIG. 21), amino terminal sequencing, amino acid analysis, and FAB-MS with the expected results. In addition the Glyl-ACB proinsulin (2-86) molecule was analyzed for its disulfide bond pairing pattern.

The instant invention further provides a method for the recombinant production of native insulin proteins or insulin analogs, said method comprising the steps of:

1. creating a synthetic gene, said gene comprising a DNA sequence encoding a compound of the formula 1 wherein x=1,
2. incorporating said gene into a suitable vector containing a promoter-operator region functional in an *E. coli* host cell,
3. orienting said gene in said vector so as to achieve transcription and translation of said synthetic gene and further that said gene is under the transcriptional control of said promoter-operator region,
4. transforming an *E. coli* host cell with said vector,
5. culturing said transformed *E. coli* host cell under conditions appropriate so as to induce transcription and translation of said gene,
6. recovering and purifying the ACB-PI peptide,
7. cleaving said ACE-PI peptide with appropriate peptidases or chemical agents so as to excise said C-peptide.

The instant invention provides an entirely new pathway for the production of insulin using recombinant DNA technology. This invention demonstrates the use of an entirely new gene, mRNA, and proinsulin intermediates to produce a functional human insulin molecule together constituting a new recombinant biosynthetic pathway to insulin. The ACE-proinsulin molecule differs markedly in structure from native proinsulin (hereinafter termed "BCA-proinsulin" for purposes of comparison) yet may be effectively converted to yield a functional insulin molecule.

This novel pathway for the preparation of insulin is distinct from the current practice of replicating natural processes in diverse organisms. This alternate pathway to insulin results in significant savings in the recombinant production of commercially significant quantities of insulin by eliminating the requirement of removing the N-terminal methionine of the recombinant molecule with cathepsin C, or other methods, relying instead on the intrinsic action of the methionyl amino peptidase of the *E. coli* host cell to remove the N-terminal methionine.

Since the removal of the N-terminal methionine residue of ACB-PI is dependent on the presence of MAP, the host cell chosen must intrisically produce MAP or have been engineered to produce MAP. The MAP protease is indigenous to *E. coli* cells. Thus, a variety of *E. coli* cell lines which are not deficient in the production of the MAP may be employed in the practice of the method of the instant invention. Examples of *E. coli* host cells useful in the practice of the instant invention include the cell lines *E. coli* K12 L201, L687, L693, L507, L640, L641, L695, L814 (*E. coli* B). In the pre erred practice of the invention said *E. coli* host cell is the *E. coli* K12 RV308 *E. coli* cell line.

The conversion of the single-chain ACB-PI molecule to a functional native insulin or insulin analog requires the excision of the interal C-peptide. This may be achieved by enzymatic or chemical means such as cyanogen bromide cleavage. When the native human proinsulin A-chain, B-chain and C-peptide amino acid sequences are employed in the ACB-hPI peptide's construction as exemplified herein, the amino acid sequence of the ACB-hPI peptide is:

```
Gly  Ile  Val  Glu  Gln  Cys  Cys  Thr  Ser  Ile
A1   A2   A4   A4   A5   A6   A7   A8   A9   A10

Cys  Ser  Leu  Tyr  Gln  Leu  Glu  Asn  Tyr  Cys
A11  A12  A13  A14  A15  A16  A17  A18  A19  A20

Asn  Arg  Arg  Glu  Ala  Glu  Asp  Leu  Gln  Val
A21  C1   C2   C3   C4   C5   C6   C7   C8   C9

Gly  Gln  Val  Glu  Leu  Gly  Gly  Gly  Pro  Gly
C10  C11  C12  C13  C14  C15  C16  C17  C18  C19

Ala  Gly  Ser  Leu  Gln  Pro  Leu  Ala  Leu  Glu
C20  C21  C22  C23  C24  C25  C26  C27  C28  C29

Gly  Ser  Leu  Gln  Lys  Arg  Phe  Val  Asn  Gln
C30  C31  C32  C33  C34  C35  B1   12   B3   B4

His  Leu  Cys  Gly  Ser  His  Leu  Val  Glu  Ala
B5   B6   B7   B8   B9   B10  B11  B12  B13  B14

Leu  Tyr  Leu  Val  Cys  Gly  Glu  Arg  Gly  Phe
B15  B16  B17  B18  B19  B20  B21  B22  B23  B24

Phe  Tyr  Thr  Pro  Lys  Thr
B25  B26  B27  B28  B29  B30
```

The following diagram will serve to illustrate the trypsin enzymatic processing pattern of ACB-PI used in the conversion of ACB-PI to insulin.

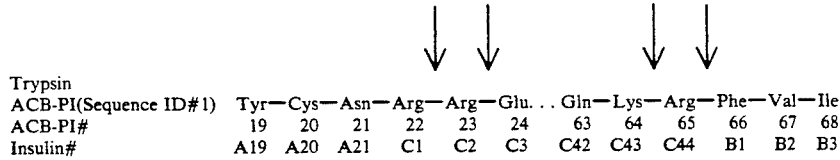

| | | | | | | | | | | | |
|---|---|---|---|---|---|---|---|---|---|---|---|
| Trypsin | | | | | | | | | | | |
| ACB-PI(Sequence ID#1) | Tyr | Cys | Asn | Arg | Arg | Glu... | Gln | Lys | Arg | Phe | Val | Ile |
| ACB-PI# | 19 | 20 | 21 | 22 | 23 | 24 | 63 | 64 | 65 | 66 | 67 | 68 |
| Insulin# | A19 | A20 | A21 | C1 | C2 | C3 | C42 | C43 | C44 | B1 | B2 | B3 |

Since trypsin will cleave on the carboxy side of Arg21, Arg22, Lys64 and Arg65, a mixture of insulin protein species results from the tryptic digestion of ACB-PI. These include:

Arg$_{A22}$, Arg$_{A23}$, Arg$_{B-1}$ insulin
Arg$_{A22}$, Arg$_{B-1}$ insulin
Arg$_{A22}$, Arg$_{A23}$ insulin
Arg$_{A22}$ insulin Subsequent digestion of the above species with carboxypeptidase B will remove the arginine residues from the carboxyterminus of the A-chain resulting in the following species being produced Arg$_{B-1}$ insulin
native insulin Thus one may produce native mature human insulin by proteolytic cleavage of the ACB-hPI intermediate. The N-terminal methionine residue of the ACB-PI molecule is intrinisically removed with approximately 30% efficiency by the indigenous action of methionyl amino peptidase (MAP) in the host cell.

Figure 25:
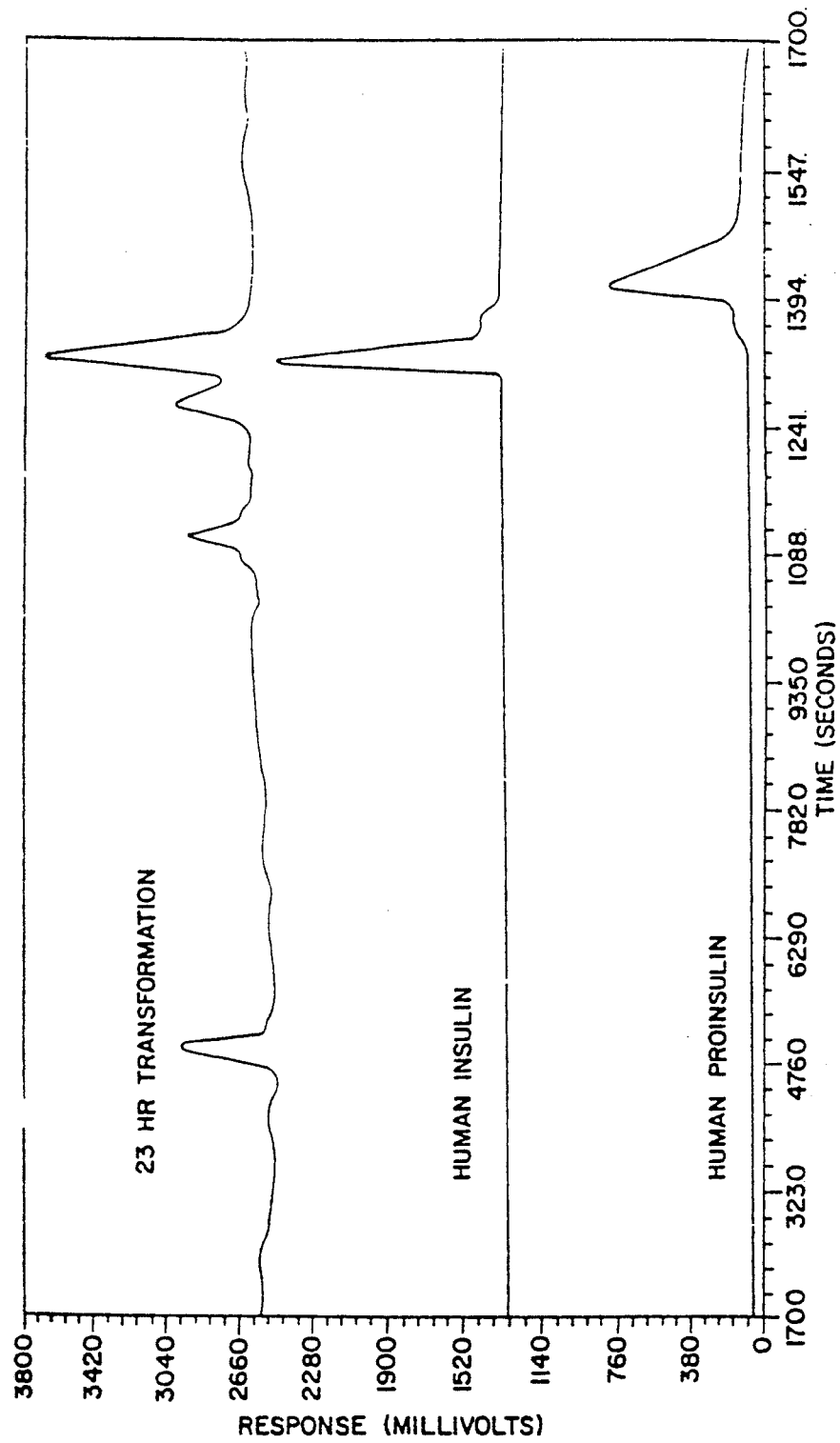
FIG. 25—HPLC analysis of the proteolytic transformation of ACB-proinsulin to insulin. The chromatograms displayed are (a) reaction after 24 hours, (b) biosynthetic human insulin, and (c) biosynthetic human proinsulin. Chromatography conditions are provided in the Examples.
Figure 26:
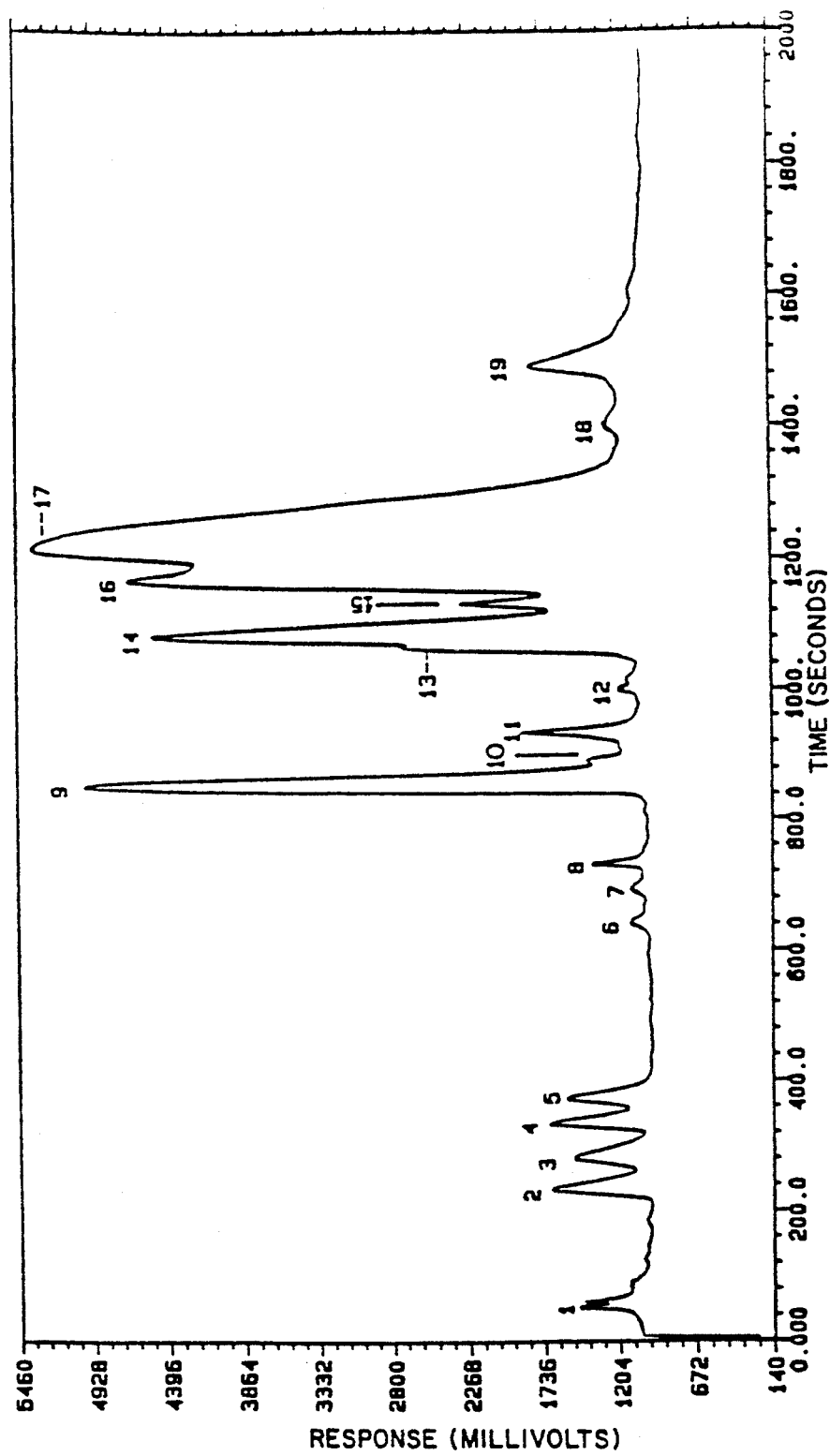
FIG. 26—Preparative HPLC chromatography of proinsulin conversion reaction.

ACB-proinsulin was converted to human insulin by the use of trypsin and carboxypeptidase B as has been used for normal proinsulin as disclosed by Kemmler, W., et al., (1971) *J. Biol. Chem.*, Vol. 246, pgs. 6786–6791, the entire teaching of which is hereby incorporated by reference. Conversion of ACB-proinsulin to insulin required substantially more vigorous conditions than did the corresponding transformation of proinsulin. The reaction was followed on RP-HPLC as shown in FIG. 25 and showed a total loss of the starting material along with the appearance of several new protein peaks. Following enzyme digestion, the resulting peptide mixture was separated into its component parts using RP-HPLC as shown in FIG. 26, various fractions collected and analyzed as shown in Table IV.

TABLE IV

Analysis of Peptides from Proteolytic Transformation of ACB-Proinsulin to Insulin

| Peak # | Identity | FAB/MS | AAA[a] | HPLC | Fingerprint |
|---|---|---|---|---|---|
| 2 + 4 | B22 30 | ND | Yes | ND | ND |
| 3 + 5 | B22 29 | ND | Yes | ND | ND |
| 9 | C-peptide | 3020.3 | ND | Yes | ND |
| 14 | DOP-InsulinC | 4866.4 | Yes | ND | ND |
| 16 | Arg-Insulin | 5964.8 | Yes | ND | ND |
| 17 | Insulin | 5808.5 | ND | Yes | Yes |
| 17 | des-Thr-Insulin | 5707.3 | ND | ND | Yes |

Figure 27:
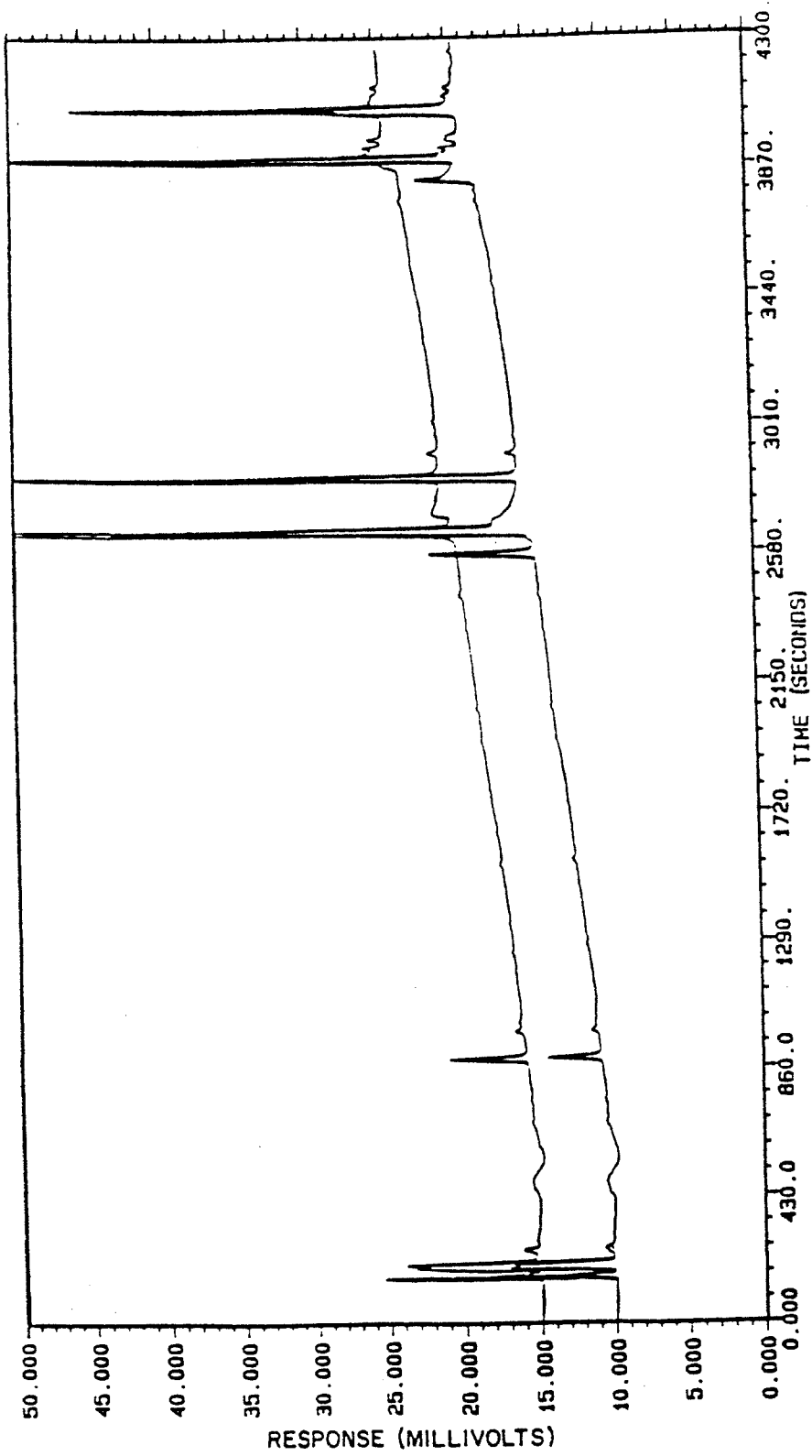
FIG. 27—Peptide map of insulin from conversion reaction.
Figure 28:
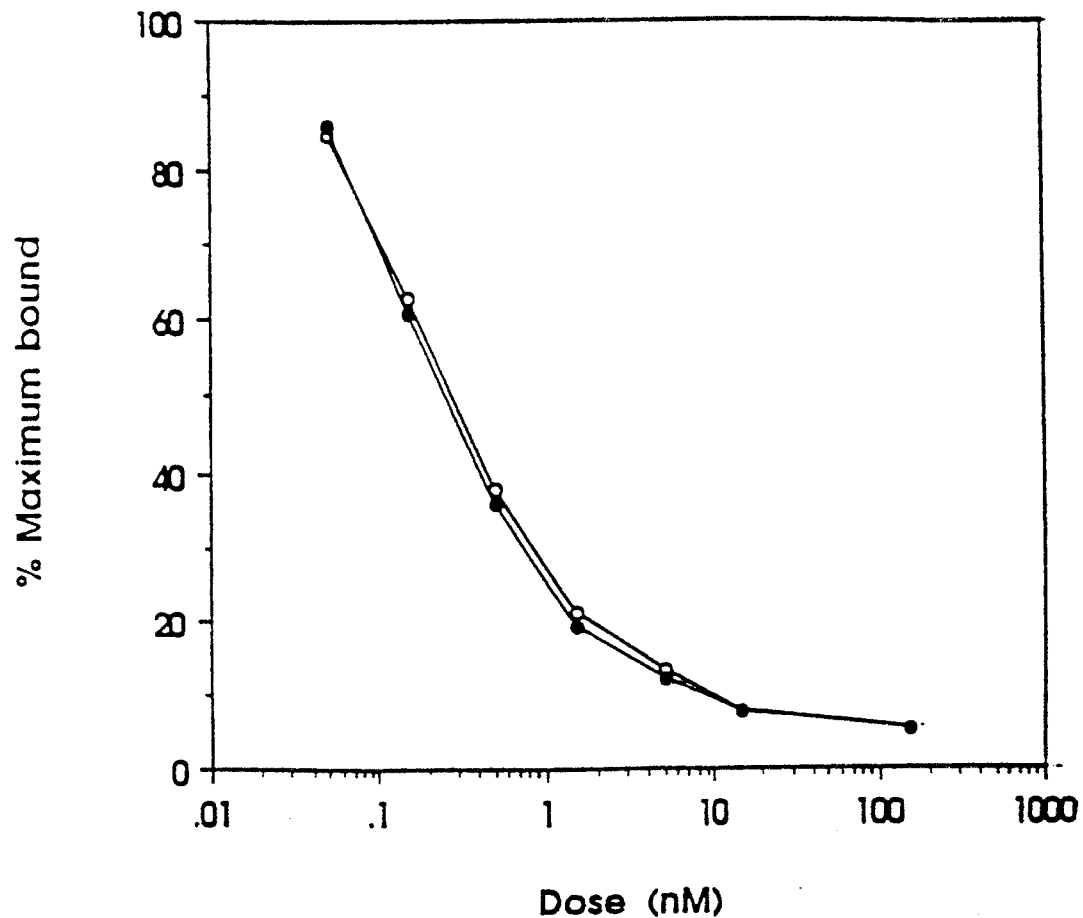
FIG. 28—Human placental insulin receptor binding. Competition with $^{125}I$ insulin of human insulin and human insulin prepared from ACB-proinsulin for binding to the human insulin receptor.
Figure 29:
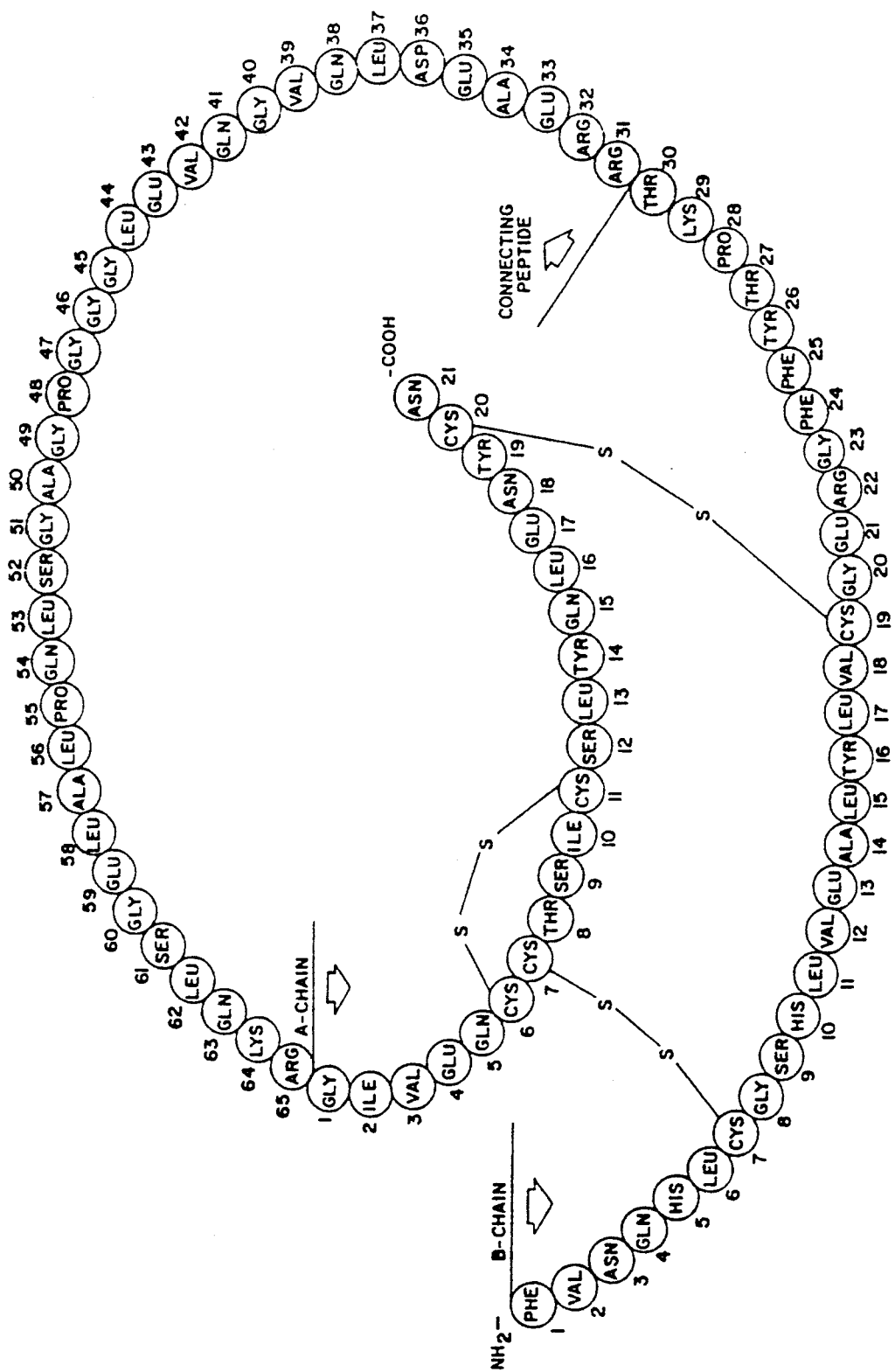
FIG. 29A—Is a diagram illustrating the primary structure of the naturally occuring BCA proinsulin molecule.
FIG. 29B—Is a diagram illustrating the primary structure of the ACB proinsulin molecule.
Figure 29:
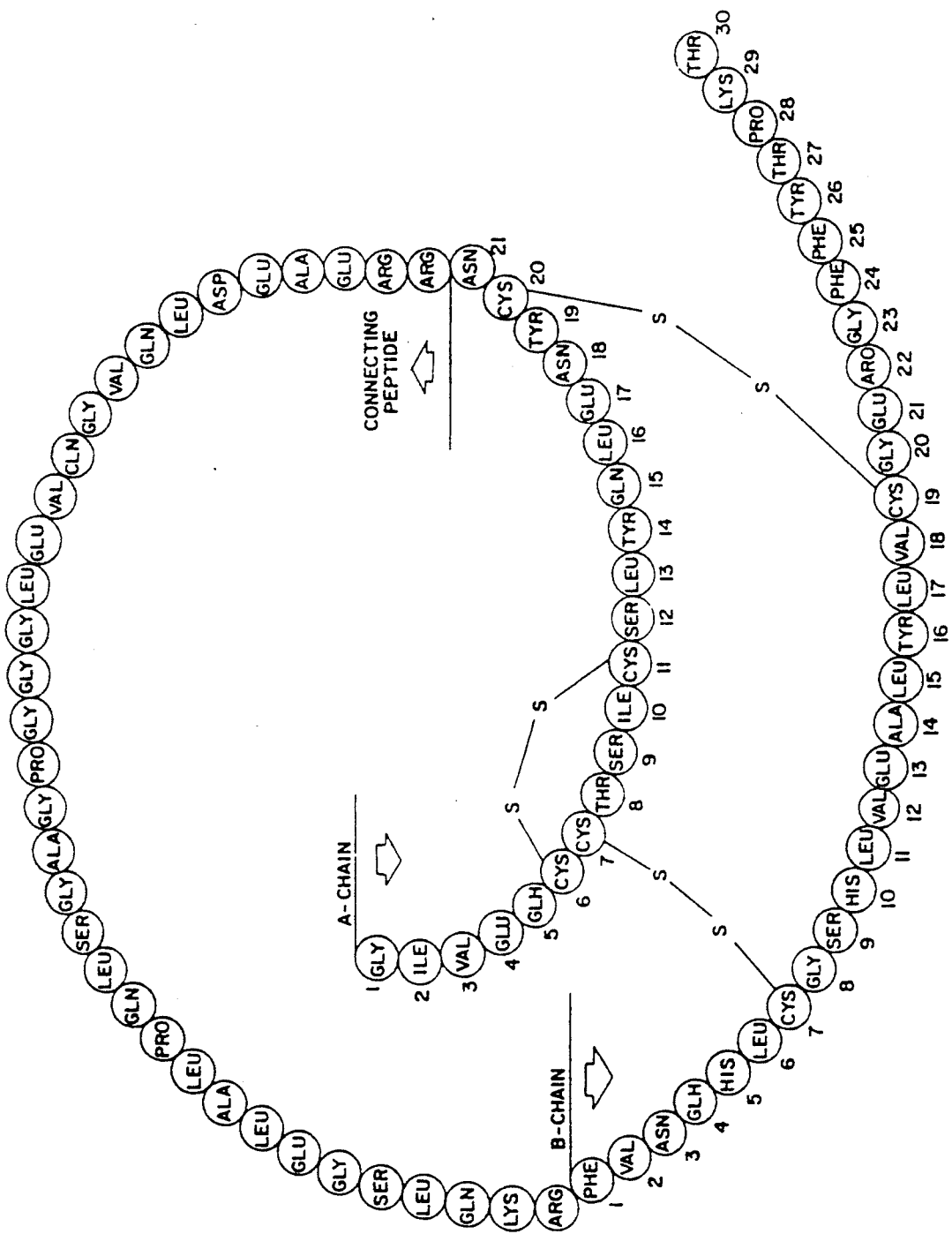

ND = not determined
[a]Amino acid analysis
[b]V8 protease peptide mapping [c]deS— (B22$^{-30}$-inSulin
[d]des-Thr$^{B30}$-insulin Peaks 2+4 and 3+5 of FIG. 26 were identified as (Sequence ID #14) GFFYTPK=Gly-Phe-Phe-Tyr-Thr-Pro-Lys (B$^{23-29}$) and (Sequence ID #15) GFFYTPKT=Gly-Phe-Phe-Tyr-Thr-Pro-Lys-Thr (B$^{23-30}$), presumably the result of cleavage by trypsin at the Arg-22 of the B-Chain of insulin (Table IV) and ran as doublets due to the necessity to make two separate sample injections onto the column. Peak 9 (FIG. 26)

was identified as the C-peptide based on co-elution with a C-peptide standard and molecular mass determination by FAB-MS (Table IV). Peak 14 (FIG. 26) corresponded to the des-octapeptide (B23-30) insulin, the other product of the reaction which yielded peaks 2 and 3. Peak 16 was identified as mono-Arg-insulin, presumably mono-Arg(A22)-insulin based on FAB-MS and amino acid analysis (Table IV). The major peak isolated from the transformation was fraction 17 (133 µg). This protein peak co-eluted with authentic biosynthetic human insulin using RP-HPLC as shown in FIG. 27. When analyzed by FAB-MS, it gave a molecular mass peak of 5808.5 as expected for human insulin. In addition, a smaller peak of molecular mass 5707.3 representing 10-15% of the total protein and identified as des-Thr(B30) insulin was observed. Des-Thr (B30) insulin is known to co-chromatograph with human insulin under the RP-HPLC system used so the failure to separate this material from insulin is not unexpected. Peak 17 was also analyzed by *Staphylococcus aureus* V8 protease peptide mapping according to the teaching of Chance, R. E., et al., (1981) in *Peptides. Synthesis, Structure, and Function. Proceedings of the Seventh American Peptide Symposium*, (Rich, D. H. and Gross, E. eds) pgs. 721-728, Pierce Chemical Company, Rockford, Ill., the entire teaching of which is hereby incorporated by reference, and found to be identical to biosynthetic human insulin with the exception that a small peak representing (Sequence ID #14) (GFFYTPK) Gly-Phe-Phe-Tyr-Thr-Pro-Lys (from des-Thr(B30) insulin) was observed in addition to the normal (Sequence ID #15) (GFFYTPKT) Gly-Phe-Phe-Tyr-Thr-Pro-Lys-Thr peak as shown in FIG. 27. As shown in FIG. 30, the insulin produced by the proteolytic transformation of ACB-insulin was 100% biologically active in the human placental insulin receptor assay.

Figure 22:
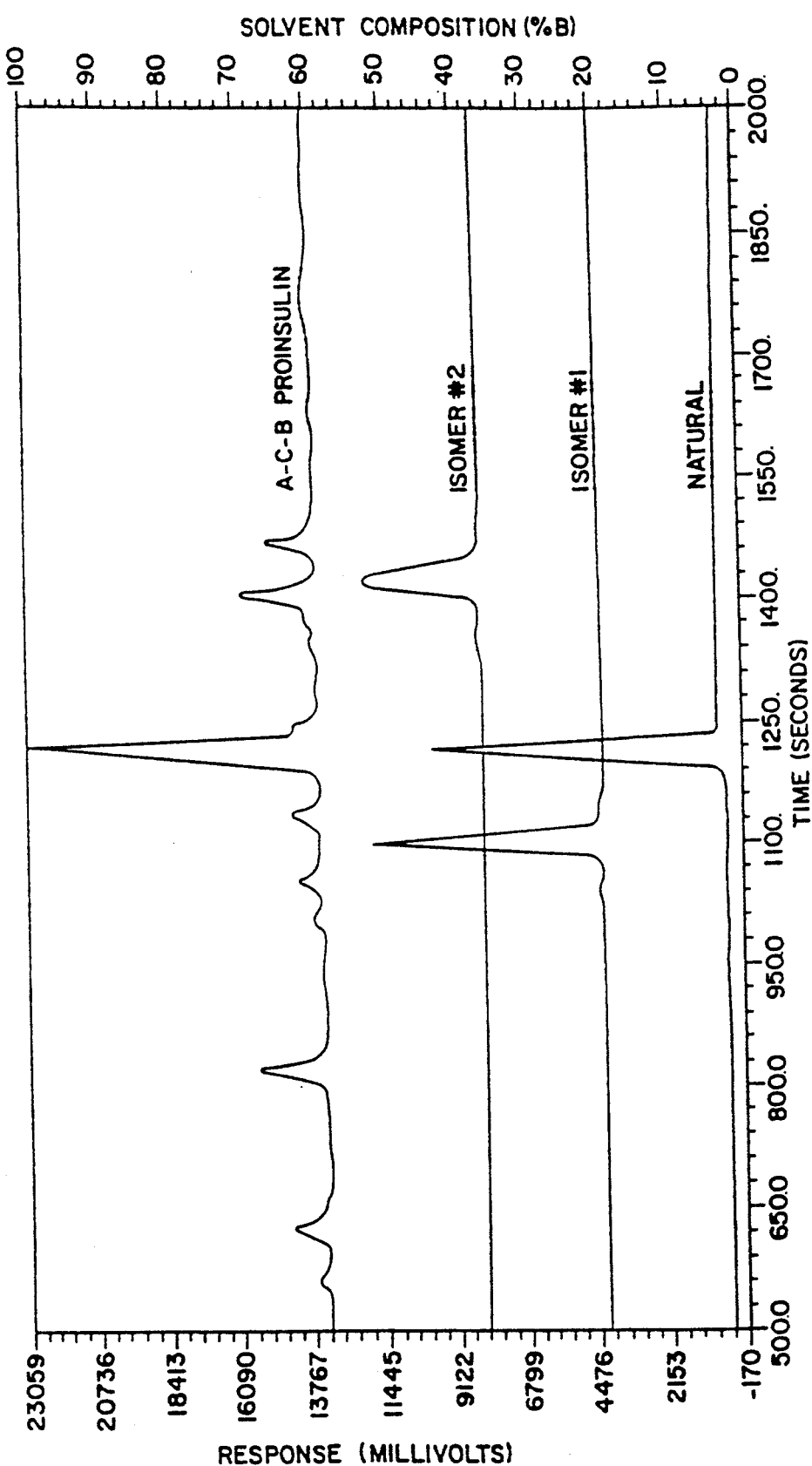
FIG. 22—Peptide mapping of ACB-proinsulin after trypsin/pepsin digestion. The chromatogram shows the resulting peptides along with the elution positions of the three possible disulfide isomer peptides.

To further determine whether or not the protein produced via enzymatic digest of ACB-proinsulin species exemplified herein corresponded to native human insulin, the trypsin+pepsin digestion pattern of the ACB-preinsulin produced protein was compared to the the trypsin+pepsin digestion pattern of human insulin. A thorough trypsin+pepsin digest of human insulin yields a stable A1-13/B1-11 fragment plus numerous other minor fragments as disclosed by Toren, P., et al., (1988) *Anal, Biochem.*, Vol. 169, pgs. 287-299. Of the 12 possible insulin disulfide isomers containing a single A and B Chain, only three can yield free and separate A1-13/B1-11 fragments when digested by pepsin, namely, the natural hormone and the two disulfide isomers chemically synthesized earlier as disclosed in Sieber, P., et al., (1978) Hoppe-Seylor's *Z, Physiol.* *Chem.*, Vol. 359, pgs. 113-123. The A1-13/B1-11 fragment was obtained from a trypsin/pepsin digest of the ACB-proinsulin and was compared to the A1-13/B1-11 fragments obtained from these three insulin isomers. The completed pepsin digest showed that the major HPLC peak co-eluted with the A1-13/B1-11 fragment from natural insulin and that it did not contain any peaks matching the A1-13/B1-11 fragments from the two disulfide isomers as shown in FIG. 22. The major digest peak was purified (53 µg) and was found to have the expected amino acid composition for A1-13/31-11.

The following Examples are provided to further illustrate the invention but are not intended to be limitations thereof.

EXAMPLE 1

Construction of the Synthetic ACB-Proinsulin Gene

A 278 base pair DNA fragment which encodes the human ACB-proinsulin gene was designed on the basis of the well known amino acid sequence of the human proinsulin molecule and comprises the sequence: (Positive Strand = Seq ID No. 2, Negative Strand = Seq ID No. 3)

```
5' - AGCTTCATATGGGCATTGTGGAACAATGCTGTACCAGCATCTGCTCCCTG
3' - AGTATACCCGTAACACCTTGTTACGACATGGTCGTAGACGAGGGAC

TACCAGCTGGAGAACTACTGCAACCGCCGTGAGGCAGAGGACCTGCAGGTG
ATGGTCGACCTCTTGATGACGTTGGCGGCACTCCGTCTCCTGGACGTCCAC

GGTCAGGTGGAGCTGGGCGGTGGCCCGGGTGCAGGCAGCCTGCAGCCGCTG
CCAGTCCACCTCGACCCGCCACCGGGCCCACGTCCGTCGGACGTCGGCGAC

GCCCTGGAGGGTTCCCTGCAGAAGCGTTTTTTGAACCAACACCTGTGCGGC
CGGGACCTCCCAAGGGACGTCTTCGCAAAAAACTTGGTTGTGGACACGCCG

TCCCACCTGGTGGAAGCTCTGTACCTGGTGTGCGGTGAACGTGGCTTCTTC
AGGGTGGACCACCTTCGAGACATGGACCACACGCCACTTGCACCGAAGAAG

TACACCCCGAAGACCTAGGATCCG - 3'
ATGTGGGGCTTCTGGATCCTAGGCTTAA - 5'
```

The nucleotide sequences were modified at their 5' and 3' ends by the addition of bases to create NdeI and BamHI restriction sites flanked by HindIII and ECoRI sites for cloning the gene into the polylinker region of the pUC18 plasmid. Eight synthetic oligonucleotides (regions 1-8 in the above diagram) varying in length from 56 bases to 74 bases as shown above were generated using an Applied Biosystems Model 380A or 380B DNA synthesizer (commercially available from Applied Biosystems, 850 Lincoln Center Drive, Foster City, Calif. 94404), according to the manufacturer's recommended procedures and purified by electrophoresis on a 15% polyacryamide gel. These oligonucleotides were phosphorylated with [gamma-p32]ATP and polynucleotide kinase and then assembled with T4 DNA ligase to form two, 139 base pair long DNA duplexes according to the teachings of Brown, E. L., Belagaje, R., Ryan, M. J., and Khorana, H. G. (1979) in *Methods in Enzymology*, Academic Press, N.Y., 68, pgs. 109-151, the entire teaching of which is hereby incorporated by reference.

The first half of the ACB-PI gene was formed by mixing unphosphorylated oligonucleotide 1 with phosphorylated oligonucleotides 2, 5, and 6 whereas the second half of the gene was formed by mixing phosphorylated oligonucletides 3, 4, and 7 with unphosphorylated oligonucleotide 8. Both halves of the gene fragments were purified on a 15% polyacrylamide gel and the DNA was recovered from the gel slice electrophoretically followed by desalting on a Sephadex G-50 Column.

EXAMPLE 2

Construction of Plasmid pRB 181

About 5 μg of plasmid pUC18 (commercially available from Boehringer-Mannheim) was suspended in 10 μl of 10X HindIII buffer (1M NaCl, 50 mM $MgCl_2$, 100 mM tris-HCl, pH=8.0, 10 mM 2-mercaptoethanol), 2 μl of HindIII restriction endonuclease (Boehringer-Mannheim, 20 units), 85 μl of water, gently mixed and incubated at 37° C. for two hours. The DNA was precipitated with three volumes of ethanol, 0.3M in NaOAc. After centrifugation and drying in vacuo, the pellet was redissolved in 10 μl of 10X BamHI buffer (1M NaCl, 50 mM $MgCl_2$, 100 mM Tris-HCl, 10 mM 2-mercaptoethanol, pH=8.0), 2 μl of BamHI restriction enzyme (Boehringer-Mannheim 20 units), 88 μl of water, gently mixed and incubated at 37° C. for another 2 hours. The DNA was again precipitated with three volumes of ethanol and 0.3M NaOAc and electrophoresed on a 1% low melting agarose gel. The larger HindIII/BamHI restriction fragment (265 bp) was sliced from the gel and the DNA was recovered by passing through an elutip-d column (commercially available from Schlicher & Schuell, Keene, N.H. 03431) according to the procedure recommended by the vendor. After precipitation and drying the DNA was stored in 30 ml of 10 mM tris-HCl pH=8.0 at 4° C.

About 5 μl of this vector DNA was mixed with 10 picomoles of the two synthetic DNA fragments as prepared above in 50 μl of ligation buffer (50 mM tris-HCl, 10 mM $MgCl_2$, 10 mM DTT, 800 uM ATP, and 3.5 units of T4 DNA ligase, pH=7.6). The reaction was incubated at 4° C. overnight and then transformed into frozen competent *E. coli* DH5 cells (commercially available from Bethesda Research Laboratories, P. O. Box 6009, Gaithersburg, Md. 20877). The transformants were grown at 37° C. overnight on x-gal TY agar plates containing 100 μg/ml of ampicillin. Clones containing the correct insert were chosen by the loss of a functional lacZ gene as screened by the blue/white colony selection and confirmed with ds-DNA sequencing using the Sequenase kit (commercially available from United States Biochemical Corp.). The resulting plasmid was designated pRB181.

EXAMPLE 3

Construction of Recombinant Vectors and Hosts

A. Construction of Plasmid pCZR126S

1. Isolation of Plasmid pKC283

Lyophils of *E. coli* K12 BE1201/pKC283 are obtained from the Northern Regional Research Laboratory, Peoria, Ill. 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 μg/ml in ampicillin and then incubated at 32° C. overnight. The *E. coli* K12 BE1201/pKC283 cells were cultured at 32° C., because the cells comprise a temperature-sensitive cI repressor gene integrated into the cellular DNA. When cells that comprise a wild-type lambda pL repressor gene or do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 mg/ml ampicillin in a manner so as to obtain a single colony isolate of *E. coli* K12 BE1201/pKC283. The single colony obtained was inoculated into 10 ml of LB medium containing 50 μg/ml ampicillin and incubated overnight at 32° C. with vigorous shaking. The 10 ml overnight culture was inoculated into 500 ml LB medium containing 50 μg/ml ampicillin and incubated at 32° C. with vigorous shaking until the culture reached stationary phase.

The following procedure is adapted from Maniatis et al., 1982, Molecular Cloning (Cold Spring Harbor Laboratory). The cells were harvested by centrifugation at 4000 g for 10 minutes at 4° C., and the supernatant was discarded. The cell pellet was washed in 100 ml of ice-cold STE buffer (0.1 M NaCl; 10 mM Tris-HCl, pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2N NaOH and 1% SDS) were then added to the lysozyme-treated cells, and the solution was gently mixed by inversion. The mixture was incubated on ice for 10 minutes.

Fifteen ml of ice-cold 5 m potassium acetate, pH 4.8, were added to the lysed-cell mixture and the solution mixed by inversion. The solution was incubated on ice for 10 minutes. The 5 M potassium acetate solution was prepared by adding 11.5 ml of glacial acetic acid to 28.5 ml of water and 60 ml of 5M potassium acetate; the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentration was about 600 μg/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pKC283 was obtained and stored at 4° C. in TE buffer at a concentration of about 1 μg/μl. A restriction site and function map of plasmid pKC283 is presented in FIG. 1 of the accompanying drawings.

EXAMPLE 3.A.2

Construction of Plasmid pKC283PX

About 10 μl of the plasmid pKC283 DNA prepared in Example 1 were mixed with 20 μl 10 X medium-salt restriction buffer (500 mM NaCl; 100 mM Tris-HCl, pH 7.5; 100 mM $MgCl_2$; and 10 mM DTT), 20 μl 1 mg/ml BSA, 5 μl restriction enzyme PvuII (~50 Units, as defined by Bethesda Research Laboratories (BRL), from which all restriction enzymes used herein were obtained), and 145 μl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 ml of TE buffer.

About 600 picomoles (pM) of XhoI linkers (5'-CCTCGAGG-3')(Sequence Id No.4) were kinased in a mixture containing 10 μl 5 X Kinase Buffer (300 nm Tris-HCl, pH 7.8; 50 mM $MgCl_2$; and 25 mM DTT), 5 μl 5 mM ATP, 24 μl $H_2O$, 0.5 μl of T4 polynucleotide kinase (about 2.5 units as defined by P-L Biochemicals), 5 μl 1 mg/ml BSA, and 5 μl of 10 mM spermidine by incubating the mixture at 37° C. for 30 minutes.

About 12.5 μl of the kinased XhoI linkers were added to the 5 μl of PvuII-digested plasmid pKC283 DNA, and then 2.5 μl of 10 X ligase buffer (300 mM Tris-HCl, pH 7.6; 100 mM $MgCl_2$; and 50 mM DTT) , 2.5 μl of 1 mg/ml BSA, 7 μl of 5 mM ATP, 2.5 μl (about 2.5 units as defined by P-L Biochemicals) of T4 DNA ligase, 2.5 μl of 10 mM spermidine, and 3 ml of water were added to the DNA. The resulting ligation reaction was incubated at 4° C. overnight. After the ligation reaction, the reaction mixture was adjusted to have the composition of high-salt buffer (0.1M NaCl; 0.05 M Tris-HCl, pH 7.5; 10.0 mM $MgCl_2$; and 1 mM DTT). About 10 μl (100 units) of restriction enzyme XhoI were added to the mixture, and the resulting reaction was incubated at 37° C. for 2 hours.

Figure 2:
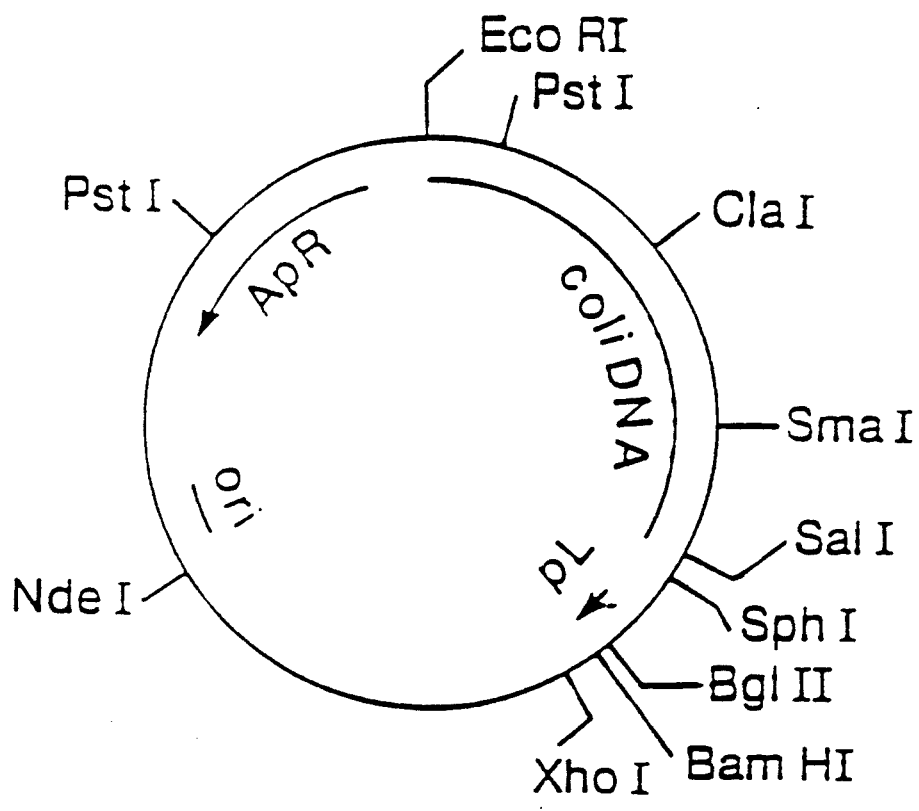
FIG. 2—A restriction site and function map of plasmid pKC283PX.

The reaction was terminated, and the XhoI digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 2 of the accompanying drawings.

EXAMPLE 3.A.3

Construction of E. coli K12 MO (λ±)/pKC283PX

E. coli K12 Mo (λ+) can be obtained brom the Northern Regional Research Laboratories in lyophylized form under the accession number NRRL B-15993. E. coli K12 MO(λ+) comprises the wildtype lambda pL cI repressor gene, so that transcription from the hybrid pL-lpp promoter of the present invention does not occur in E. coli K12 MO(λ+) cells. The lyophils are reconstituted, single colonies of MO (λ+) are isolated, and a 10 ml overnight culture of the MO(λ+) cells is prepared in substantial accordance with the procedure of Example 29A1, except that the temperature of incubation is 37° C. and no ampicillin is used in the growth media.

Fifty μl of the overnight culture were used to inoculate 5 ml of LB media which also contained 10 mM $MgSO_4$ and 10 mM $MgCl_2$. The culture was incubated at 37° C. overnight with vigorous shaking. The following morning, the culture was diluted to 200 ml with LB media containing 10 mM $MgSO_4$ and 10 mM $MgCl_2$. The diluted culture was incubated at 37° C. with vigorous shaking until the absorbence at 550 nm ($A_{550}$) was about 0.5, which indicated a cell density of about $1 \times 10^8$ cells/ml. The culture was cooled for ten minutes in an ice-water bath, and the cells were then collected by centrifugation at 4000 g for 10 minutes at 4° C. The cell pellet was resuspended in 100 ml of cold 10 mM $MgSO_4$ and then immediately re-pelleted by centrifugation. The cell pellet was resuspended in 100 ml of 30 mM $CaCl_2$ and incubated on ice for 20 minutes.

The cells were again collected by centrifugation and resuspended in 10 ml of 30 mM $CaCl_2$. A one-half ml aliquot of the cells was added to the ligated DNA prepared in Example 29A2; the DNA had been made 30 mM in $CaCl_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred pi aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 29A1, but the CsCl gradient step was omitted until the desired E. coli K12 MOλ+)/pKC283PX transformants were identified. A restriction site and function map of plasmid pKC283PX is presented in FIG. 2 of the accompanying drawings.

EXAMPLE 3.A.4

Construction of E. coli K12 MO(λ±)/pKC283-L

Ten mg of plasmid pKC283PX DNA prepared in accordance with the procedure of Example 29A1 were dissolved in 20 μl of 10X high-salt buffer, 20 ml 1 mg/ml BSA, 5 μl (~50 units) restriction enzyme BglII, 5 μl (~50 units) restriction enzyme XhoI, and 150 μl of water, and the resulting reaction was incubated at 37° C. for two hours. The reaction was stopped, and after precipitating the BglII-XhoI digested DNA, the DNA was resuspended in 5 μl of TE buffer.

A DNA linker with single-stranded DNA ends characteristic of BglII and XhoI restriction enzyme cleavage was synthesized and kinased. The linker was kinased in substantial accordance with the procedure of Example 3A2. The DNA linker had the following structure;

```
5'-GATCTATTAACTCAATCTAGAC-3'      (Seq. ID No. 5)
   |||||||||||||||||||||
   3'-ATAATTGAGTTAGATCTGAGCT-5'   (Seq. ID No. 6)
```

The linker depicted above was synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura at al., 1977, Science 198:1056 and in Crea et al., 1978, Proc, Nat. Acad. Sci. USA 75:576. In addition, an especially preferred method of synthesizing DNA is disclosed in Hsiung et al., 1983, Nucleic Acid Research 11:3227 and Narang at al., 1980, Methods in Enzymology 68:90.

Figure 3:
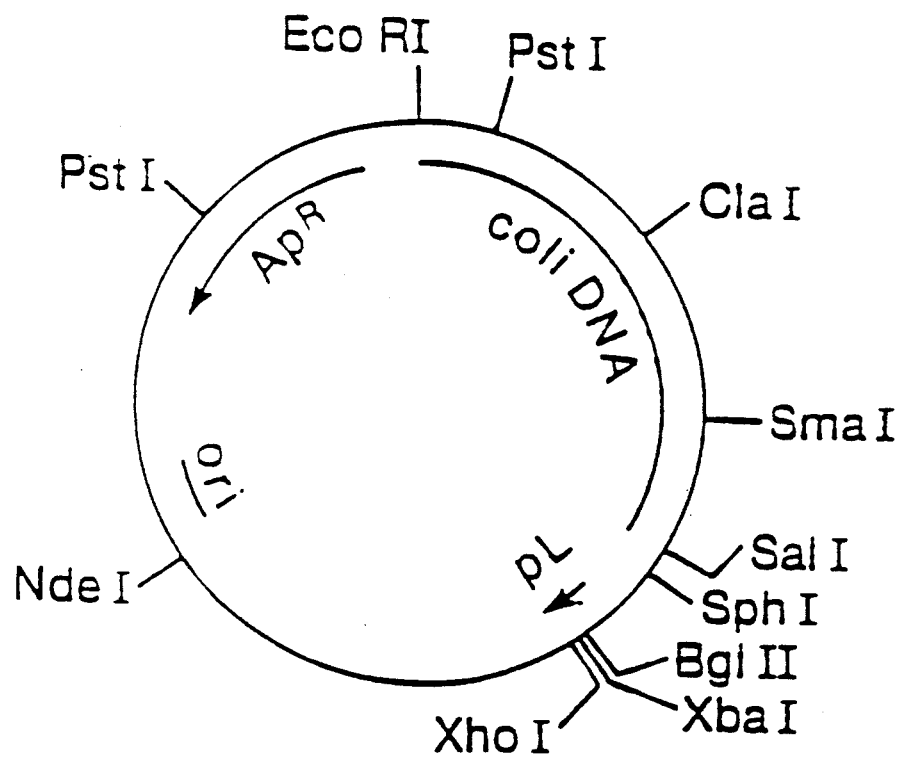
FIG. 3—A restriction site and function map of plasmid pKC283-L.

The linker and BglII-XhoI-digested plasmid pKC283PX were ligated in substantial accordance with the procedure of Example 3A2. The ligated DNA constituted the desired plasmid pKC283-L. A restriction site and function map of plasmid pKC283-L is presented in FIG. 3 of the accompanying drawings. The plasmid pKC283-L DNA was used to transform E. coli K12 MO(λ+) and the resulting E. coli K12 MO(λ+)/pKC283-L transformants were identified in substantial accordance with the procedure of Example 3A3.

EXAMPLE 3.A.5

Construction of E. coli K12 MO(λ+)/pKC283-LB

About 10 μg of plasmid pKC283-L DNA, prepared in substantial accordance with the procedures of Example 29A1, were dissolved in 20 μl 10X high-salt buffer, 20 μl 1 mg/ml BSA, 5 μl (~50 units) restriction enzyme XhoI, and 155 μl of H2O, and the resulting reaction was incubated at 37° C. for two hours. The XhoI-digested plasmid pKC283-L DNA was then precipitated from the reaction mixture by the addition of three volumes of 95% ethanol and one-tenth volume of 3M sodium acetate, incubated in a dry ice-ethanol bath for five minutes, and centrifugation. The resulting DNA pellet was washed with 70% ethanol, dried, and resuspended in 2 μl 10X nick-translation buffer (0.5M Tris-HCl, pH 7.2; 0.1M MgSO4; and 1 mM DTT), 1 μl of a solution 2 mM in each of the deoxynucleotide triphosphates, 15 ml of H2O, 1 ml (~6 units as defined by P-L Biochemicals) of Klenow, which is the large fragment of E. coli DNA polymerase I, and 1 μl of 1 mg/ml BSA. The resulting reaction was incubated at 25° C. for 30 minutes; the reaction was stopped by incubating the solution at 70° C. for five minutes.

BamHI linkers (5'-CGGGATCCCG-3')(Seq. ID No.7) were kinased and ligated to the XhoI-digested, Klenow-treated plasmid pKC283-L DNA in substantial accordance with the procedure of Example 3A2. After the ligation reaction, the DNA was digested with about 100 units of BamHI for about 2 hours at 37° C. in high-salt buffer. After the BamHI digestion, the DNA was prepared for ligation in substantial accordance with the procedure of Example 3A2.

Figure 4:
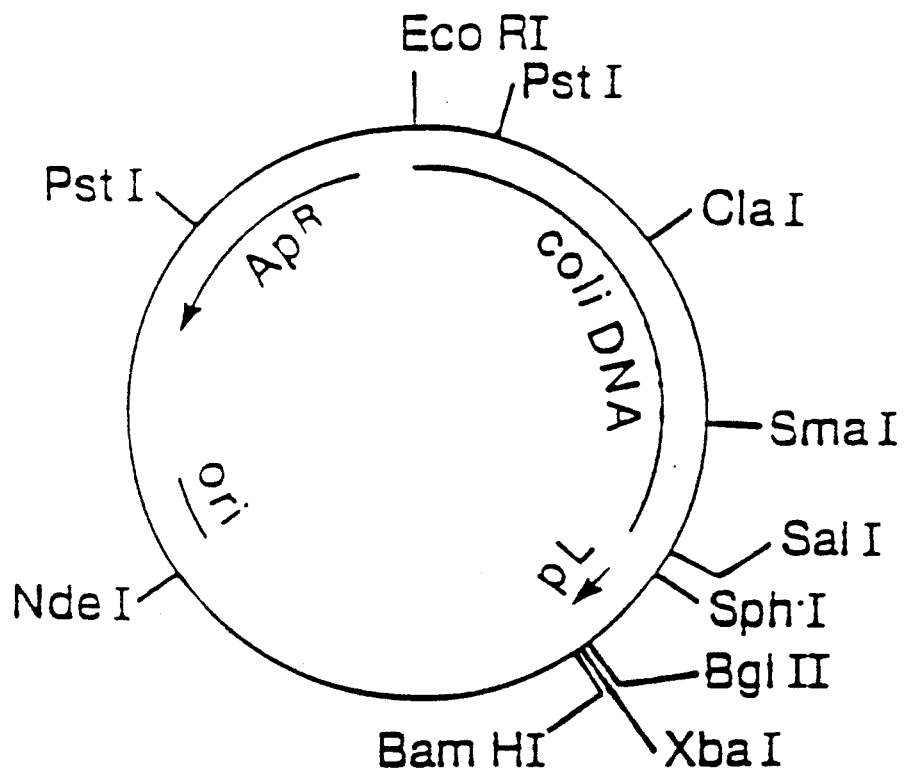
FIG. 4—A restriction site and function map of plasmid pKC283-LB.

The ~5.9 kb BamHI restriction fragment was circularized by ligation and transformed into E. coli K12 MO(λ+) in substantial accordance with the procedures of Examples 3A2 and 3A3. The E. coli K12 MO(λ+)/pKC283-LB transformants were identified, and then plasmid pKC283-LB DNA was prepared in substantial accordance with the procedure of Example 3A1. A restriction site and function map of plasmid pKC283-LB is presented in FIG. 4 of the accompanying drawings.

EXAMPLE 3.A.6

Construction of E. coli K12 MO(λ+)/pL32

Figure 5:
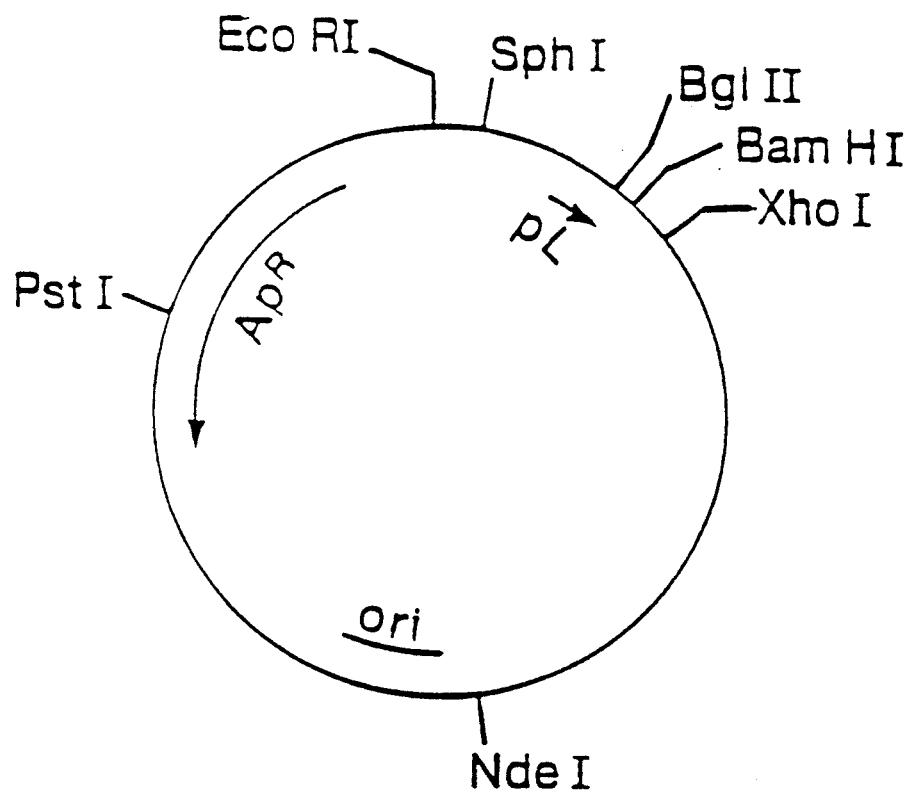
FIG. 5—A restriction site and function map of plasmid pKC283-PRS.

About 10 mg of plasmid pKC283PX were digested with restriction enzyme SalI in high-salt buffer, treated with Klenow, and ligated to EcoRI linkers (5'-GAG-GAATTCCTC-3')(Seq. ID No.8) in substantial accordance with the procedure of Example 3A5, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform E. coli K12 MO (λ+) in substantial accordance with the procedure of Example 3A3. After the E. coli K12 MO(λ+)/pKC283PRS transformants were identified, plasmid pKC283PRS DNA was prepared in substantial accordance with the procedure of Example 3A1. A restriction site and function map of plasmid pKC283PRS is presented in FIG. 5 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling temperature agarose (FMC Corporation, marine Colloids Division, Rockland, Me. 04841) gel for 2-3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 ug of the ~0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

Figure 6:
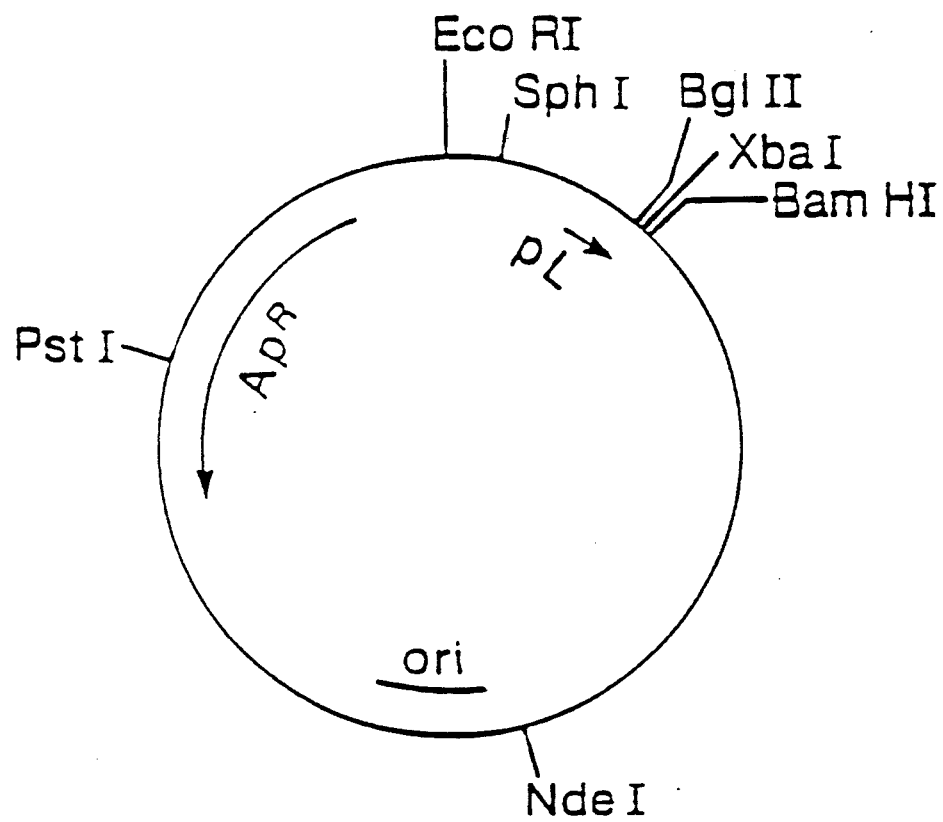
FIG. 6—A restriction site and function map of plasmid pL32.

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 3A2. The ligated DNA constituted the desired plasmid pL32. A restriction site and function map of plasmid pL32 is presented in FIG. 6 of the accompanying drawings. Plasmid pL32 was transformed into E. coli K12 MO(λ+) cells in substantial accordance with the procedure of Example 3A3. Plasmid pL32 DNA was prepared from the *E. coli* K12 MO (λ+) /pL32 transformants in substantial accordance with the procedure of Example 3A1. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together. Alternatively, plasmid pL32 may be constructed by carrying out the SalI-EcoRI excision and ligation of the first paragraph of this Example upon plasmid pKC283-LB.

EXAMPLE 3.A.7

Construction of *E. coli* K12 MO(λ±)/pL47

Figure 7:
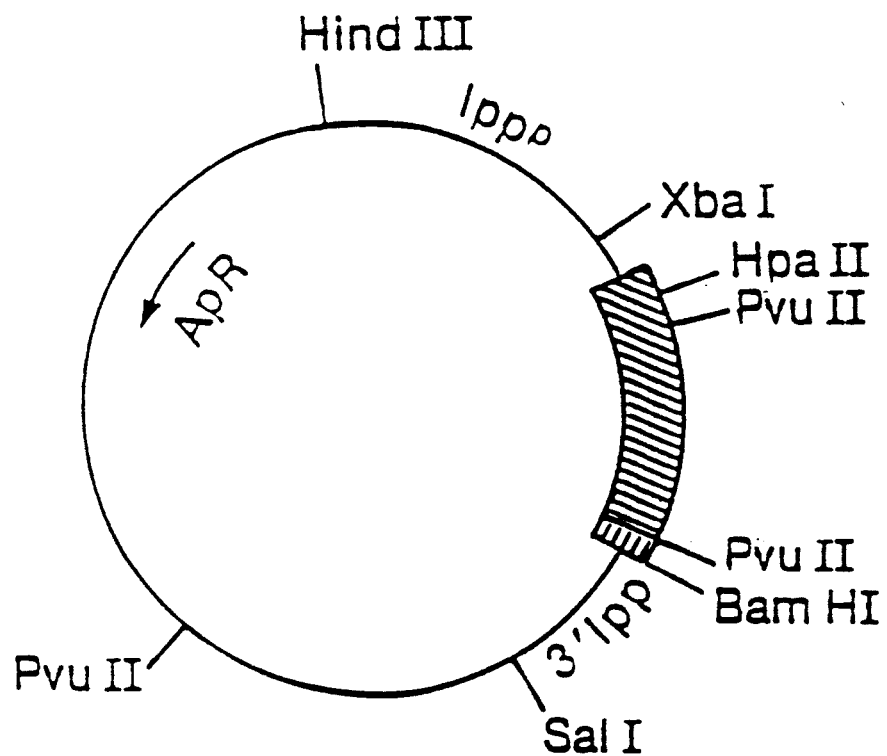
FIG. 7—A restriction site and function map of plasmid pNM789.
Figure 8:
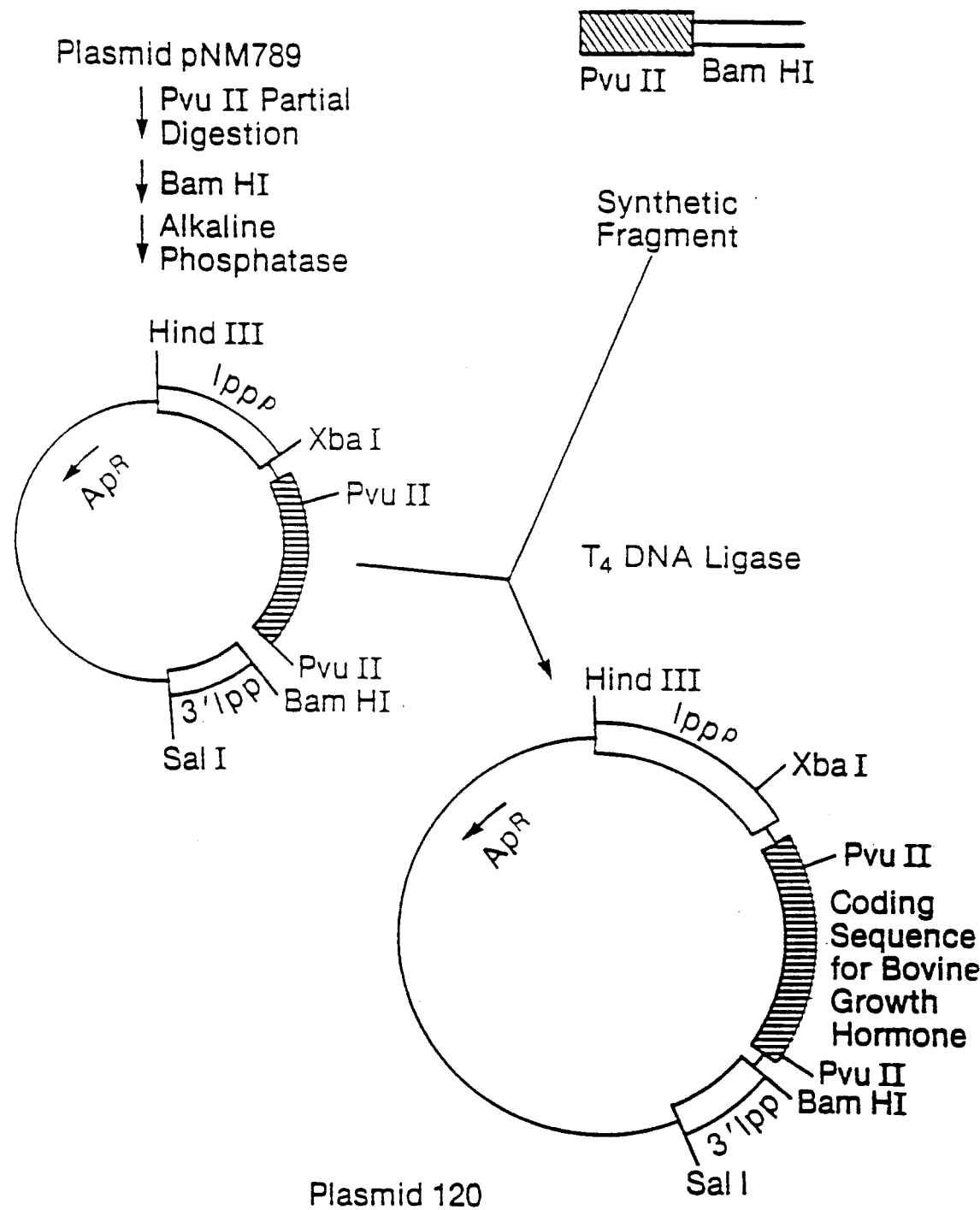
FIG. 8—A schematic outline of the construction of plasmid 120.

*E. coli* K12 RV308/pNM789 can be obtained from the Northern Regional Research Laboratories in lyophilized form under the accession number NRRL B-18216. A restriction site and function map of pNM789 is presented in FIG. 7 of the accompanying drawings. Plasmid DNA is extracted from the culture in substantial accordance with the teaching of Example 1, except that the temperature of incubation is 37° C. Ten micrograms of pNM789 are suspended in 200 μl PvuII buffer (50 mM Tris-HCl (pH 7.5), 60 mM NaCl and 6 mM MgCl$_2$). One unit of PvuII is added and the reaction mix is incubated for 5 minutes at 37° C. The enzyme is inactivated by heating 10 minutes at 65° C. 30 μl of 10X BamHI buffer (200 mM Tris-HCl (pH 8.0), 1M NaCl and 70 mM MgCl$_2$), 70 μl H$_2$O and 10 units of BamHI are next added and the reaction is incubated for 1 hour at 37° C. This is followed by the addition of 5 units of alkaline phosphatase and incubation for 1 hour at 65° C. The DNA fragments are separated on a 1 percent agarose gel, and a DNA fragment (FIG. 8) the size of a single cut fragment is purified.

A DNA linker with a blunt end and a BamHI end is synthesized in substantial accordance with the teaching of Example 3A4. This linker (shown at 118 in FIG. 8) has the following structure:

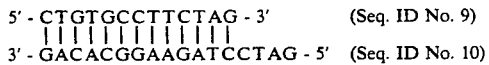

```
5' - CTGTGCCTTCTAG - 3'      (Seq. ID No. 9)
     |||||||||||||
3' - GACACGGAAGATCCTAG - 5'  (Seq. ID No. 10)
```

The linker is kinased and ligated into the BamHI-PvuII digested plasmid pNM789 in substantial accordance with the teaching of Example 3A2. This ligation mixture is used to transform *E. coli* K12 RV308 cells and plasmid isolation is performed upon these transformants in substantial accordance with the teaching of Example 3A3. Several plasmids are selected which contain the appropriate size PvuII fragment (494bp) and 2WI-BamHI fragment (628bp). The sequence of at least two of these is determined by sequencing from the BamHI site toward the unique SmaI site and one clone is selected with the desired sequence. This intermediate plasmid is designated plasmid 120. A schematic outline of this procedure and a restriction site and function map of plasmid 120 is presented in FIG. 8 of the accompanying drawings.

To isolate the EK-BGH-encoding DNA, about 10 mg of plasmid 120 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated and prepared for ligation in substantial accordance with the procedure of Example 29A6.

Figure 9:
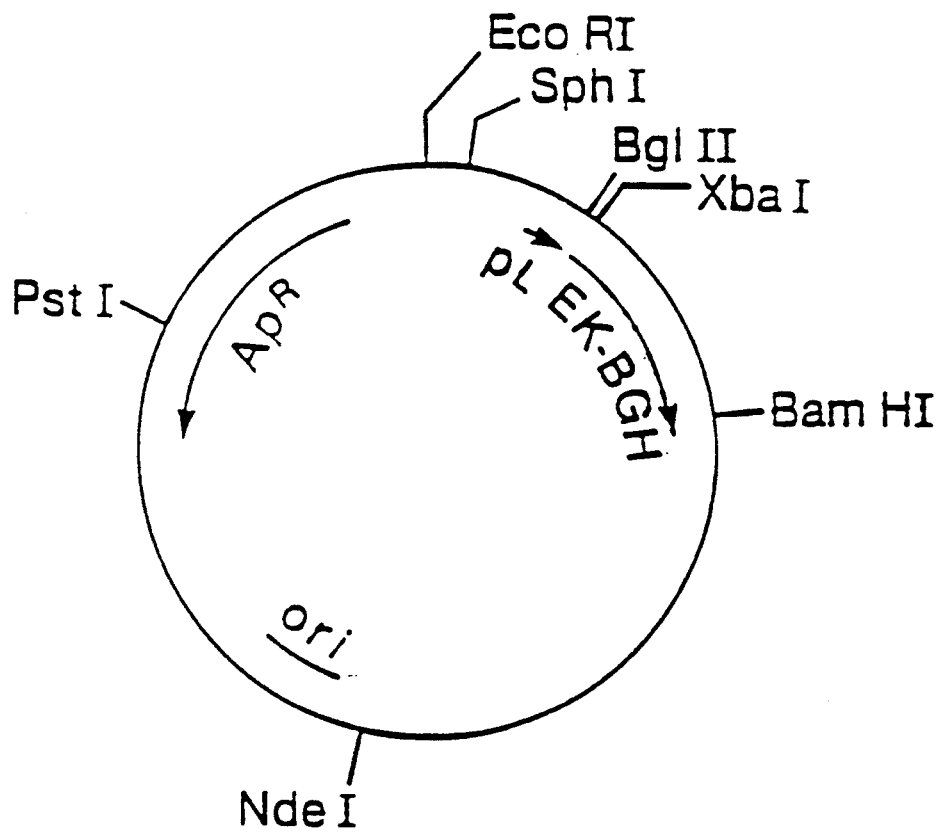
FIG. 9 A restriction site and function map of plasmid pL47.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid 120 in substantial accordance with the procedure of Example 3A2 to yield plasmid pL47. A restriction site and function map of plasmid pL47 is presented in FIG. 9 of the accompanying drawings. Plasmid pL47 was transformed into *E. coli* K12 MO(λ+) in substantial accordance with the procedure of Example 3A3, and the *E. coli* K12 MO(λ+)/pL47 transformants were identified. Plasmid pL47 DNA was prepared from the transformants in substantial accordance with the procedures of Example 3A1.

EXAMPLE 3.A.8

Construction of *E. coli* K12 RV308/pPR12AR1

Figure 10:
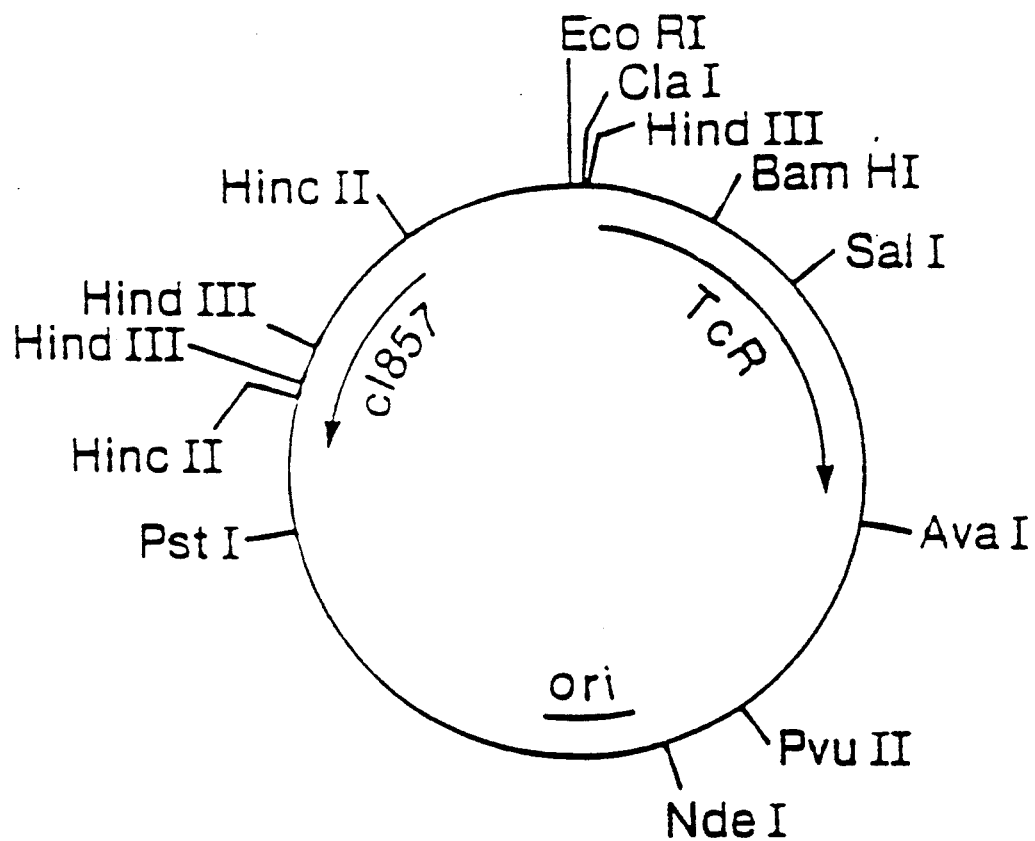
FIG. 10—A restriction site and function map of plasmid pPR12.

Plasmid pPR12 comprises the temperature-sensitive pL repressor gene cI857 and the plasmid pBR322 tetracycline esistance-conferring gene. Plasmid pPR12 is disclosed and claimed in U.S. Pat. No. 4,436,815, issued 13 Mar. 1984. A restriction site and function map of plasmid pPR12 is presented in FIG. 10 of the accompanying drawings.

About 10 μg of plasmid pPR12 were digested with about 50 units of restriction enzyme EcoRI in 200 ml of high-salt buffer at 37° C. for two hours. The EcoRI-digested plasmid pPR12 DNA was precipitated and treated with Klenow in substantial accordance with the procedure of Example 3A5. After the Klenow reaction, the EcoRI-digested, Klenow-treated plasmid pPR12 DNA was recircularized by ligation in substantial accordance with the procedure of Example 3A2. The ligated DNA, which constituted the desired plasmid pPR12ΔR1, was used to transform *E. coli* K12 RV308 in substantial accordance with the procedure of Example 3A3, except that selection was based on tetracycline (5 ug/ml) resistance, not ampicillin resistance. *E. coli* K12 RV308 is available from the NRRL under the accession number NRRL B-15624. After the *E. coli* K12 RV308/pPR12ΔR1 transformants were identified, plasmid pPR12ΔR1 DNA was prepared from the transformants in substantial accordance with the procedure of Example 3A11.

Figure 11:
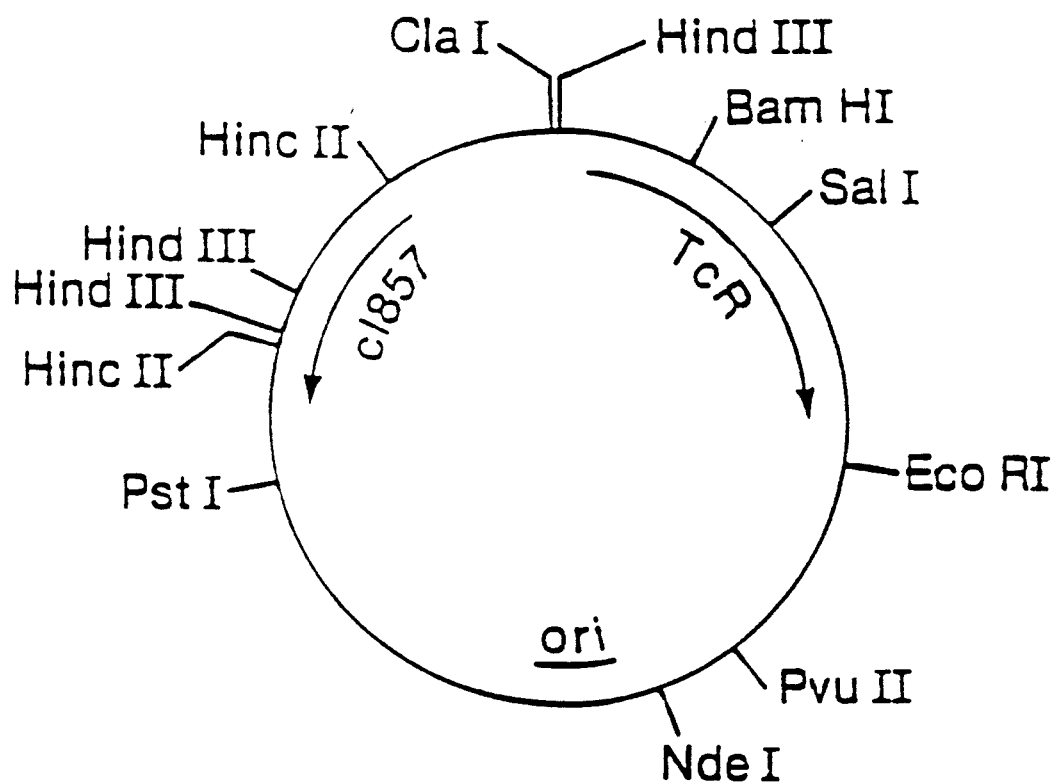
FIG. 11—A restriction site and function map of plasmid pPR12AR1.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and treated with Klenow in substantial accordance with the procedure of Example 3A5. After the Klenow reaction, the AvaI-digested, Klenow-treated plasmid pPR12ΔR1 DNA was ligated to EcoR1 linkers (5'-GAGGAATTCCTC-3') in substantial accordance with the procedure of Example 3A2. After the linker ligation, the DNA was precipitated and then resuspended in about 200 μl of high-salt buffer containing about 50 units of restriction enzyme EcoR1. The resulting reaction was incubated at 37° C. for about 2 hours. After the EcoR1 digestion, the reaction mixture was loaded onto an agarose gel, and the ~5.1 kb EcoR1 restriction fragment was purified in substantial accordance with the procedure of Example 3A6. The ~5.1 kb EcoR1 restriction fragment was recircularized by ligation in substantial accordance with the procedure of Example 3A2. The ligated DNA constituted the desired plasmid pPR12ΔR1. The plasmid pPR12ΔR1 DNA was transformed into *E. coli* K12 RV308 in substantial accordance with the procedure of Example 3A3, except that selection was based on tetracycline resistance, not ampicillin resistance. After identifying the *E. coli* K12 RV308/pPR12AR1 transformants, plasmid pPR12AR1 DNA was prepared in substantial accordance with the procedure of Example 3A1. A restriction site and function map of plasmid pPR12AR1 is presented in FIG. 11 of the accompanying drawings.

EXAMPLE 3.A.9

Construction of *E. coli* K12 RV308/pL110

About 10 μg of plasmid pPR12AR1 DNA were suspended in about 200 ml of high-salt buffer containing about-50 units each of restriction enzymes PstI and EcoRI, and the digestion reaction was incubated at 37° C. for about 2 hours. The reaction mixture was then loaded onto an agarose gel, and the ~2.9 kb PstI-EcoR1 restriction fragment of plasmid pPR12AR1 was isolated and prepared for ligation in substantial accordance with the procedure of Example 3A6.

About 10 ug of plasmid pL47 were digested with restriction enzymes PstI and BamHI in 200 ul of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation in substantial accordance with the procedure of Example 3A6. In a separate reaction, about 10 ug of plasmid pL47 DNA were digested with restriction enzymes EcoRI and BamHI in 200 ul of high-salt buffer at 37° C. for two hours, and the ~1.03 kb EcoRI-BamHI restriction fragment that comprised the novel transcriptional and translational activating sequence and the EK-BGH encoding DNA was isolated and prepared for ligation in substantial accordance with the procedure of Example 3A6. The ~2 ug of the ~1.03 kb EcoRI-BamHI restriction fragment obtained were used in the construction of plasmid pL110.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308 in substantial accordance with the procedure of Examples 3A2 and 3A3, except that tetracycline resistance, not ampicillin resistance, was used as the basis for selecting transformants.

Figure 12:
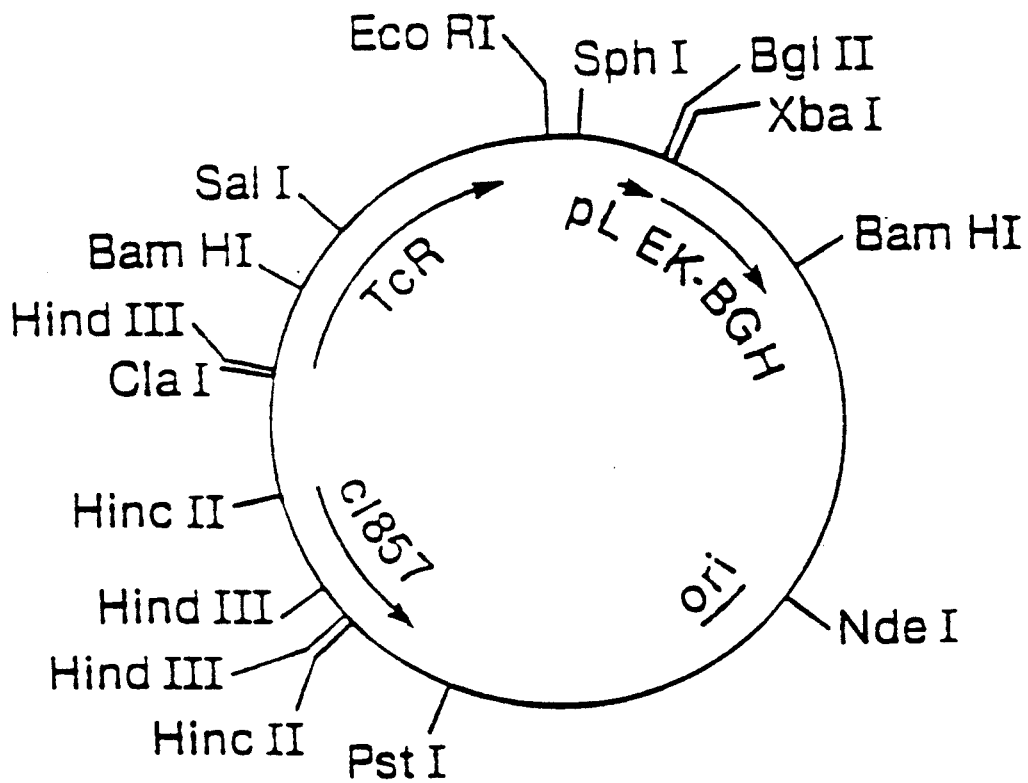
FIG. 12—A restriction site and function map of plasmid pL110.

Two PstI restriction enzyme recognition sites are present in the EK-BGH coding region that are not depicted in the restriction site and function maps presented in the accompanying drawings. A restriction site and function map of plasmid pL110 is presented in FIG. 12 of the accompanying drawings.

EXAMPLE 3.A.10

Construction of *E. coli* K12 RV308/pL110C

Example 3.A.10.a Construction of *E. coli* K12 RV308/pL110A

About 1 μg of plasmid pL110 DNA was digested with restriction enzyme NdeI in 20 μl total volume containing 2 μl of lox high-salt buffer (1.0M NaCl; 0.50M Tris-HCl, pH=7.5; 0.10M MgCl$_2$; and 10 mM dithiothreitol) and 3 units of NdeI enzyme for 1 hour at 37° C. The reaction mixture was extracted with phenol/chloroform and the DNA precipitated with ethanol. The NdeI-digested plasmid pL110 DNA was dissolved in 50 μl of 1X Klenow buffer (40 mM KPO$_4$, pH=7.5; 6.6 mM MgCl$_2$; 1.0 mM 2-mercaptoethanol; 33 μl dATP; 33 μl dCTP; 33 μM dGTP; and 33 μM TTP). Two μl (~10 units, New England Biolabs) of the large fragment of *E. coli* DNA polymerase I, known as Klenow, were added to and mixed with the DNA, and the resulting reaction was incubated at 16° C. for 1 hour. The reaction was terminated by phenol extraction and the DNA conventionally purified. The NdeI-digested, Klenow-treated DNA was then ligated with T4 DNA ligase at 4° C. for 16 hours. The resulting DNA was used to conventionally transform *E. coli* K12 strain RV308 (NRRL B-15624). Transformants were selected on L-agar plates containing 100 mg/ml ampicillin and plasmids isolated from resistant colonies by the rapid alkaline extraction procedure described by Birnboim and Doly. A plasmid (pL110A in FIG. 13) lacking an NdeI site was selected.

EXAMPLE 3.A.10.b Construction of Phage pL110B by Site-Specific Mutagenesis

Figure 13:
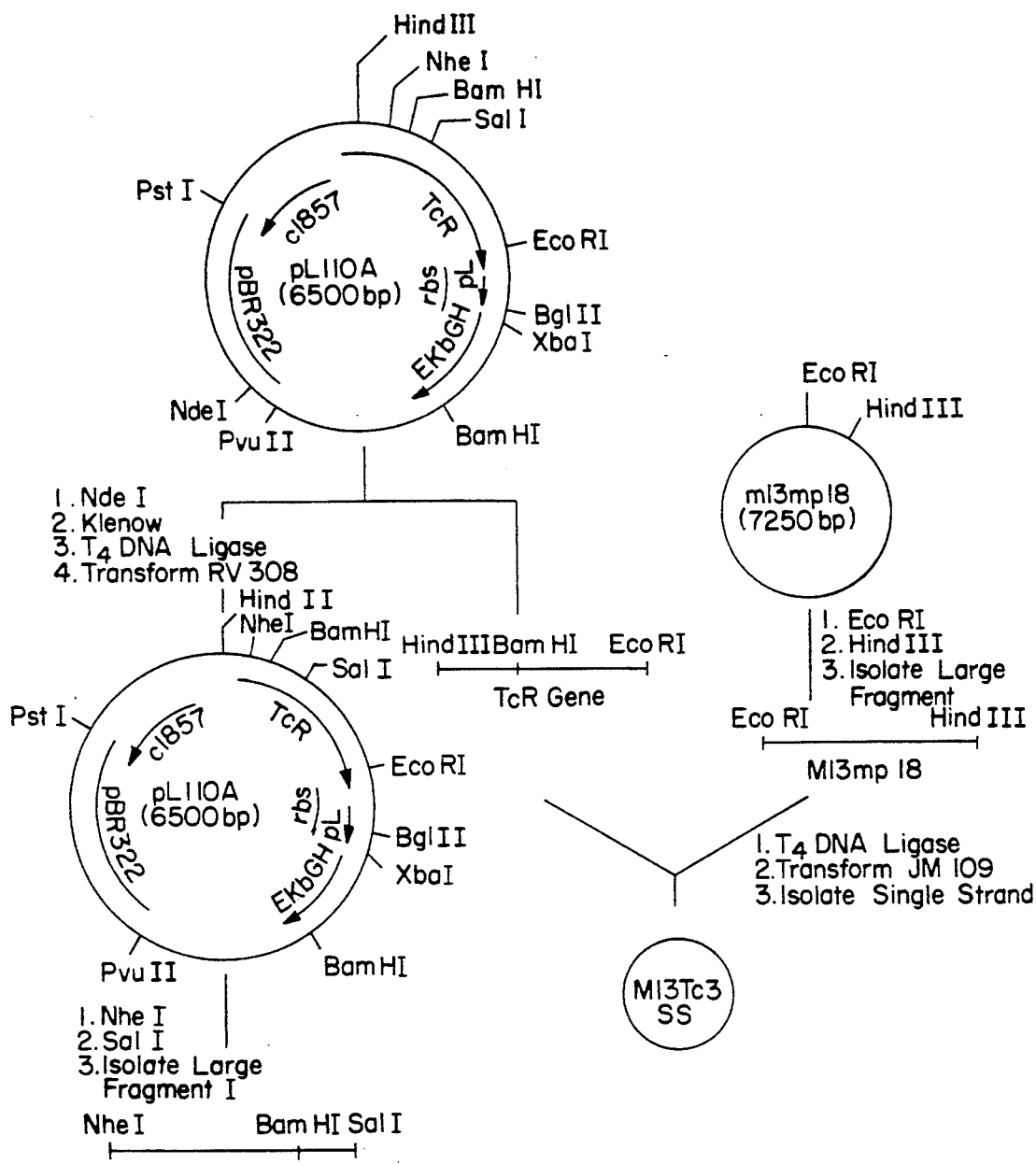
FIG. 13—A schematic outline of the construction of plasmid pL110C.

The protocol for eliminating the BamHI site in the tetracycline resistance-conferring gene by site-specific mutagenesis is shown on the right hand side of FIG. 13 of the accompanying drawings.

EXAMPLE 3.A.10.b(i) Construction of Phage M13Tc3

Plasmid pL110 served as the source of the tetracycline resistance-conferring gene. About 50 μg of plasmid pL110 in 50 μl of TE buffer were added to 25 μl of 10X HindIII buffer and 170 μl of H$_2$O. About 5 μl (~50 units) of restriction enzyme HindIII were added to the solution of plasmid pL110 DNA, and the resulting reaction was incubated at 37° C. for 2 hours. About 13 μl of 2M Tris-HCl, pH=7.4, and 5 μl (~50 units) of restriction enzyme EcoRI were added to the HindIII digested plasmid pL110 DNA, and the reaction was incubated for 2 more hours at 37° C. The reaction was stopped by extracting the reaction mixture with TE-saturated phenol; the phenol was removed by chloroform extractions. The EcoRI-HindIII-digested plasmid pL110 DNA was then collected by precipitation and centrifugation, loaded into a 1% agarose gel, and the large ~4.3 kb EcoRI-HindIII restriction fragment was isolated and purified.

About 5 μg of phage ml3mp18 (New England Biolabs) were dissolved in 50 μl of TE buffer and then digested with HindIII and EcoRI as described above. The HindIII-EcoRI-cut phage M13mp18 DNA was purified as described for pL110 except that an ~7.25 kb restriction fragment was isolated and purified.

About 100 nanograms of the ~4.3 kb HindIII-EcoRI fragment of plasmid pL110 were mixed with about 100 nanograms of the ~7.25 kb HindIII-EcoRI fragment of phage M13mp18, 2 μl of 10X ligase buffer, 1 μl (~100 units) of T4 DNA ligase, and 14 μl of H$_2$O. The ligation reaction was incubated at 15° C. for 1.5 hours; the ligated DNA constituted the desired phage m13Tc3 DNA. A restriction site and function map of phage m13Tc3 is presented in FIG. 13 of the accompanying drawings.

One ml of an overnight culture of *E. coli* K12 JM109 (*E. coli* K12 JM101, available from New England Biolabs, can be used instead of *E. coli* K12 JM109) was used to inoculate 50 ml of L broth, and the resulting culture was incubated at 37° C. with aeration until the O.D.$_{660}$ was between 0.3 and 0.4. The cells were resuspended in 25 ml of 10 mM NaCl, incubated on ice for 10 minutes, and collected by centrifugation. The cells were resuspended in 1.25 ml of 75 mM CaCl$_2$; a 200 μl aliquot of the cells was removed, added to 10 μl of the ligated DNA prepared above, and incubated on ice for about 40 minutes. The cell-DNA mixture was then incubated at 42° C. for 2 minutes, and varying aliquots (1, 10, and 100 μl) were removed and added to 3 ml of top agar (L broth with 0.5% agar kept molten at 45° C.) that also contained 50 ml of 2% X-Gal, 50 μl of 100 mM IPTG, and 200 μl of *E. coli* K12 JM109 in logarithmic growth phase. The cell-top agar mixture was then plated on L-agar plates containing 40 mg/ml X-Gal (5-bromo-4chloro-3-indolyl-β-D-thiogalactoside) and 0.1 mM IPTG (isopropyl-β-D-thiogalactoside), and the plates were incubated at 37° C. overnight.

The following morning, several clear, as opposed to blue, plaques were individually used to inoculate 2 ml of L broth, and the resulting cultures were incubated at 37° C. with aeration for 2 hours. The absence of blue color indicates the desired DNA insertion occurred. Then, the cultures were centrifuged, and 200 μl of the resulting supernatant were added to 10 ml cultures (O.D.$_{550}$=0.5) of *E. coli* K12 JM109 growing at 37° C. with aeration. These cultures were incubated for another 30 minutes at 37° C.; then, the cells were pelleted by centrifugation and used to prepare the replicative form of the recombinant phage they contained. Double stranded, replicative form phage DNA was isolated from the cells using a scaled-down version of the procedure described in Example 1. Transformants containing phage m13Tc3 DNA were identified by restriction enzyme analysis of their phage DNA.

EXAMPLE 3.A10.b(ii) Preparation of Single-Stranded Phage m13Tc3 DNA

One and one-half ml of an overnight culture of *E. coli* K12 JM109/m13Tc3 were centrifuged, and 100 μl of the phage m13Tc3-containing supernatant were used to inoculate a 25 ml culture of *E. coli* JM109 at an O.D.$_{660}$ of about 0.4–0.5. The culture was incubated for 6 hours at 37° C. with aeration, at which time the culture was centrifuged and the resulting supernatant, about 20 ml, transferred to a new tube. About 2 ml of a solution containing 20% polyethylene glycol (PEG) 6000 and 14.6% NaCl were added to the supernatant, which was then incubated on ice for 20 minutes.

The supernatant was centrifuged for 25 minutes at 7000 rpm, and the resulting pellet, which contained single-stranded phage m13Tc3 DNA, was resuspended in 500 μl of TE buffer. The DNA solution was extracted twice with TE-saturated phenol and twice with chloroform. The single-stranded DNA was then precipitated using NaOAc and ethanol and centrifuged. The resulting pellet was washed with 70% ethanol, dried, and then dissolved in 60 μl of H$_2$O.

EXAMPLE 3.A.10b(iii) Mutagenesis

The single-stranded DNA fragment used in the mutagenesis was synthesized on an automated DNA synthesizer. The fragment has the sequence, 5'-CCCGTCCTGTGGATACTCTACGCCGA-3'  (Seq. ID No.11)

and is homologous to the region surrounding the BamHI site (5'-GGATCC-3') in the tetracycline resistance-conferring gene from plasmid pBR322, except that the A residue second from the 5' end (or third from the 3' end) is a C in plasmid pBR322. This change does not alter the amino acid composition of the tetracycline resistance-conferring protein but eliminates the BamHI site.

About 10 picomoles of the mutagenic primer and the M13 universal primer (Bethesda Research Laboratories (BRL), P.O. Box 6009, Gaithersburg, Md. 20760) were individually treated with 10 units (BRL) of T4 polynucleotide kinase in 20 μl of 1X kinase buffer (60 mM Tris-HCl, pH=7.8; 15 mM 2-mercaptoethanol; 10 mM MgCl$_2$; and 0.41 μM ATP) for 30 minutes at 37° C. The kinase-treated DNAs were used in the mutagenesis procedure described below.

The annealing reaction was carried out mixing together 300 nanograms (1.2 μl) of single-stranded phage m13Tc3, 1 picomole (2 μl) of the universal primer, 1 picomole (2 μl) of the mutagenic primer, 2 μl of 10X annealing buffer (100 mM Tris-HCl, pH=7.5; 1 mM EDTA; and 500 mM NaCl), and 12.8 ml of H$_2$O. The reaction was incubated at 80° C. for 2 minutes, at 50° C. for 5 minutes, and then allowed to cool to room temperature.

The extension reaction was carried out by adding 5 μl of 10X extension buffer (500 mM Tris-HCl, pH=8; 1 mM EDTA; and 120 mM MgCl$_2$); 5 μl of 2 mM dATP; 1 μl of a solution 6 mM in each of dGTP, TTP, and dCTP; 1 μl (~2 units, Pharmacia P-L Biochemicals, 800 Centennial Avenue, Piscataway, N.J. 08854) of Klenow enzyme; 1 μl (100 units) of T4 DNA ligase; and 17 μl of H$_2$O to the mixture of annealed DNA. The extension reaction was incubated at room temperature for 1 hour, then at 37° C. for 2.5 hours, and then overnight at 4° C.

The reaction was stopped by two extractions with TE-saturated phenol, which were followed by two extractions with CHCl$_3$. The DNA was precipitated with ethanol and NaOAc. The DNA was collected by centrifugation and resuspended in 50 μl of H$_2$O, and 6 μl of 10X S1 buffer were then added to the solution of DNA.

The solution of DNA was split equally into three tubes. About 200 units (Miles Laboratories) of S1 nuclease were added to two of the tubes. One S1 reaction was incubated at room temperature for 5 minutes, the other for 10 minutes. The reactions were stopped by extracting the reaction mixture twice with TE-saturated phenol. The phenol extractions were followed by two extractions with chloroform; then, the DNA was precipitated from the reaction mixture with NaOAc and ethanol. The untreated sample of DNA served as a negative control. The S1-treated samples were kept separate from each other throughout the remainder of the procedure but gave similar results.

The DNA pellets were resuspended in 20 μl Of H$_2$O, and 10 μl of the resulting solution were used to transform *E. coli* K12 JM109 (*E. coli* K12 JM101 could also be used) in accordance with the procedure used during the construction of phage m13Tc3, except that no IPTG or X-Gal was added to the plates.

Double-stranded replicative form DNA from about 48 plaques was isolated as described above and screened for the presence of a BamHI restriction site. Isolates without a BamHI site were further screened by preparing single-stranded DNA as described above. The single-stranded DNA was sequenced using the dideoxy sequencing method (J. H. Smith, 1980, Methods in Enzymology 65: 560–580). The desired isolate was designated pL110B (FIG. 13).

EXAMPLE 3.A.10.c Construction of Plasmid pL110C

About 50 μg of the replicative form of phage pL110B DNA were digsted in 250 μl of 1X NheI buffer (50 mM NaCl; 6 mM Tris.HCl, pH=7.5; 6 mM MgCl$_2$; and 6 mM b-mercaptoethanol) containing ~50 units of NheI restriction enzyme at 37° C. f or 2 hours. Five μl of 5M NaCl were then added to the NheI-digested phage pL110B DNA, followed by 5 μl (~50 units) of SalI restriction enzyme. Digestion was continued for 2 hours at 37° C. The desired ~422 bp NheI-SalI fragment containing the mutated region of the tetracycline resistance-conferring gene was then isolated from an acrylamide gel, according to well known standard procedures.

Plasmid pL110A DNA was digested with NheI and SalI under identical conditions, except that plasmid pL110A was substituted for phage pL110B. The ~6.1 kb NheI-SalI restriction fragment of plasmid pL110A was purified from agarose.

The desired plasmid pL110C was constructed by ligating together 100 nanograms each of the NheI-SalI fragments of pL110A (~6.1 kb) and pL110B (~422 bp) using conventional procedures. A restriction site and function map of plasmid pL110C is presented in FIG. 13 of the accompanying drawings. The desired plasmid pL110C confers tetracycline resistance to 10 μg/mL tetracycline in E. coli but lacks a BamHI site in the tetracycline resistance-conferring gene.

EXAMPLE 3.A.11 Construction of Plasmid pCZR111

Plasmid pL110C contains a single ClaI restriction site which was removed by running the following reactions. About 1 μg of plasmid pL110C was digested with ClaI in substantial accordance with the teaching of Example 3A2, except restriction enzyme ClaI and 10X ClaI Buffer (500 mM NaCl, 100 mM Tris-HCl (pH 7.9) and 100 mM MgCl$_2$) were used. The ClaI-digested DNA was then treated with Klenow in substantial accordance with the teaching of Example 3A5, except only dCTP, rather than all four dNTPs, was added.

The DNA was then precipitated and resuspended in 50 μl of Mung Bean Nuclease Buffer (50 mM Sodium Acetate (pH 5.0), 30 mM NaCl and 1 mM ZnSO$_4$). One unit of Mung Bean Nuclease (commercially available from New England Biolabs) was added and the reaction was incubated at 30° C. for 30 minutes. The tube was then placed in ice and NaCl was added to 0.2M, then the mixture was phenol/chloroform extracted, ethanol precipitated and resuspended in 10 mM 3.,0 Tris-HCl (pH 8.0). The DNA was then self-ligated and transformed into E. coli cells in substantial accordance with the teaching of Examples 3A3 and 3A4. The resultant plasmid was designated plasmid pCZR111.

EXAMPLE 3.A.12. Construction of Plasmid pCZR126S

About 26 μg of plasmid pCZR111 was digested with XbaI as follows. 10XbaI buffer consists of 600 mM Tris-Hcl, 100 mM MgCl$_2$, 1M NaCl, and 10 mM 2-mercaptoethanol, pH 7.5 (at 37° C.) .50 ul of 10XbaI buffer, 15 ul of XbaI (10U/ul), and 185 ul of H$_2$O were added to the 250 ul of water containing about 25 ug of plasmid pL110. The digestion proceeded at 37° C. for 1 hour. XbaI digested pL110 was then extracted in phenol, a 1/10 volume 3M CH$_3$COO—Na was added, 3 volumes of ethanol were added; the mixture was incubated in a dry ice-ethanol bath for 5 minutes, and then centrifuged. The precipitated DNA was resuspended in 50 ul H$_2$O.

The XbaI digested plasmid pCZR111 was digested with BamHI as follows. 0.2 ul of BamHI (10 U/ul), 10 ul of BamHI buffer (100 mM Tris-HCl, 50 mM MgCl$_2$, 1M NaCl, and 10 mM 2-Mercaptoethanol, pH 8.0 [at 37° C.], and 90 ul of H$_2$O was added to the 50 ul of XbaI digested pL110 obtained hereinabove. The digest proceeded for 5 minutes at 37° C. The digested pCZR111 was extracted in phenol, a 1/10 volumes of CH$_3$COONa was added, followed by addition of 3 volumes of ethanol. Precipitated DNA was resuspended in 50 ul of 10 mM Tris, 1 mM EDTA, pH 8.0 buffer.

The XbaI and BamHI digested pCZR111 was then loaded onto an agarose gel and the DNA band at about 5.8 kb was isolated. Plasmid pCZR126S was produced by ligating the ~5.8 kb fragment of pCZR111 to an XbaI to NdeI linker and a synthetic gene encoding EK-bovine growth hormone, which contains an NdeI site on its 5' end and a BamHI site on its 3' end. The XbaI to NdeI sequence was produced using standard oligonucleotide sequence methodology and consists of the following sequence: (Positive strand=Seq. ID No.12, Negative strand=Seq. ID No.13)

```
5' CTAGAGGGTATTAATAATGTATATTGATTTTAATAAGGAGGAATAATCA 3'
   ||||||||||||||||||||||||||||||||||||||||||||||||
   TCCCATAATTATTACATATAACTAAAATTATTCCTCCTTATTAGTAT 5'
```

The above sequence was constructed by chemical synthesis of both strand, followed by mixing to allow hybridization. The gene encoding EK bGH was constructed from 16 chemically synthesized pieces of single-stranded DNA, ranging from 71 to 83 nucleotides long, which together comprise both complementary strands of the entire gene. The synthesis was performed by using an Applied Biosystems (ABS) machine and consists of the following sequence: (Seq. ID Nos. 2 and 3)

```
5' TATGTTCCCATTGGATGATGATGATAAGTTCCCAGCCATGTCCTT
   |||||||||||||||||||||||||||||||||||||||||||||
   ACAAGGGTAACCTACTACTACTATTCAAGGGTCGGTACAGGAA

GTCCGGCCTGTTTGCCAACGCTGTGCTCCGGGCTCAGCACCTGCATCAGCTGGCTGCTGA
||||||||||||||||||||||||||||||||||||||||||||||||||||||||||||
CAGGCCGGACAAACGGTTGCGACACGAGGCCCGAGTCGTGGACGTAGTCGACCGACGACT

CACCTTCAAAGAGTTTGAGCGCACCTACATCCCGGAGGGACAGAGATACTCCATCCAGAA
||||||||||||||||||||||||||||||||||||||||||||||||||||||||||||
GTGGAAGTTTCTCAAACTCGCGTGGATGTAGGGCCTCCCTGTCTCTATGAGGTAGGTCTT
```

```
CACCCAGGTTGCCTTCTGCTTCTCTGAAACCATCCCGGCCCCCACGGGCAAGAATGAGGC
||||||||||||||||||||||||||||||||||||||||||||||||||||||||||||
GTGGGTCCAACGGAAGACGAAGAGACTTTGGTAGGGCCGGGGGTGCCCGTTCTTACTCCG

CCAGCAGAAATCAGACTTGGAGCTGCTTCGCATCTCACTGCTCCTCATCCAGTCGTGGCT
||||||||||||||||||||||||||||||||||||||||||||||||||||||||||||
GGTCGTCTTTAGTCTGAACCTCGACGAAGCGTAGAGTGACGAGGAGTAGGTCAGCACCGA

TGGGCCCCTGCAGTTCCTCAGCAGAGTCTTCACCAACAGCTTGGTGTTTGGCACCTCGGA
||||||||||||||||||||||||||||||||||||||||||||||||||||||||||||
ACCCGGGGACGTCAAGGAGTCGTCTCAGAAGTGGTTGTCGAACCACAAACCGTGGAGCCT

CCGTGTCTATGAGAAGCTGAAGGACCTGGAGGAAGGCATCCTGGCCCTGATGCGGGAGCT
||||||||||||||||||||||||||||||||||||||||||||||||||||||||||||
GGCACAGATACTCTTCGACTTCCTGGACCTCCTTCCGTAGGACCGGGACTACGCCCTCGA

GGAAGATGGCACCCCCCGGGCTGGGCAGATCCTCAAGCAGACCTATGACAAATTTGACAC
||||||||||||||||||||||||||||||||||||||||||||||||||||||||||||
CCTTCTACCGTGGGGGGCCCGACCCGTCTAGGAGTTCGTCTGGATACTGTTTAAACTGTG

AAACATGCGCAGTGACGACGCGCTGCTCAAGAACTACGGTCTGCTCTCCTGCTTCCGGAA
||||||||||||||||||||||||||||||||||||||||||||||||||||||||||||
TTTGTACGCGTCACTGCTGCGCGACGAGTTCTTGATGCCAGACGAGAGGACGAAGGCCTT

GGACCTGCATAAGACGGAGACGTACCTGAGGGTCATGAAGTGCCGCCGCT TCGGGGAGGC
|||||||||||||||||||||||||||||||||||||||||||||||||| |||||||||
CCTGGACGTATTCTGCCTCTGCATGGACTCCCAGTACTTCACGGCGGCGM  GCCCCGCCG

CAGCTGTGCCTTCTAG 3'
||||||||||||||||
GTCGACACGGAAGATCCTAG 5'
```

Figure 14:
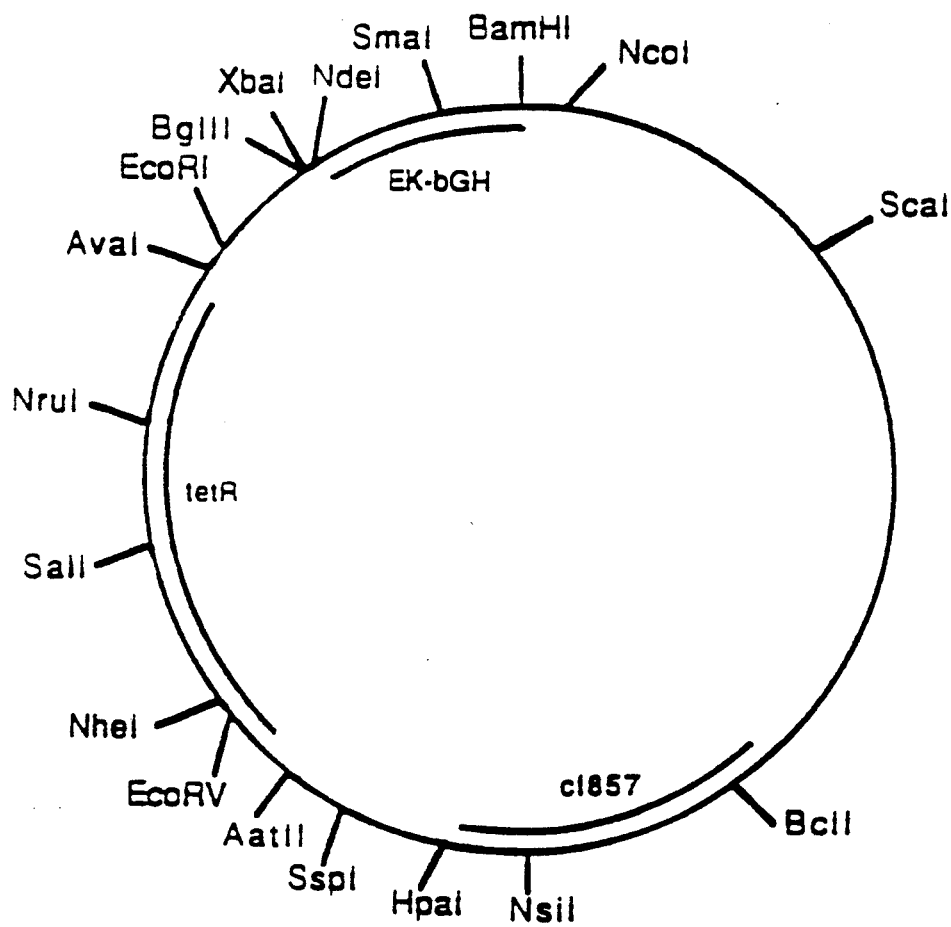
FIG. 14—A restriction site and function map of plasmid pCZR126S.

Construction of plasmid pCZR126S was accomplished by ligation of the following site components ~0.28 ug of the 5.8 kb fragment obtained from plasmid pL110 after complete digestion with XbaI and partial digestion with BamHI in a total volume of 2 ul, ~0.18 ug of the synthetic gene encoding a bovine growth factor derivative which has a 5' termini corresponding to a XbaI site and a 3' termini corresponding to a BamHI site in a total volume of 2.5 ul, 8.75 picomoles of the chemically synthesized XbaI to NdeI linker in 1 ul. The plasmid components were added to 6 ul of 5x ligation buffer: 250 mM Tris-HCl, 50 mM MgCl$_2$, 5 mM ATP, 5 mM DTT, 25% v/v polyethylene glycol 8,000, pH 7.6, 2 ul of ligase, and 16.5 ul of H$_2$O. The ligation mixture was incubated overnight at 16° C. The circularized plasmid pCZR126S was then used to transform E. coli RV308 cells in substantial accord with the method of Example 3A3. A restriction site and function map of plasmid pCZR126S is presented in FIG. 14 of the accompanying drawings.

EXAMPLE 4

Construction of Plasmid pRB182

About 20 μg of plasmid pRB181 prepared according to the teaching of Example 2 above was suspended in 20 μl of 10X NdeI buffer, 5 μl of NdeI restriction enzyme (Boehringer-Mannheim 40 units), 175 μl of water, gently mixed and incubated at 37° C. for 1 hour. Four microliters of BamHI restriction enzyme (Boehringer-Mannheim 40 units) was then added to the reaction mixture and the incubation at 37° C. was continued for another 2 hours. The DNA was precipitated with three volumes of ethanol and 0.3M NaOAc and electrophoresed on a 1.2% low melting agarose gel. The smaller (about 265 bp) NdeI/BamHI restriction fragment encoding the ACB-human proinsulin gene was sliced from the gel and the DNA was recovered by passing through an elutip-d column as described in Example 2. After precipitation and drying, the DNA was stored in 25 μl of 10 mM tris-HCl, pH=8.0.

About 15 mg of plasmid pCZR126S (the construction of which is taught in Example 3 above) was suspended in 20 μl of 10X NdeI buffer, 5 ml of NdeI restriction enzyme (40 units) and 175 μl of water, gently mixed and incubated at 37° C. for 2 hours. After the incubation, the DNA was precipitated with three volumes of ethanol as above, dried and then resuspended in 20 μl of 10X BamHI buffer, 2.5 μl of BamHI restriction enzyme (25 units) and 178 μl of water. After gentle mixing, the reaction was incubated at 37° C. for 2 hours. The DNA was again precipitated with three volumes of ethanol and electrophoresed on a 1% low melting agarose gel. The larger fragment corresponding to the vector DNA was sliced from this gel and the DNA was recovered by the Elutip-d column procedure as described in Example 2. After precipitation and drying the vector DNA was stored at 4° C. in 35 μl of 10 mM tris-HCl pH=8.0.

About 2.5 μl of the vector DNA was mixed with 12 μl of the purified ACB-proinsulin gene fragment from above, 4 μl of 10 mN ATP, 0.5 μl of 1M dithiothreitol, 5 μl of 10X ligase buffer (500 mM tris-HCl, pH=7.6, 100 mM MgCl$_2$), 26 μl of water and 0.5 μl of T4 DNA ligase (Pharmacia, Inc., 800 Centennial Avenue, Piscataway, N.J. 08854, 3.5 units). The reaction was incubated at 4° C. for 16 hours. The ligated mixture was diluted with 50 mL of 10 mM tris-HCl (pH=7.6) and 3 μl of 1M CaCl$_2$ and then subsequently transformed into E. coli K12 RV308 in accordance with the teaching of Example 3A3 above. The cells were plated on T4 agar plates supplemented with 5 μg/ml tetracycline and incubated overnight at 32° C.

Figure 20:
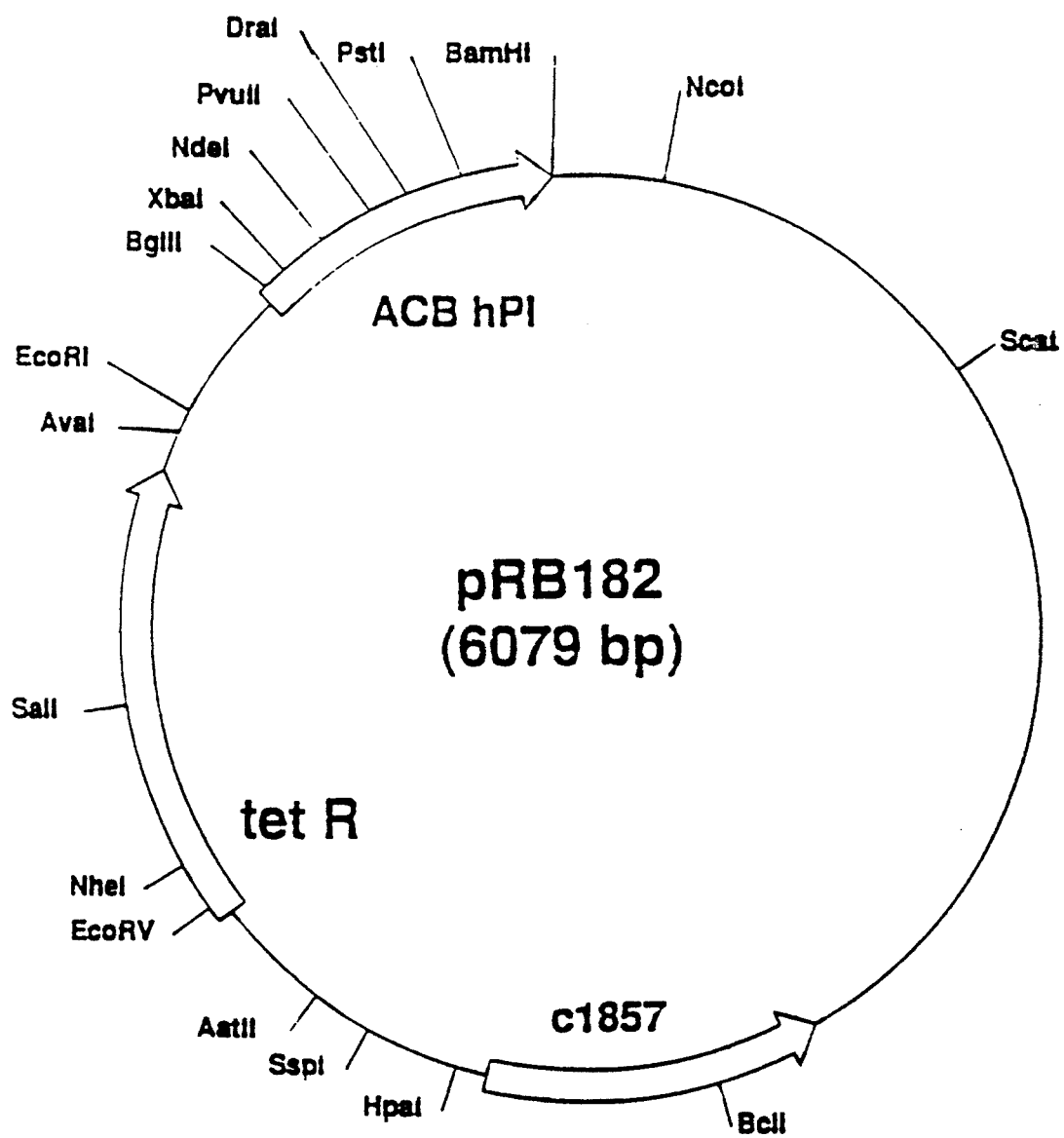
FIG. 20—A restriction site and function map of plasmid pRB182.

Plasmids from 3 mL cultures were isolated from the tetracycline resistant colonies by the rapid alkaline extraction procedure described in *Molecular Cloning: A Laboratory Manual*, (1982) edited by Maniatis, T., Fritsch, E. F., and Sambrook, J., Cold Spring Harbor Publications, New York, pgs.368–369, the entire teaching of which is hereby incorporated by reference. The presence of the correct human ACB-proinsulin gene fragment was determined by the miniscreen procedure according to the teaching of Birnboim, H. C., Edoly, J. (1979) *Nucleic Acids, Res.* 1, 1513–1523, using polyacrylamide gel elctrophoresis to analyze the XbaI/-BamHI digested fragment. Those plasmids with the correct size (about 314 bp) inserts were selected by amplification and purification. The expression plasmid containing the human ACB proinsulin gene is called pRB182. A restriction site and function map of plasmid pRB182 is presented in FIG. 20 of the accompanying drawings.

EXAMPLE 9

Fermentation

Scale-up production of cells for extraction and purification of recombinant ACB-proinsulin was accomplished using a BioFlo benchtop fermenter (commercially available from New Brunswick Scientific Co., Inc., P.O. Box 986, 44 Talmadge Road, Edison, N.J. 08817). Five liters of 2X TY broth containing 5ug/ml tetracycline (obtained from Sigma Chemical Co.) plus 1.0 ml of antifoam SAG 5693 (commercially available from Union Carbide, Specialty Chemical Division, Danbury, Conn. 06817-0001) was inoculated with 100 ml of bacterial culture of *E. coli* K12 RV 308 cells containing the pRB182 plasmid were grown overnight at 30° C. Cells were grown at 32° C. until the end of the exponential growth phase. Next, glucose and case-amino acids were added to concentrations of 0.2% and 0.1% respectively and the temperature shifted to 42° C. to induce protein synthesis. The cells were harvested from the growth medium twenty hours post-induction by centrifugation at 500 g for 10 minutes at 4° C. The supernatant was discarded and the pellet was washed once with ice cold TE buffer (10 mM Tris-HCl, pH 8.0, 1 mM EDTA).

Expression and accumulation of ACB-PI was determined by visualization of total cell protein following separation in a 10-20% polyacrylamide pore gradient gel in substantial accordance with the teachings of Laemmli, U.K. (1970) *Nature* (London), 227, 680-685 the entire teaching of which is hereby incorporated by reference. Pelleted cells were lysed by the addition of modified sample buffer (0.125M Tris-HCl, pH=6.8, 2%SDS, 30% glycerol, 1M 2-mercaptoethaol 6M urea) and boiled for 5 minutes prior to loading. Bands were detected by staining with Coomassie Blue and quantitaby scanning.

Specific identification of ACB-proinsulin was determined by Western Blot analysis in substantial accordance with the teaching of Johnson, D. A., et al., (1984) *Gene Anal. Techn* Vol. 1, pgs.3-8, using goat anti-HPI which recognizes the C-Peptide, followed by addition of a biotinylated second antibody (donkey anti-goat IgG) and visualization with the Vectastain protein detection kit (commercially available from vector Laboratories, Inc., 30 Ingold Rd., Burlingam, Calif. 94010) in substantial accordance with the directions supplied by the vendor.

EXAMPLE 6

Purification and Characterization of rDNA ACB-Proinsulin 43.5 g of *E. coli* cells (wet weight) were suspended in 400 ml of 20 mM Tris-HCl pH=7.6 containing 10 mM EDTA, 1 mM PMSF, 10% sucrose and 100 ug/ml lysozyme. The mixture was stirred vigorously for 1.5 hours at room temperature (approx. 25° C.), chilled on ice for 30 minutes, and the cells disrupted by sonication. The granules were collected by centrifugation at 2200g at 4° C. for one hour. The granules were then washed with 20 mM Tris-HCl, 1M NaCl, pH=7.6. The granules were dissolved with stirring in 200 ml of 20 mM Tris-HCl, 8M guanidine-HCl, pH=8.8. Next, 7g of Na$_2$SO$_3$ and 5g of Na$_2$S$_4$O$_6$ were added and the solution was stirred for three hours at room temperature. Following centrifugation, the supernatant was dialyzed using a 1000 MWCO dialysis bag (commercially available from Spectrum medical Industries, Inc., Los Angeles, Calif. 90060) against three changes of 2 liters of 10 mM ammonium acetate, pH=7.4. A precipitate developed which was collected by centrifugation at 2200g, 40° C., 1 hour. The supernatant was acidified to pH=3.6 with 6N HCl and the resulting precipitate collected and added to the precipitate from the dialysate.

EXAMPLE 7

Purification of ACB-Proinsulin S-Sulfonate

The pellet resulting from the teaching of Example 6 containing the ACB-proinsulin S-sulfonate, was dissolved in 20 mM Tris-HCl, 7.5M urea, pH=7.6 and was loaded onto a Mono Q HR 10/10 column (commercially available from Pharmacia LKB Biotechnology, 800 Centennial Ave., Piscataway, N.J. 08854). The column was eluted at 0.5 ml/min using a 760 minute gradient of 0.05 to 0.2M NaCl containing 20 mM Tris-HCl, pH 7.6, 7.5M urea. Fractions were analyzed by RP-HPLC using a gradient system of 30-42% CH$_3$CN into 0.1M (NH$_4$)$_2$HPO$_4$, pH 7.0, 1.5 ml/min on a 0.46×25 cm Zorbax C8 column (commercially available from DuPont, Wilmington, Del. 19898) thermostated at 45° C. The RP-HPLC seperations were carried out using a Rainin HP reverse phase HPLC apparatus (commercially available from Rainin Instruments, Woburn, Mass. 01801). Based on the analysis of fraction contents by RP-HPLC, two protein pools corresponding to ACB-proinsulin S-sulfonate were collected from the Mono Q column and desalted on a Zorbax C8 column by RP-HPLC using a gradient of 10-35% CH$_3$CN into 0.1M NH$_4$HCO$_3$, pH=8.0, frozen in liquid nitrogen and lyophilized.

EXAMPLE 8

Conversion of ACB-Proinsulin Sulfonate to ACB-Proinsulin

The ACB-proinsulin sulfonate lyophilisate prepared in Example 7 above was dissolved in 50 mM glycine, pH=10.5, 4° C., to a concentration of approximately 0.2 mg/ml. To this solution was added 2 equivalents of cysteine-HCl. After standing for 3 days, ACB-proinsulin was formed in approximately 75% yield.

The protein solution was then acidified with CF$_3$COOH to pH 2.0, loaded onto a RP-HPLC 2.2×25 cm Vydac C18 column (commercially available from The Separations Group, Hesperia, Calif. 92345) and eluted with an isocratic buffer of 0.1% CF$_3$COOH in H$_2$O:CH$_3$CN (72:28) at 1.5 ml/min. Fractions containing the desired material by analytical RP-HPLC were pooled, frozen in liquid nitrogen and lyophilized.

EXAMPLE 9

Determination of Disulfide Bond-Pairing in ACB-Proinsulin 250 mg of protein was dissolved in 250 ml of 0.05 ammonium bicarbonate, pH 9.0. 25 ul of a 0.1 mg/ml solution of pork trypsin (commercially available from Signma Chemical Co., P. O. Box 14508, St. Louis, Mo. 63178) in water was added and the digest incubated for 2 hours at 25° C. This trypsin digest which liberates the N-terminus of the B-chain, was stopped by the addition of 280 μl of 0.1N HCl. Then, 25 ul of a 0.1 mg/ml solution of pepsin (commercially available from BoehingerMannheim Biochemical, P. O. Box 50816, Indianapolis, Ind. 46250) in 0.01N HCl was added. The digest was incubated for 22 hours at 25° C., stopped by the additon of 25ul of a 0.1 mg/ml solution of pepstatin (commercially available from Sigma Chemical Co.) in 10% acetic acid and 900 ul of water. The digest was then loaded onto a 4.6×450 mm Zorbax C8 column thermostated at 45° C., which had been equilibrated with 0.1M sodium phosphate, pH 2.1, 1 ml/min and the peptides eluted with a linear gradient of 15 to 30% $CH_3CN$ into the starting buffer. The major peak eluting at 25% $CH_3CN$ was collected, diluted with water, desalted on a Sep-Pak cartridge (commercially available from waters,) and lyophilized. The collected material was then analyzed by amino acid analysis on a Model 6300 amino acid analyzes commercially available from Beckman Instruments, Fullerton, Calif. 92634.

The proper disulfide bond arragement of the ACB-proinsulins was confirmed through trypsin/pepsin digest of the molecules followed by HPLC analysis in substantial accordance with the teachings of Toren, P., et al., (1988) *Anal Biochem.*, Vol.169, pgs. 287-299.

EXAMPLE 10

Transformation of ACB-Proinsulin Into Human Insulin 1.03 mg of ACB-proinsulin was treated with 1 ug of trypsin (Sigma Chemical Co.) and 10 ug of carboxypeptidase B (Lilly, purified from porcine pancreas) in 2 ml of ammonium bicarbonate, pH=8.8 for 23 hours at 23° C. The reaction was terminated by the addition of 2.0 ml of 0.1N HCl and the sample was loaded in two 2 ml injections onto a 4.6×150 mm Vydac C18 column (commercially available from The Separations Group, Hesperia, Calif. 92345) equilibrated with 0.1% aqueous $CF_3COOH$ thermostated at 45° C. and eluted with a gradient program of 5 minutes 17% to 26.25%, 5 minutes 26.25% to 31.25%, and 35 minutes 31.25% to 42.5% $CH_3CN$ into 0.1% aqueous $CF_3COOH$, 1 ml/min. The eluted peptides were collected and analyzed by FAB-MS, amino acid analysis and in the case of the insulin containing peak, biological analysis and peptide mapping.

EXAMPLE 11

Biological Analysis of ACB-Proinsulin

Insulin and IGF-I recpetor binding assays using human placental membranes were performed essntially as described in Grappuso, P. A., et al., (1988) *J. Clin, Endocrinol. Metab.*, Vol.67, pgs. 194-197, the entire teaching of which is hereby incorporated by reference, except that the incubation was performed at 4° C. for 18 hours and membranes were collected on a Skatron Cell Harvester (commercially available from Skatron, Inc., Sterling, Va.). The glucose transport assay in rat adipocytes was performed in substantial accordance with the teachings of Kashwagi, M., et al., (1983) *J. Clin, Invest.*, Vol.72, pgs. 1246-1254, the entire teaching of which is hereby incorporated by reference.

In vivo activity of ACB-proinsulins was determined in fasted rats. Male, lean Sprague-Dawley rats (obtained from Charles River Laboratories, Wilmington, Mass. 01887) 190-210 g bodyweight, were fasted for 16 hours. Ten animals were chosen at random and divided into two groups of five rats each. The control group received a subcutaneous saline injection (0.1 ml per 100 g bodyweight) while the experimental groups received a saline injection containing the test peptide. Blood (0.1 ml) was obtained from the tail of each rat for glucose determination (Sigma Diagnostics, glucose [Trinder], address) before administration of the peptide and again at 30 minutes, 1, 2, 3 and 4 hours after administration of the peptide.

The mean percent change from zero time plus or minus S.E.M. in blood glucose for control and treated groups of rats were calculated and the final results expressed by adjusting the change in the experimental group for the change in the control group. The effect of 5 to 7 different doses of each peptide was routinely determined.

We claim:
1. A Polypeptide compound of the formula:

$$Met_x - A - C - B$$

wherein:
Met = the amino acid methionine,
x = 0 or 1,
A = the A chain of insulin or a functional derivative thereof,
B = the B chain of insulin or a functional derivative thereof, C=the C peptide of insulin or a peptide of the formula:

$$X_1—X_2—P—X_3—X_4,$$

wherein:
$X_1$, $X_2$, $X_3$, and $X_4$ are basic amino acids,
$X_1$, $X_2$, $X_3$, and $X_4$ are the same or different, and,
P is a peptide of from 4 to 35 amino acids which does not contain a cysteine residue, and pharmaceutically acceptable salts thereof.

2. The compound of claim 1 wherein the amino acid at position 21 of the A-chain is selected from the groups consisting of Gly, Ala, Asp or Asn.

3. The compound of claim 2 wherein the amino acid at position 10 of the B-chain is Asp.

4. The compound of claim 3 wherein the amino acid at position 30 of the B-chain is Ala or deleted.

5. The compound of claim 3 wherein the amino acid at position 29 of the B-chain is Pro.

6. The compound of claim 5 wherein the amino acid at position 28 of the B-chain is Glu or Lys.

7. The compound of claim 2 wherein the amino acid at position 27 of the B-chain is Arg.

8. The compound of claim 7 wherein the amino acid at position 13 of the B-chain is Gln.

9. The compound of claim 7 wherein the amino acid at position 17 of the A-chain is Glu.

10. The compound of claim 7 wherein the amino acid at position 21 of the A-chain is Gly and the amino acid at position 30 of the B-chain is Thr-NH$_2$.

11. The compound of claim 2 wherein the amino acid at position 29 of the B-chain in Pro.

12. The compound of claim 11 wherein the amino acid at position 28 of the B-chain is Lys or Glu.

13. The compound of claim 12 wherein the amino acid at position 30 of the B-chain is Ala.

14. The compound of claim 2 wherein the amino acid at position 30 of the B-chain is Ala.

15. The compound of claim 1 wherein the amino acid at position 10 of the B-chain is Asp or His.

16. The compound of claim 15 wherein the amino acid at position 28 of the B-chain is Asp.

17. The compound of claim 15 wherein the amino acid at position 30 of the B-chain is deleted.

18. The compound of claim 1 wherein the amino acid at position 28 of the B-chain is Lys, and the amino acid at position 29 of the B-chain is Pro.

19. The compound of claim 1 wherein the amino acids at positions 29 and 30 of the B-chain are deleted.

20. A DNA compound encoding the compound of claim 1.

21. A DNA compound encoding the compound of claim 2.

22. A DNA compound encoding the compound of claim 3.

23. A DNA compound encoding the compound of claim 4.

24. A DNA compound encoding the compound of claim 5.

25. A DNA compound encoding the compound of claim 6.

26. A DNA compound encoding the compound of claim 7.

27. A DNA compound encoding the compound of claim 8.

28. A DNA compound encoding the compound of claim 9.

29. A DNA compound encoding the compound of claim 10.

30. A DNA compound encoding the compound of claim 11.

31. A DNA compound encoding the compound of claim 12.

32. A DNA compound encoding the compound of claim 13.

33. A DNA compound encoding the compound of claim 14.

34. A DNA compound encoding the compound of claim 15.

35. A DNA compound encoding the compound of claim 16.

36. A DNA compound encoding the compound of claim 17.

37. A DNA compound encoding the compound of claim 18.

38. A DNA compound encoding the compound of claim 19.

39. A method of treating diabetes by administering a pharmaceutically acceptable dose of the compound of claim 1.

40. A method of treating non-insulin dependent diabetes mellitus by administering a pharmaceutically acceptable dose of the compound of formula 1.

41. A method to stimulate smooth muscle cell proliferation by administering the compound of claim 1.

* * * * *

UNITED STATES PATENT AND TRADEMARK OFFICE
CERTIFICATE OF CORRECTION

PATENT NO. : 5,304,473                                         Page 1 of 3

DATED : April 19, 1994

INVENTOR(S) : Belagaje, et al

It is certified that error appears in the above-identified patent and that said Letters Patent is hereby corrected as shown below:

In the drawings, add the Drawings Sheet consisting of Fig. 13 conti. as shown on the attached page.

UNITED STATES PATENT AND TRADEMARK OFFICE
CERTIFICATE OF CORRECTION

PATENT NO. : 5,304,473

DATED : April 19, 1994

INVENTOR(S) : Belagaje, et al

It is certified that error appears in the above-identified patent and that said Letters Patent is hereby corrected as shown below:

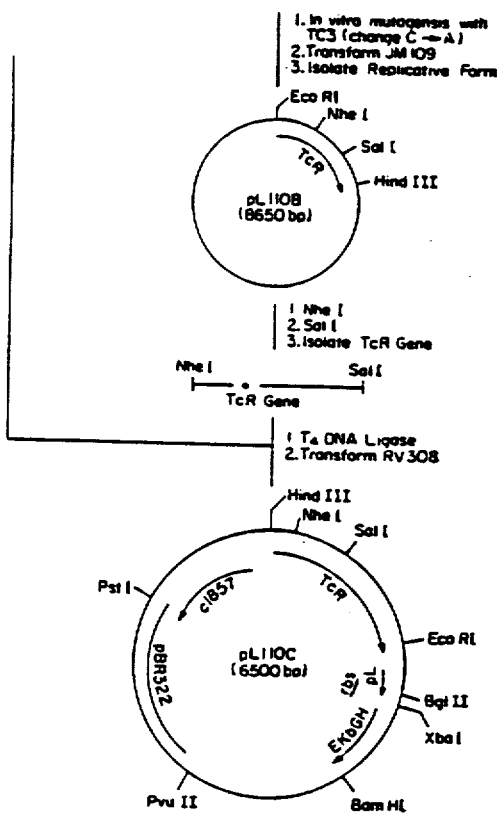

FIG. 13
Cont.

UNITED STATES PATENT AND TRADEMARK OFFICE
CERTIFICATE OF CORRECTION

PATENT NO. : 5,304,473
DATED : April 19, 1994
INVENTOR(S) : Belagaje, et al

It is certified that error appears in the above-indentified patent and that said Letters Patent is hereby corrected as shown below:

Column 12, line 41, "ACE-proinsulin," and should read -- ACB-proinsulin. --

Cloumn 12, line 49, "on its in activity," and should read -- on its in-vivo activity. --

Column 18, line 4, "ACE-PI," and should read -- ACB-PI. --

Column 20, line 18, "ACE-proinsulin," and should read -- ACB-proinsulin. --

Column 20, line 46, "ACE-PI peptide," and should read -- ACB-PI peptide. --

Column 20, line 55, "ACE-proinsulin," and should read -- ACB-proinsulin. --

Column 23, line 57, "ACB-preinsulin," and should read, -- ACB-proinsulin. --

Column 24, line 11, "A1-13/31-11," and should read, -- A1-13/B1-11. --

Column 41, line 9, "EXAMPLE 9," and should read, -- EXAMPLE 5. --

Signed and Sealed this

Ninth Day of January, 1996

BRUCE LEHMAN

*Attest:*

*Attesting Officer*           *Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 86 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Gly Ile Val Glu Gln Cys Cys Thr Ser Ile Cys Ser Leu Tyr Gln Leu
 1               5                  10                  15

Glu Asn Tyr Cys Asn Arg Arg Glu Ala Glu Asp Leu Gln Val Gly Gln
                20                  25                  30

Val Glu Leu Gly Gly Gly Pro Gly Ala Gly Ser Leu Gln Pro Leu Ala
             35                  40                  45
```

```
            Leu Glu Gly Ser Leu Gln Lys Arg Phe Val Asn Gln His Leu Cys Gly
                50                  55                  60

Ser His Leu Val Glu Ala Leu Tyr Leu Val Cys Gly Glu Arg Gly Phe
            65                  70                  75                  80

Phe Tyr Thr Pro Lys Thr
                            85
```

( 2 ) INFORMATION FOR SEQ ID NO:2:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
AGCTTCATAT GGGCATTGTG GAACAATGCT GTACCAGCAT CTGCTCCCTG TACCAGCTGG  60

AGAACTACTG CAACCGCCGT GAGGCAGAGG ACCTGCAGGT GGGTCAGGTG GAGCTGGGCG 120

GTGGCCCGGG TGCAGGCAGC CTGCAGCCGC TGGCCCTGGA GGGTTCCCTG CAGAAGCGTT 180

TTTTGAACCA ACACCTGTGC GGCTCCCACC TGGTGGAAGC TCTGTACCTG GTGTGCGGTG 240

AACGTGGCTT CTTCTACACC CCGAAGACCT AGGATCCG                        278
```

( 2 ) INFORMATION FOR SEQ ID NO:3:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AATTCGGATC CTAGGTCTTC GGGTGTAGAA GAAGCCACGT TCACCGCACA CCAGGTACAG  60

AGCTTCCACC AGGTGGGAGC CGCACAGGTG TTGGTTCAAA AAACGCTTCT GCAGGGAACC 120

CTCCAGGGCC AGCGGCTGCA GGCTGCCTGC ACCCGGGCCA CCGCCCAGCT CCACCTGACC 180

CACCTGCAGG TCCTCTGCCT CACGGCGGTT GCAGTAGTTC TCCAGCTGGT ACAGGGAGCA 240

GATGCTGGTA CAGCATTGTT CCACAATGCC CATATGA                         277
```

( 2 ) INFORMATION FOR SEQ ID NO:4:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CCTCGAGG                                                           8
```

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GATCTATTAA CTCAATCTAG AC 22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TCGAGTCTAG ATTGAGTTAA TA 22

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGGGATCCCG 10

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GAGGAATTCC TC 12

( 2 ) INFORMATION FOR SEQ ID NO:9:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CTGTGCCTTC TAG 13

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GATCCTAGAA GGCACAG 17

( 2 ) INFORMATION FOR SEQ ID NO:11:

( i ) SEQUENCE CHARACTERISTICS:

(A) LENGTH: 26 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:11:

CCCGTCCTGT GGATACTCTA CGCCGA                        26

(2) INFORMATION FOR SEQ ID NO:12:

(i) SEQUENCE CHARACTERISTICS:
(A) LENGTH: 49 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:12:

CTAGAGGGTA TTAATAATGT ATATTGATTT TAATAAGGAG GAATAATCA    49

(2) INFORMATION FOR SEQ ID NO:13:

(i) SEQUENCE CHARACTERISTICS:
(A) LENGTH: 47 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:13:

TATGATTATT CCTCCTTATT AAAATCAATA TACATTATTA ATACCCT      47

(2) INFORMATION FOR SEQ ID NO:14:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:14:

Gly Phe Phe Tyr Thr Pro Lys
1               5

(2) INFORMATION FOR SEQ ID NO:15:

(i) SEQUENCE CHARACTERISTICS:
(A) LENGTH: 8 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:15:

Gly Phe Phe Tyr Thr Pro Lys Thr
1               5